United States Patent
Shin et al.

(10) Patent No.: US 12,098,198 B2
(45) Date of Patent: Sep. 24, 2024

(54) ANTIBODY BINDING SPECIFICALLY TO ECL-2 OF CLAUDIN 3, FRAGMENT THEREOF, AND USE THEREOF

(71) Applicant: ABION INC., Seoul (KR)

(72) Inventors: Young Kee Shin, Seoul (KR); Sung Youl Hong, Seoul (KR); Young Deug Kim, Seoul (KR); Jun Young Choi, Seoul (KR); Heo Bin Yang, Seoul (KR); Ha Yeon Park, Seoul (KR); Sung Su Kim, Seoul (KR)

(73) Assignee: ABION INC., Seoul (KR)

( * ) Notice: Subject to any disclaimer, the term of this patent is extended or adjusted under 35 U.S.C. 154(b) by 709 days.

(21) Appl. No.: 17/042,374

(22) PCT Filed: Mar. 27, 2019

(86) PCT No.: PCT/KR2019/003594
§ 371 (c)(1),
(2) Date: Sep. 28, 2020

(87) PCT Pub. No.: WO2019/190206
PCT Pub. Date: Oct. 3, 2019

(65) Prior Publication Data
US 2021/0115134 A1    Apr. 22, 2021

(30) Foreign Application Priority Data

Mar. 28, 2018   (KR) .................. 10-2018-0036190

(51) Int. Cl.
| | |
|---|---|
| *C07K 16/28* | (2006.01) |
| *A61K 39/00* | (2006.01) |
| *A61P 35/00* | (2006.01) |
| *G01N 33/574* | (2006.01) |

(52) U.S. Cl.
CPC .............. *C07K 16/28* (2013.01); *A61P 35/00* (2018.01); *G01N 33/57492* (2013.01); *A61K 2039/505* (2013.01); *C07K 2317/33* (2013.01); *C07K 2317/565* (2013.01); *C07K 2317/622* (2013.01); *C07K 2317/732* (2013.01); *C07K 2317/77* (2013.01); *C07K 2317/92* (2013.01); *C07K 2319/03* (2013.01)

(58) Field of Classification Search
None
See application file for complete search history.

(56) References Cited

U.S. PATENT DOCUMENTS

| | | |
|---|---|---|
| 9,212,228 B2 | 12/2015 | Sahin et al. |
| 2014/0274755 A1 | 9/2014 | Shin et al. |
| 2018/0282389 A1 | 10/2018 | Breitkreuz et al. |
| 2019/0077876 A1 | 3/2019 | Aujay et al. |
| 2021/0115134 A1 | 4/2021 | Shin et al. |

FOREIGN PATENT DOCUMENTS

| | | | | |
|---|---|---|---|---|
| EP | 2103628 A1 | * | 9/2009 | ............. A61P 35/00 |
| EP | 3778638 A1 | | 2/2021 | |
| KR | 10-2013-0086591 | | 8/2013 | |
| KR | 10-2017-0118633 | | 10/2017 | |
| RU | 2445319 C2 | | 3/2013 | |
| WO | WO-2016164731 A2 | * | 10/2016 | ............. A61K 35/17 |
| WO | 2019190206 A1 | | 3/2019 | |

OTHER PUBLICATIONS

Romani, Chiara. Evaluation of a novel human IgG1 anti-claudin 3 antibody that specifically recognizes its aberrantly localized antigen in ovarian cancer cells and that is suitable for selective drug delivery. Oncotarget, vol. 6, No. 33. Published Sep. 21, 2015 (Year: 2015).*
Office Action received in corresponding Canadian Application No. 3,095,139, mailed Oct. 11, 2023, 5 pages.
International Search Report [English] and Written Opinion dated Jul. 5, 2019, from International Application No. PCT/KR2019/003594, 20 pages.
Romani, C. "Evaluation of a novel human IgG1 anti-claudin3 antibody that specifically recognizes its aberrantly localized antigen in ovarian cancer cells and that is suitable for selective drug delivery", Oncotarget, vol. 6, No. 33, 13 pages, Sep. 21, 2015.

* cited by examiner

*Primary Examiner* — Daniel E Kolker
*Assistant Examiner* — Maureen Varina Driscoll
(74) *Attorney, Agent, or Firm* — Meunier Carlin & Curfman LLC

(57) ABSTRACT

The invention of the present application relates to a use of an antibody binding specifically to ECL-2 of claudin 3 and functional fragments thereof in cancer cell detection, diagnosis, imaging, and application to cancer treatment (anticancer use of the antibody itself, and application to ADC and CAR-expression cells (particularly immune cells)), an antibody that includes a characteristic CDR sequence exerting a remarkable effect in such uses, and a functional fragment thereof.

17 Claims, 27 Drawing Sheets
Specification includes a Sequence Listing.

FIG. 4B

```
Human Claudin 3   ECL1   27  PMWRVSAFIGSNIITSQNIWEGLWMNCVVQSTGQMQCKVYDSLLALPQDLQAAR  80   54
Human Claudin 4   ECL1   28  PMWRVTAFIGSNIVTSQTIWEGLWMNCVVQSTGQMQCKVYDSLLALPQDLQAAR  81   51 (94.3%)
Human Claudin 5   ECL1   28  PMWQVTAFLDHNIVTAQTTWKGLWMSCVVQSTGHMQCKVYDSVLALSTEVQAAR  81   37 (68.5%)
Human Claudin 6   ECL1   28  PMWKVTAFIGNSIVVAQVVWEGLWMSCVVQSTGQMQCKVYDSLLALPQDLQAAR  81   44 (81.5%)
Human Claudin 8   ECL1   28  PQWRVSAFIENNIVVFENFWEGLWMNCVRQANIRMQCKIYDSLLALSPDLQAAR  81   38 (70.4%)
Human Claudin 9   ECL1   28  PLWFVTAFIGNSIVVAQVVWEGLWMSCVVQSTGQMQCKVYDSLLALPQDLQAAR  81   43 (79.6%)
Human Claudin 17  ECL1   28  PQWRVSAFVGSNIIVPEKLWEGLWMNCIRQARVELQCKFYSSLLALPPALETAR  81   34 (63.0%)
Human Claudin 1   ECL1   28  PQWRIYSYAGDNIVTAQAMYEGLWMSCVSQSTGQIQCKVFDSLLNLSSTLQATR  81   33 (61.1%)
Mouse Claudin 3   ECL1   27  PMWRVSAFIGSSIITAQITWEGLWMNCVVQSTGQMQCKMYDSLLALPQDLQAAR  80   49 (90.7%)

Human Claudin 3   ECL2  144  RDFYNPVVPEAQKREM  159   16
Human Claudin 4   ECL2  145  QDFYNPLVASQKREM   160   11 (68.8%)
Human Claudin 5   ECL2  145  REFYDPSVPSQKYEL   160    9 (56.3%)
Human Claudin 6   ECL2  145  RDFYNPLVAEAQKREL  160   13 (81.3%)
Human Claudin 8   ECL2  146  RDFYNSIVSVAQKREL  161   11 (68.8%)
Human Claudin 9   ECL2  145  QDFYNPLVAEALKREL  160   11 (68.8%)
Human Claudin 17  ECL2  146  RDFYNPAIHIGQKREL  161   10 (62.5%)
Human Claudin 1   ECL2  145  QEFYDPMTPVNARYEF  160    5 (31.3%)
Mouse Claudin 3   ECL2  144  RDFYNPLVPEAQKREM  159   15 (93.8%)
```

Bold : Matched amino acid sequence with hCLDN3

Scale bar : 50 μm

Scale bar : 50 μm

✦ CHO-K1 (CLDN3 -)

Control

Commercial
Anti-CLDN3

4G3 (hIgG)

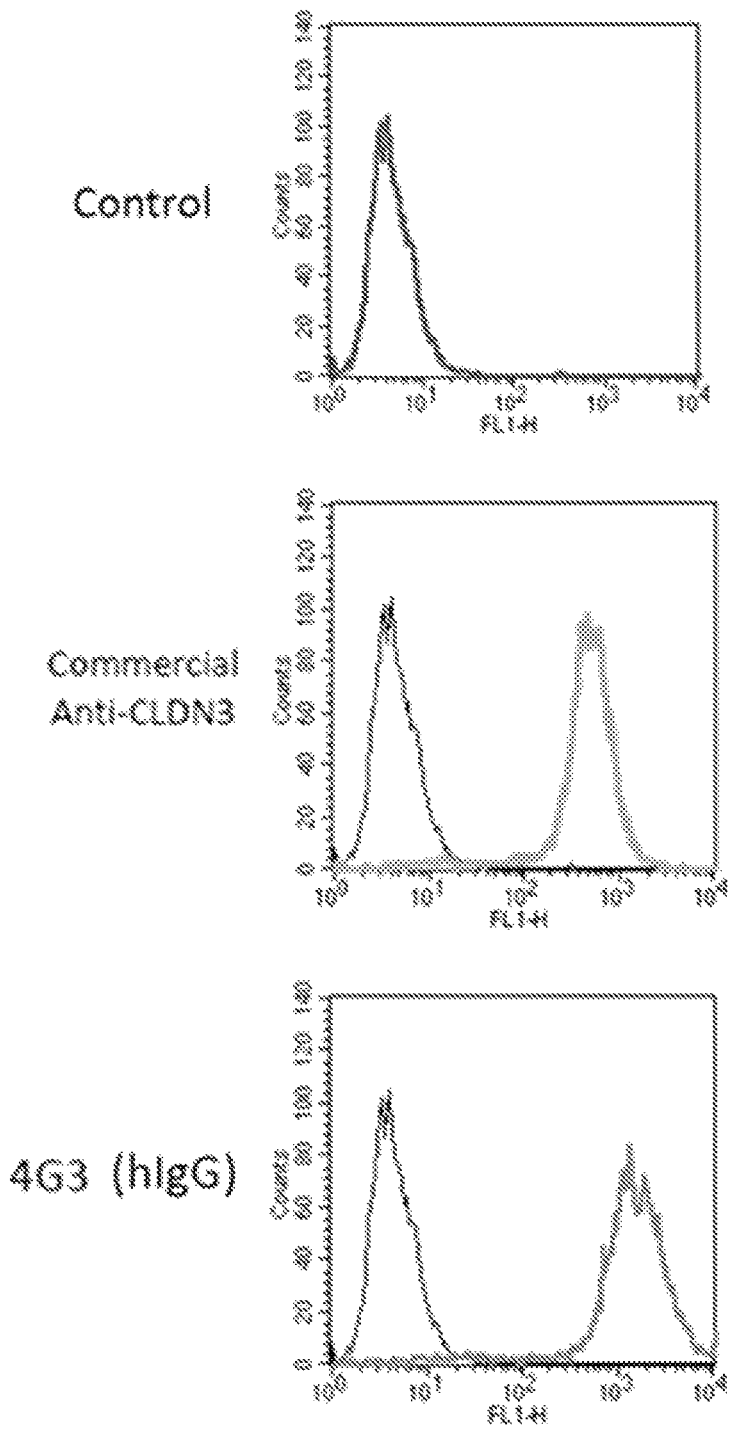

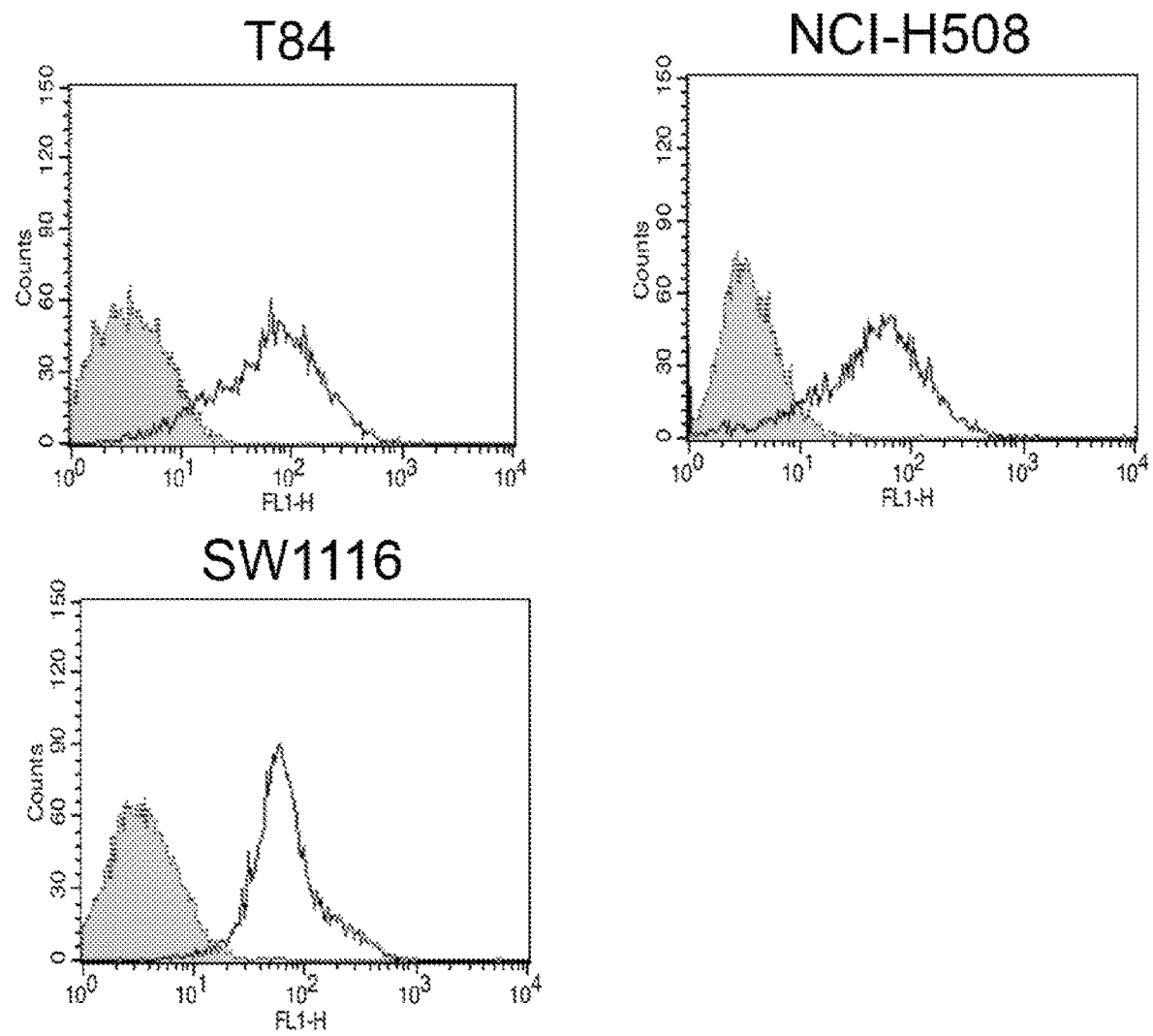

ANTIBODY BINDING SPECIFICALLY TO ECL-2 OF CLAUDIN 3, FRAGMENT THEREOF, AND USE THEREOF

This application is a national phase application filed under 35 U.S.C. § 371 of PCT International Application No. PCT/KR2019/003594, filed on Mar. 27, 2019, which claims priority to, and the benefit of, Korean Patent Application No. 10-2018-0036190, filed on Mar. 28, 2018, the entire contents of which are incorporated herein by reference.

SEQUENCE LISTING

A Sequence Listing conforming to the rules of WIPO Standard ST.25 is hereby incorporated by reference. Said Sequence Listing has been filed as an electronic document via EFS in ASCII formatted text. The electronic document, created on Apr. 7, 2023, is entitled "11239-005US1_ST25", and is 21,780 bytes in size.

TECHNICAL FIELD

This application claims priority from Korean Patent Application No. 10-2018-0036190, filed on Mar. 28, 2018, the entire contents of which are incorporated herein by reference.

The present invention relates to an antibody that specifically binds to the extracellular second loop (ECL-2) of claudin 3, a fragment thereof, and uses thereof, and more particularly, to a use of an antibody biding specifically to ECL-2 of claudin 3 and functional fragments thereof in cancer cell detection, diagnosis, imaging, and application to cancer treatment (anticancer use of the antibody itself, and application to ADC and CAR-expression cells (particularly, immune cells)), an antibody that includes a characteristic CDR sequence exerting a remarkable effect in such uses, and a functional fragment thereof.

BACKGROUND OF THE INVENTION

Claudin is a major and essential membrane protein of tight junction (TJ) between cells, and there are 27 families in mammals. Humans have the claudin family except claudin 13 in mammals. The claudin family has a similar structure that penetrates the cell wall and is embedded in it, and most have a structure with two extracellular loops. Claudin is known to play a role in controlling the flow of molecules between cells, but recent studies have reported that it is closely related to the incidence of cancer such as colon cancer, stomach cancer, breast cancer, esophageal cancer, and ovarian cancer. About 90% of malignant tumors originate from the epithelium. In normal epithelial cells, the cells are located parallel to the epithelial plane. Therefore, claudin, which constitutes TJ between normal epithelial tissues, is difficult to detect on the surface of tissues or organs, but in the early stages of epithelial tumor development, the control of the mitotic spindle is released and cells proliferate by off-plane division, exposing claudin to the tissue surface In particular, it has been reported that claudin 3 and claudin 4 are overexpressed in the claudin family in ovarian cancer, which is known to have a poor prognosis because there is no obvious symptom and there is no appropriate treatment method other than surgery and chemotherapy (Claudin Proteins in Human Cancer: Promising New Targets for Diagnosis and Therapy, P. J. Morin, Cancer Res. 65: 9604-9006 (2005)). In addition, as a result of confirming the survival rate of 84 patients with ovarian serous adenocarcinoma and the expression rate of claudin 3 by the survival curve of the Kaplan-Meier technique, a study was reported that the expression rate of claudin 3 was closely related to the shortening of the patient's lifespan (Expression profile of tight junction protein claudin 3 and claudin 4 in ovarian serous adenocarcinoma with prognostic, Choi et al., Histol. Histopathol. 22:1185~1195(2005)). As described above, the increase or decrease of the expression of claudin with high specificity in cancer tissues can be used as a predictive indicator for cancer generation. In addition, claudin has become a useful biomarker in the diagnosis and treatment of cancer, and various groups are trying to develop therapeutic agents targeting claudin.

Meanwhile, an antibody-drug-conjugate (ADC) is a combination of the target specificity of a monoclonal antibody and the properties of the drug's efficacy (e.g., cytotoxicity). ADC consists of three components, including drugs, monoclonal antibodies, and a linker that connects the antibody to the drug. ADC technology mainly uses antibodies that specifically bind to specific antigens expressed on the surface of cancer cells. It is used as a method of delivering drugs to tumor cells. However, not all antibodies that simply target specific cancer antigens can be applied to ADCs.

Existing antibodies cannot penetrate directly into living cells due to their large size and hydrophilicity. Therefore, most of the existing antibodies specifically target proteins or cell membrane proteins secreted to the outside of cells. General antibodies and polymer biopharmaceuticals have limitations in that they cannot bind to and inhibit various disease-related substances inside the cytoplasm because they cannot pass through the hydrophobic cell membrane. In general, commercial antibodies that specifically bind to intracellular substances used in experiments for the study of mechanisms such as cell growth and specific inhibition cannot be directly treated on living cells, and in order to bind with intracellular substances, a pretreatment process to form a perforation in the cell membrane through the cell membrane permeabilization process using saponin, an amphiphilic glycoside, is essential. In the case of low-molecular substances, nucleic acids, or nanoparticles, they can be transported into living cells by using various reagents, electroporation, or thermal shock, but in the case of proteins and antibodies, most of the reagents and experimental conditions described above may adversely affect the intrinsic tertiary structure, resulting in loss of activity. An intracellular antibody (intrabody) that specifically binds to and inhibits the activity of intracellular proteins is being developed, but it also has no activity to penetrate the cell membrane of living cells, so it can only be applied for gene therapy purposes. Therefore, future application possibilities are very limited (Manikandan J et al., Protein i: interference at protein level by intrabodies, Front Biosci, 2007 Jan. 1; 12:1344-52).

Some therapeutic approaches including antibody-drug conjugates (ADCs), immunotoxins, and targeted nucleic acid delivery require antibodies that not only bind to receptors, but also internalize into cells upon binding. It is known that ADCs need to enter cells (internalization) in order for ADCs to exhibit excellent efficacy. However, depending on the antibody, there is no ability to enter the cell, or because the deviation thereof is very large, antibodies that can be developed with actual ADCs and their effects are limited.

DETAILED DESCRIPTION OF THE INVENTION

Technical Problem

Therefore, while the inventors of the present invention were studying to develop an antibody having various properties suitable for use as an ADC (antibody-drug conjugate), they have completed the present invention after they confirmed the value of an antibody and a functional fragment that specifically bind to claudin 3 ECL-2 for cancer cell detection, diagnosis, imaging, and application to cancer treatment (such as application to ADC and CAR-expressing cells (especially immune cells)). As a specific example of this, they confirmed that the antibody comprising the unique CDR sequence provided by the present invention not only has anticancer ability by itself, but also exhibits excellent cancer cell targeting ability without cross-reactivity with other claudin families, and they confirmed that it exhibits very excellent binding strength (affinity) compared to the existing known claudin 3 antibody and exhibits remarkable effects in the above application by possessing properties such as cell internalization.

Therefore, an aspect of the present invention is to provide an antibody or a functional fragment thereof comprising a heavy chain complementarity determining region 1 (VH-CDR1) comprising an amino acid sequence defined by SEQ ID NO: 3, a heavy chain complementarity determining region 2 (VH-CDR1) comprising an amino acid sequence defined by SEQ ID NO: 4-CDR2), and a heavy chain variable region comprising a heavy chain complementarity determining region 3 (VH-CDR3) comprising an amino acid sequence defined by SEQ ID NO: 5; and light chain complementarity determining region 1 (VL-CDR1) comprising the amino acid sequence defined by SEQ ID NO: 6, light chain complementarity determining region 2 (VL-CDR2) comprising the amino acid sequence defined by SEQ ID NO: 7, and a light chain variable region comprising a light chain complementarity determining region 3 (VL-CDR3) comprising the amino acid sequence defined by SEQ ID NO: 8.

Another aspect of the present invention is to provide a polynucleotide encoding the antibody or functional fragment thereof, a vector containing the same, a cell containing the same, and a method for producing the antibody or functional fragment thereof using the same.

Another aspect of the present invention is to provide a composition for detecting claudin 3 comprising the antibody or functional fragment thereof as an active ingredient and a method for detecting claudin 3 using the same.

In addition, it is to provide a composition for detecting claudin 3 consisting of the antibody or functional fragment thereof, and a method for detecting claudin 3 using the same.

In addition, it is to provide a composition for detecting claudin 3 consisting essentially of the antibody or a functional fragment thereof, and a method for detecting claudin 3 using the same.

Another aspect of the present invention is to provide a composition for diagnosis or imaging of cancer comprising the antibody or a functional fragment thereof as an active ingredient.

Further, it is to provide a composition for diagnosis or imaging of cancer consisting of the antibody or functional fragment thereof.

In addition, it is to provide a composition for diagnosis or imaging of cancer, which consists essentially of the antibody or a functional fragment thereof.

Another aspect of the present invention is to provide a composition for preventing and treating cancer comprising the antibody or functional fragment thereof as an active ingredient.

In addition, it is to provide a composition for preventing and treating cancer consisting of the antibody or functional fragment thereof.

In addition, it is to provide a composition for preventing and treating cancer consisting essentially of the antibody or functional fragment thereof.

Another aspect of the present invention is to provide a composition for drug delivery specific to cancer cells, specifically comprising the antibody or a functional fragment thereof as an active ingredient.

It is also to provide a composition for drug delivery specific to cancer cells consisting of the antibody or functional fragment thereof.

In addition, it is to provide a composition for drug delivery specific to cancer cells consisting essentially of the antibody or functional fragment thereof.

Still another aspect of the present invention is to provide a composition for intracellular drug delivery comprising an antibody or a functional fragment thereof that specifically binds to the extracellular second loop (ECL-2) of claudin 3 as an active ingredient.

In addition, it is to provide a composition for intracellular drug delivery consisting of an antibody or functional fragment thereof that specifically binds to the extracellular second loop (ECL-2) of claudin 3.

In addition, it is to provide a composition for intracellular drug delivery consisting essentially of an antibody or a functional fragment thereof that specifically binds to the extracellular second loop (ECL-2) of claudin 3.

Still another aspect of the present invention is to provide a composition for preventing and treating cancer comprising an antibody-drug conjugate in which the antibody or functional fragment is bound to a drug as an active ingredient.

In addition, it is to provide a composition for preventing and treating cancer consisting of an antibody-drug conjugate in which the antibody or functional fragment is bound to a drug as an active ingredient.

In addition, it is to provide a composition for preventing and treating cancer consisting essentially of an antibody-drug conjugate in which the antibody or functional fragment is bound to a drug as an active ingredient.

Still another aspect of the present invention is to provide a composition for preventing and treating cancer comprising intracellular drug delivery comprising an antibody-drug conjugate in which a drug is bound to an antibody or a functional fragment thereof that specifically binds to the extracellular second loop (ECL-2) of claudin 3 as an active ingredient.

In addition, it is to provide a composition for preventing and treating cancer consisting of intracellular drug delivery comprising an antibody-drug conjugate in which a drug is bound to an antibody or a functional fragment thereof that specifically binds to the extracellular second loop (ECL-2) of claudin 3 as an active ingredient.

In addition, it is to provide a composition for preventing and treating cancer consisting essentially of intracellular drug delivery comprising an antibody-drug conjugate in which a drug is bound to an antibody or a functional fragment thereof that specifically binds to the extracellular second loop (ECL-2) of claudin 3 as an active ingredient.

Still another aspect of the present invention is to provide a chimeric antigen receptor (CAR) protein comprising; i) the antibody or functional fragment thereof of the present invention; ii) a transmembrane domain; and iii) an intracellular signlaing domain.

In addition, it is to provide a chimeric antigen receptor (CAR) protein comprising; i) an antibody or a functional fragment thereof that specifically binds to the extracellular second loop (ECL-2) of claudin 3; ii) a transmembrane domain; and iii) an intracellular signlaing domain.

Still another aspect of the present invention is to provide a polynucleotide encoding the chimeric antigen receptor (CAR) protein, a recombinant vector comprising the same, and a cell (especially, an immune cell) transformed with the vector.

Still further aspect of the present invention is to provide the use of the antibody or functional fragment thereof to prepare an agent for detection of claudin 3, an agent for diagnosis of cancer, an agent for imaging cancer, and an agent for drug delivery specific to cancer cells.

Still further aspect of the present invention is to provide a method for specific detection of claudin 3, a method for diagnosing cancer, a cancer imaging method, and a method for drug delivery specific to cancer cells, comprising administering an effective amount of a composition comprising the antibody or functional fragment thereof as an active ingredient to a subject in need thereof.

Still further aspect of the present invention is to provide use of an antibody-drug conjugate in which the antibody or functional fragment thereof is bound to a drug for preparing an agent for preventing and treating cancer.

Still further aspect of the present invention is to provide a method for preventing and treating cancer, the method comprising administering an effective amount of a composition comprising an antibody-drug conjugate, in which the antibody or functional fragment thereof is bound to a drug, as an active ingredient to a subject in need thereof.

Still further aspect of the present invention is to provide use of an antibody or a functional fragment thereof that specifically binds to the extracellular second loop (ECL-2) of claudin 3 for preparing an agent of intracellular drug delivery.

Still further aspect of the present invention is to provide a method for intracellular drug delivery comprising administering an effective amount of a composition comprising an antibody or a functional fragment thereof that specifically binds to the extracellular second loop (ECL-2) of claudin 3 as an active ingredient to a subject in need thereof.

Still further aspect of the present invention is to provide use of an antibody or a functional fragment thereof that specifically binds to the extracellular second loop (ECL-2) of claudin 3; and a drug bound thereto for preparing an agent for preventing and treating cancer.

Still further aspect of the present invention is to provide a method for preventing and treating cancer, comprising administering an effective amount of a composition comprising, as an active ingredient, an antibody or a functional fragment thereof that specifically binds to the extracellular second loop (ECL-2) of claudin 3; and a drug bound thereto to a subject in need thereof.

Technical Solution

An embodiment according to an aspect of the present invention provides an antibody or a functional fragment thereof comprising:
a heavy chain variable region comprising a heavy chain complementarity determining region 1 (VH-CDR1) comprising an amino acid sequence defined by SEQ ID NO: 3, a heavy chain complementarity determining region 2 (VH-CDR2) comprising an amino acid sequence defined by SEQ ID NO: 4, and a heavy chain complementarity determining region 3 (VH-CDR3) comprising an amino acid sequence defined by SEQ ID NO: 5; and
a light chain variable region comprising a light chain complementarity determining region 1 (VL-CDR1) comprising an amino acid sequence defined by SEQ ID NO: 6, a light chain complementarity determining region 2 (VL-CDR2) comprising an amino acid sequence defined by SEQ ID NO: 7, and a light chain complementarity determining region 3 (VL-CDR3) comprising an amino acid sequence defined by SEQ ID NO: 8.

An embodiment according to another aspect of the present invention provides a polynucleotide encoding the antibody or functional fragment thereof, a vector containing the same, a cell containing the same, and a method for producing the antibody or functional fragment thereof using the same.

An embodiment according to another aspect of the present invention provides a composition for detecting claudin 3 comprising the antibody or functional fragment thereof as an active ingredient and a method for detecting claudin 3 using the same.

In addition, the present invention provides a composition for detecting claudin 3 consisting of the antibody or functional fragment thereof, and a method for detecting claudin 3 using the same.

In addition, the present invention provides a composition for detecting claudin 3 consisting essentially of the antibody or functional fragment thereof, and a method for detecting claudin 3 using the same.

An embodiment according to another aspect of the present invention provides a composition for diagnosis or imaging of cancer comprising the antibody or a functional fragment thereof as an active ingredient.

In addition, the present invention provides a composition for diagnosis or imaging of cancer consisting of the antibody or a functional fragment thereof.

In addition, the present invention provides a composition for diagnosing or imaging cancer consisting essentially of the antibody or a functional fragment thereof.

An embodiment according to another aspect of the present invention provides a composition for preventing and treating cancer comprising the antibody or functional fragment thereof as an active ingredient.

In addition, the present invention provides a composition for preventing and treating cancer consisting of the antibody or functional fragment thereof.

In addition, the present invention provides a composition for preventing and treating cancer consisting essentially of the antibody or functional fragment thereof.

An embodiment according to another aspect of the present invention provides a composition for drug delivery specific to cancer cells, specifically comprising the antibody or a functional fragment thereof as an active ingredient.

In addition, the present invention provides a composition for drug delivery specific to cancer cells consisting of the antibody or functional fragment thereof.

In addition, the present invention provides a composition for drug delivery specific to cancer cells consisting essentially of the antibody or functional fragment thereof.

In addition, an embodiment according to still another aspect of the present invention provides a composition for intracellular drug delivery comprising an antibody or a functional fragment thereof that specifically binds to the extracellular second loop (ECL-2) of claudin 3 as an active ingredient.

In addition, the present invention provides a composition for intracellular drug delivery consisting of an antibody or functional fragment thereof that specifically binds to the extracellular second loop (ECL-2) of claudin 3.

In addition, the present invention provides a composition for intracellular drug delivery consisting essentially of an antibody or functional fragment thereof that specifically binds to the extracellular second loop (ECL-2) of claudin 3.

An embodiment according to still another aspect of the present invention provides a composition for preventing and treating cancer comprising an antibody-drug conjugate in which a drug is bound to the antibody or a functional fragment thereof as an active ingredient.

In addition, the present invention provides a composition for preventing and treating cancer consisting of an antibody-drug conjugate in which a drug is bound to the antibody or a functional fragment thereof as an active ingredient.

In addition, the present invention provides a composition for preventing and treating cancer consisting essentially of an antibody-drug conjugate in which a drug is bound to the antibody or a functional fragment thereof as an active ingredient.

In addition, an embodiment according to still another aspect of the present invention provides an antibody-drug conjugate comprising an antibody or a functional fragment thereof that specifically binds to the extracellular second loop (ECL-2) of claudin 3; and a drug bound thereto, and a composition for preventing and treating cancer comprising the antibody-drug conjugate as an active ingredient.

In addition, the present invention provides an antibody-drug conjugate comprising an antibody or a functional fragment thereof that specifically binds to the extracellular second loop (ECL-2) of claudin 3; and a drug bound thereto, and a composition for preventing and treating cancer consisting of the antibody-drug conjugate as an active ingredient.

In addition, the present invention provides an antibody-drug conjugate comprising an antibody or a functional fragment thereof that specifically binds to the extracellular second loop (ECL-2) of claudin 3; and a drug bound thereto, and a composition for preventing and treating cancer consisting essentially of the antibody-drug conjugate as an active ingredient.

An embodiment according to still another aspect of the present invention provides a chimeric antigen receptor (CAR) protein comprising; i) the antibody or functional fragment thereof of the present invention; ii) a transmembrane domain; and iii) an intracellular signlaing domain. In addition, it provides a chimeric antigen receptor (CAR) protein comprising; i) an antibody or a functional fragment thereof that specifically binds to the extracellular second loop (ECL-2) of claudin 3; ii) a transmembrane domain; and iii) an intracellular signlaing domain.

An embodiment according to still another aspect of the present invention provides a polynucleotide encoding the chimeric antigen receptor (CAR) protein, a recombinant vector comprising the same, and a cell (especially, an immune cell) transformed with the vector.

An embodiment according to still further aspect of the present invention provides the use of the antibody or functional fragment thereof for preparing an agent for detection of claudin 3, an agent for diagnosis of cancer, an agent for imaging cancer, and an agent for drug delivery specific to cancer cells, respectively.

An embodiment according to still further aspect of the present invention provides a method for specific detection of claudin 3, a method for diagnosing cancer, a cancer imaging method, and a method for drug delivery specific to cancer cells, comprising administering an effective amount of a composition comprising the antibody or functional fragment thereof as an active ingredient to a subject in need thereof, respectively.

An embodiment according to still further aspect of the present invention provides use of the antibody-drug conjugate, in which the antibody or functional fragment thereof is bound to a drug for preparing an agent, for preventing and treating cancer, resectively.

An embodiment according to still further aspect of the present invention provides a method for preventing and treating cancer, the method comprising administering an effective amount of a composition comprising an antibody-drug conjugate, in which the antibody or functional fragment thereof is bound to a drug, as an active ingredient to a subject in need thereof.

An embodiment according to still further aspect of the present invention provides use of an antibody or a functional fragment thereof that specifically binds to the extracellular second loop (ECL-2) of claudin 3 for preparing an agent of intracellular drug delivery.

An embodiment according to still further aspect of the present invention provides a method for intracellular drug delivery comprising administering an effective amount of a composition comprising an antibody or a functional fragment thereof that specifically binds to the extracellular second loop (ECL-2) of claudin 3 as an active ingredient to a subject in need thereof.

An embodiment according to still further aspect of the present invention provides use of a functional fragment of an antibody that specifically binds to the extracellular second loop (ECL-2) of claudin 3 for preparing an agent for preventing and treating cancer; and an antibody-drug polymer to which a drug is bound.

An embodiment according to still further aspect of the present invention provides a method for treating cancer, comprising administering an effective amount of a composition comprising, as an active ingredient, an antibody or a functional fragment thereof that specifically binds to the extracellular second loop (ECL-2) of claudin 3; and a drug bound thereto to a subject in need thereof.

Hereinafter, the present invention will be described in more detail.

In the present invention, 'antibody' is also called immunoglobulin (Ig), and is a generic term for proteins that selectively bind to antigens and are involved in biological immunity. All antibodies found in nature generally consist of two pairs of light chains (LCs) and heavy chains (HCs), which are polypeptides of several domains, or are based on two pairs of HC/LC. There are five types of heavy chains constituting the antibodies of mammals defined by the Greek letters α, δ, ε, γ, and μ, and different types of antibodies, such as IgA, IgD, IgE, IgG and IgM, respectively, will be constructed depending on the type of heavy chain. There are two kinds of light chains constituting the antibody of mammals defined by λ and κ.

The heavy and light chains of an antibody are structurally divided into variable and constant regions according to amino acid sequence variability. The constant region of the heavy chain is composed of three or four heavy chain constant regions, such as CH1, CH2 and CH3 (IgA, IgD and IgG antibodies) and CH4 (IgE and IgM antibodies), depending on the type of antibody and the light chain is composed of CL, one constant region. The heavy chain variable region and light chain variable region consist of one domain of the heavy chain variable region (VH) or light chain variable region (VL), respectively. The light and heavy chains are arranged side by side with each variable and constant region connected by one covalent disulfide bond, and the heavy chains of the two molecules linked with the light chain are connected via two covalent disulfide bonds to form the whole antibody to form the whole antibody. The whole antibody specifically binds to the antigen through the variable regions of the heavy and light chains, and since the whole antibody consists of two heavy and light chain pairs (HC/LC), the whole antibody of one molecule has bivalent monospecificity that binds to the same two antigens through two variable regions.

The variable region including the site where an antibody binds to an antigen is subdivided into a framework region (FR) having low sequence variability and a complementarity determining region (CDR) which is a hypervariable region with high sequence variability. VH and VL each have three CDRs and four FRs arranged in the order of FR1-CDR1-FR2-CDR2-FR3-CDR3-FR4 in the direction from N-terminus to C-terminus. The CDRs with the highest sequence variability within the variable region of the antibody directly bind to the antigen, which is most important for the antigen specificity of the antibody.

In the present invention, the term "affinity" refers to the strength of the sum of non-covalent interactions between a single binding site of a molecule (e.g., an antibody) and its binding partner (e.g., an antigen).

Unless otherwise indicated, as used herein, "binding affinity" refers to intrinsic binding affinity that reflects a 1:1 interaction between members of a binding pair (e.g., antibody and antigen). The affinity of a molecule X for its partner Y can generally be expressed as the dissociation constant (Kd). In the present invention, the "affinity" of the antibody is expressed as Kd, which means the equilibrium dissociation constant of the antibody-antigen interaction as described above. The larger the Kd value for antibody binding to an antigen, the weaker the binding affinity to a specific antigen. The Kd or affinity may be measured by conventional methods known in the art, and for example, a measurement device such as Surface Plasmon Resonance or Ligand Tracer Green may be used.

In the present invention, 'Claudin 3 (also referred to as CLDN3)' is a protein belonging to the claudin family, and exists in a portion where tight junctions occur, and it is present in the area where tight junctions occur and plays a unique role in removing the space between cells in tight junctions.

Tight junctions are rigid structures that connect adjacent cell membranes in tissues of organisms such as animals. Claudin 3 is a structural protein that regulates the intercellular permeability of small solutes such as ions. Claudin 3 is a protein with four transmembrane regions, and has a structure that exposes two peptide loops to the outside of the cell. Among the two peptide loops, the loop of the amino acid region closer to the N-terminus than in the entire protein sequence of Claudin 3 is referred to as the first extracellular loop (represented as ECL-1 or EL1 in the present invention), and the other loop is referred to in the present invention as an extracellular second loop (in the present invention, referred to as ECL-2 or EL2). Preferably, the extracellular first loop is a region containing amino acids 27 to 80 of the claudin 3 protein amino acid sequence, and the second extracellular loop is a region containing amino acids 144 to 159 of the claudin 3 protein amino acid sequence (SEQ ID NO: 2).

Claudin 3 is known to function as a toxin receptor for *Clostridium perfringens* enterotoxin (CPE). CPE binds to Claudin 3 and Claudin 4 and then forms a large complex that causes cell necrosis, creating voids in the cell membrane.

On the other hand, the extracellular domains of claudin proteins are involved in the formation of TJ (close junction). In a normal confluent epithelial cell monolayer, claudin3 is believed to be present in the TJ strand at the apical site of the lateral membrane. Dysregulation of the mitotic spindle during epithelial tumor formation and out-of-plane differentiation in tumor cells is presumed to induce an abnormal location of the TJ component on the cell surface (Saeki R, et al., Potency of claudin-targeting as antitumor therapy Mol Cell Pharmacol. 2010; 2:47-51.). In this regard, the Claudin 3 protein has been reported to increase the degree of exposure in many cancerous tissues such as ovarian cancer, prostate cancer, breast cancer, uterine cancer, liver cancer, lung cancer, pancreatic cancer, gastric cancer, bladder cancer and colon cancer. The Swedish Human Protein Atlas (HPA) website (http://www.proteinatlas.org/) is available as a reference for the Claudin 3 expression profile for disease. The expression of Claudin 3 and Claudin 4 is particularly high in chemotherapy-resistant and/or recurrent uterine cancer, which is known to have the highest mortality rate among gynecological cancers in the United States. However, there is still a limit to specifically detecting claudin 3 exposed in a tumor state.

In the present invention, if claudin 3 is known as claudin 3 in the art, its specific biological origin and sequence may not be particularly limited. For instance, claudin 3 of the present invention includes: a sequence derived from a mouse (*Mus musculus*) and known as NCBI (Genbank) Accession No, etc., Q9Z0G9, a sequence derived from a rat (*Rattus norvegicus*) and known as NCBI (Genbank) Accession No. Q63400, etc., a sequence derived from chicken (*Gallus gallus*) and known as NCBI (Genbank) Accession No. Q98SR2, etc., a sequence derived from dog (*Canis lupus familiaris*) and known as NCBI (Genbank) Accession No. Q95KM5, etc., a sequence derived from a monkey (*Macaca mulatta*) and known as UniProtKB Entry. F6RQF6, etc., and a sequence derived from human (*Homo sapiens*) and known as NCBI (Genbank) Accession No. 015551, etc. (see SEQ ID NO: 1).

And as an example of such an antibody and its functional fragment, the antibody having a unique CDR sequence provided by the present invention has a remarkable ADCC (Antibody dependent cell cytotoxicity) effect on claudin 3 expressing cells, and has an anticancer effect by itself. In addition, it is excellent in the ability to specifically target only claudin 3 without cross-reactivity with other claudin families, exhibits very excellent binding ability (affinity) compared to the known claudin 3 antibody. It was also confirmed that it has the ability to internalize cells, so that it has excellent functions as a diagnosis, imaging and drug delivery system for cancer. In particular, the antibodies and functional fragments thereof of the present invention specifically adhere to the ECL-2 region of claudin 3, and thus claudin 3 forms an incomplete junction unlike normal tissues that are not exposed to the surface. The antibody of the present invention (or a functional fragment thereof) is selectively accessible, and this ability significantly reduces the toxicity problem of anticancer drugs against normal cells, and is of greater technical significance.

Specifically, the present invention provides an antibody or a functional fragment thereof comprising a heavy chain variable region and a light chain variable region, comprising the following CDR sequences:

a heavy chain variable region comprising a heavy chain complementarity determining region 1 (VH-CDR1) comprising an amino acid sequence defined by SEQ ID NO: 3, a heavy chain complementarity determining region 2 (VH-CDR2) comprising an amino acid sequence defined by SEQ ID NO: 4, and a heavy chain complementarity determining region 3 (VH-CDR3)

comprising an amino acid sequence defined by SEQ ID NO: 5; and a light chain variable region comprising a light chain complementarity determining region 1 (VL-CDR1) comprising an amino acid sequence defined by SEQ ID NO: 6, a light chain complementarity determining region 2 (VL-CDR2) comprising an amino acid sequence defined by SEQ ID NO: 7, and a light chain complementarity determining region 3 (VL-CDR3) comprising an amino acid sequence defined by SEQ ID NO: 8.

The present invention also provides an antibody or a functional fragment thereof comprising a heavy chain variable region and a light chain variable region, comprising the following CDR sequences:

heavy chain complementarity determining region 1 (VH-CDR1) comprising the amino acid sequence defined by SEQ ID NO: 18, heavy chain complementarity determining region 2 (VH-CDR2) comprising the amino acid sequence defined by SEQ ID NO: 19, and a heavy chain variable region comprising a heavy chain complementarity determining region 3 (VH-CDR3) comprising an amino acid sequence defined by SEQ ID NO 20; and light chain complementarity determining region 1 (VL-CDR1) comprising the amino acid sequence defined by SEQ ID NO: 21, light chain complementarity determining region 2 (VL-CDR2) comprising the amino acid sequence defined by SEQ ID NO: 22, and a light chain variable region comprising a light chain complementarity determining region 3 (VL-CDR3) comprising an amino acid sequence defined by SEQ ID NO: 23.

The type of antibody according to the present invention is not limited as long as it has a combination of the aforementioned CDRs. Specifically, it may be selected from the group consisting of IgG, IgA, IgM, IgE and IgD, and particularly preferably an IgG antibody. The IgG as its subtype includes, but is not limited to, IgG1, IgG2, IgG3, IgG4, and the like. In addition, it may be a monoclonal antibody derived from one B cell, or a polyclonal antibody derived from multiple B cells, but it is preferable that the antibody is a monoclonal antibody that is a group of antibodies whose heavy and light chain amino acid sequences are substantially the same. In addition, the antibody or fragment thereof of the present invention may be conjugated to an enzyme, a fluorescent substance, a radioactive substance, and a protein, but is not limited thereto.

The antibody of the present invention may be derived from any animal including mammals including humans, birds, and the like, preferably derived from humans, or of a species different from that of a human-derived antibody. It may be a chimeric antibody comprising a portion of an antibody derived from an animal.

In the present invention, the functional fragment of the antibody refers to a fragment that maintains the antigen-specific binding ability of the entire antibody, and specifically, it may be in the form of Fab, F(ab'), F(ab')2, Fv, scFv, a diabody or dsFv.

Fab (fragment antigen-binding) is an antigen-binding fragment of an antibody, and consists of one variable domain and a constant domain of each of the heavy and light chains. F(ab')2 is a fragment produced by hydrolyzing an antibody with pepsin and two Fabs are linked by a disulfide bond at a heavy chain hinge. F(ab') is a monomeric antibody fragment in which a heavy chain hinge is added to a Fab separated by reducing the disulfide bond of the F(ab')2 fragment. Fv (variable fragment) is an antibody fragment composed only of the variable regions of each of the heavy and light chains. A single chain variable fragment (scFv) is a recombinant antibody fragment in which a heavy chain variable region (VH) and a light chain variable region (VL) are connected by a flexible peptide linker. A diabody refers to a fragment in which the VH and VL of scFv are connected by a very short linker, so that they cannot be bonded to each other and form a dimer by bonding with the VL and VH of another scFv of the same type, respectively. dsFv refers to a polypeptide obtained by substituting a cysteine residue for one of the amino acid residues of VH and VL through an S—S bond between the cysteine residues. Amino acid residues substituted with cysteine residues can be selected based on prediction of the conformational structure of the antibody according to the method described by Reiter et al. (Protein Engineering, 7, 697 (1994)).

The antibody or functional fragment thereof of the present invention specifically binds to claudin 3, and in particular, it is characterized by being internalized inside the cell by specifically attaching to the extracellular loop 2 (ECL-2) of claudin 3 with very high affinity.

The specific biological origin of claudin 3 is not particularly limited as long as it is known in the art as claudin 3, and includes, for example, those derived from mice, humans, rats, chickens, dogs or monkeys as described above. Preferably, it may mean those derived from human, and ECL-2 of human claudin 3 preferably includes an amino acid sequence defined by SEQ ID NO: 2.

In an embodiment of the present invention, it was confirmed that the antibody of the present invention has no cross-reactivity with other claudin family having a high phylogenetic relationship with claudin 3, and thus it is proved that the binding specificity of the antibody of the present invention is very excellent. This high level of binding specificity is very meaningful in that information with high accuracy can be provided by detecting claudin 3 (especially, human claudin 3) and using it for diagnosis and imaging of specific diseases (especially, diseases characterized by abnormal (over)expression of claudin 3).

Accordingly, the present invention provides a composition and kit for detecting claudin 3 comprising the antibody or functional fragment thereof as an active ingredient. In addition, the present invention provides a method for specifically detecting claudin 3, the method comprising: (1) contacting the antibody or functional fragment thereof of the present invention with a sample; and (2) detecting the antibody or functional fragment thereof.

In addition, the present invention provides a composition and a kit for detecting claudin 3 consisting of the antibody or functional fragment thereof.

In addition, the present invention provides a composition and kit for detecting claudin 3 consisting essentially of the antibody or functional fragment thereof.

The antibody or functional fragment thereof of the present invention may be provided in a labeled state to facilitate identification for binding with claudin 3, detection and quantification of claudin 3. That is, it can be provided by linking to a detectable label (eg, covalently bonded or crosslinked). The detectable label includes, but not limited thereto, chromogenic enzymes (e.g. peroxidase, alkaline phosphatase), radioactive isotopes (e.g., $^{18}F$, $^{123}I$, $^{124}I$, $^{125}I$, $^{32}P$, $^{35}S$, $^{67}Ga$), chromophore, luminescent material or fluorescent material (e.g., FITC, RITC, fluorescent protein (GFP); EGFP (Enhanced Green Fluorescent Protein), RFP (Red Fluorescent Protein)); DsRed (*Discosoma* sp. red fluorescent protein); CFP (Cyan Fluorescent Protein), CGFP (Cyan Green Fluorescent Protein), YFP (Yellow Fluorescent Protein), Cy3, Cy5 and Cy7.5), magnetic resonance imaging materials (e.g., Gadolinium (Gd, gadolinium), super paramagnetic particles)) or ultrasuper paramagnetic particles).

The antibody or functional fragment thereof of the present invention may be provided as a detection kit or a diagnostic kit for performing a diagnostic analysis, and in this case, with reagents packaged in a predetermined amount together with an instruction manual. When the antibody is labeled with an enzyme, the kit may contain a cofactor required by the enzyme as a substrate precursor providing a substrate and a chromophore or a fluorophore. In addition, other additives such as stabilizers and buffers (e.g., blocking buffer or lysis buffer) may be included. The relative amounts of various reagents can be varied widely to provide a concentration in solution of the reagent that sufficiently optimizes the sensitivity of the assay.

The reagents may be provided as a generally lyophilized, dry powder containing excipients that will provide a reagent solution having an appropriate concentration upon dissolution.

The kit includes Western blot analysis, ELISA (enzyme-linked immunosorbent assay), radioimmunoassay, radioactive immunodiffusion method, octeroni immune diffusion method, rocket immunoelectrophoresis, tissue immunostaining, immunoprecipitation assay, complement fixation assay, Flow cytometry (FACS) and protein chip analysis, and the reagents, auxiliary substances, containers, and solid supports provided together according to each analysis method are well known in the art.

According to the claudin 3 specific detection method, one of ordinary skill in the art can measure the presence or absence and concentration of claudin 3 protein present (or included) in a sample. As used herein, detection includes quantitative and/or qualitative analysis, and includes detection of presence and absence and concentration measurement, and such methods are known in the art, and those skilled in the art will be able to select an appropriate method for the practice of the present application.

Prior to the step (1), a person skilled in the art may appropriately select a known method for detecting a protein using an antibody or a functional fragment thereof, and prepare a sample suitable for the selected method.

In addition, samples may be cells or tissues, whole blood (blood), serum, plasma, saliva, cerebrospinal fluid, etc. obtained by biopsy collected from a subject to be diagnosed for a disease (e.g., cancer) characterized by abnormal (over) expression of claudin 3, but is not limited thereto.

The method of detecting a protein using the antibody includes, for example, Western blot, immunoblot, dot blot, immunohistochemical staining, enzyme immunoassay (ELISA), radioimmunoassay, competitive binding analysis, immunoprecipitation, etc., but is not limited thereto. For example, for immunohistochemical staining, pre-treatment such as fixing and blocking sections of cells or tissues may be performed.

Next, in step (1), the antibody or functional fragment thereof according to the present invention is brought into contact with the sample prepared as described above. An antigen (claudin 3)-antibody complex is formed by the contact.

In step (2), the presence or absence of claudin 3 protein in the sample and its level is measured by detecting the antigen-antibody complex generated in the sample. As described above, the antibody or functional fragment thereof of the present invention used for detection may be provided in a labeled state, and in this case, the label can be detected immediately. Otherwise, a separately labeled secondary antibody can be used. The secondary antibody is an antibody that binds to the Fc region of a primary antibody (in this case, an antibody or a functional fragment thereof of the present invention), and the use of such secondary antibodies is well known in the art.

The detection method according to the label is widely known in the art, but may be performed, for example, by the following method. If a fluorescent substance is used as a detectable label, immunofluorescence staining can be used. For example, after reacting with the peptide of the present invention labeled with a fluorescent substance with a sample and removing unbound or non-specific binding products, fluorescence by the peptide can be observed under a fluorescence microscope. In addition, when enzymes (e.g., luciferase, peroxidase, galactosidase, etc.) are used as detectable labels, absorbance is measured by the color reaction of the substrate through enzymatic reaction, and in the case of radioactive substances, it can be performed by measuring the amount of radiation emitted (for example, scintillation counting measurement). In addition, the antibody or fragment thereof according to the present invention is prepared in a form conjugated to biotin, and can be detected by reacting with appropriately labeled streptavidin. In addition, the detected result may be imaged according to a known imaging method according to the detection label.

Accordingly, the antibody or functional fragment thereof of the present invention can be used for diagnosis and imaging diseases characterized by (over)expression of claudin 3. As a disease possible through diagnosis and imaging in the present invention, as long as it is known in the art to accompany abnormal expression (especially, overexpression) of claudin 3, the type is not particularly limited, but may preferably target cancer. Accordingly, the present invention provides a composition for diagnosis of cancer and a composition for imaging cancer comprising the antibody of the present invention or a functional fragment thereof as an active ingredient.

It also provides a composition for diagnosis of cancer and a composition for imaging cancer, consisting of the antibody of the present invention or a functional fragment thereof.

In addition, there is provided a composition for diagnosis of cancer and a composition for imaging cancer, consisting essentially of the antibody of or a functional fragment thereof the present invention.

In the present application, the type of cancer (tumor) is not particularly limited, but may preferably be a type of cancer overexpressing claudin 3 compared to a normal state, more preferably an epithelial cancer, and specific examples include, but are not limited to, ovarian cancer, colon cancer, bladder cancer, lung cancer, liver cancer, stomach cancer, esophageal cancer, breast cancer, prostate cancer, pancreatic cancer, uterine cancer, cervical cancer, or melanoma.

In addition, the antibody or fragment thereof of the present invention has very high binding specificity for claudin 3 as described above, and is characterized by being internalized into cells after binding to claudin 3 (especially, ECL-2). This ability to enter cells provides a great advantage in the development of antibody-drug conjugates (ADCs), and it is known that in order for ADCs to exhibit excellent drug efficacy, ADCs need to enter cells (internalization, internalization).

In the present invention, the internalization means that the cells enter (permeate) the inside, and the type or kind to be internalized is not particularly limited, but for example, it may be endocytosis.

Accordingly, the present invention provides a composition for drug delivery specific to cancer cells comprising the antibody or functional fragment thereof of the present invention described above as an active ingredient.

In addition, it provides a composition for drug delivery specific to cancer cells consisting of the antibody or functional fragment thereof of the present invention described above.

In addition, it provides a composition for drug delivery specific to cancer cells consisting essentially of the antibody or functional fragment thereof of the present invention described above.

Specifically, the present invention provides an antibody-drug conjugate in which a drug is bound to the above-described antibody or functional fragment thereof. In addition, it provides a composition for preventing and treating cancer comprising the antibody or functional fragment thereof and a drug bound thereto as an active ingredient.

In the present invention, the term "antibody-drug conjugate (ADC)" refers to a conjugate in which an antibody (or a functional fragment thereof) of the present invention and a drug are linked, and may also be referred to as an immunoconjugate. The antibody-drug conjugate can be prepared using various methods known in the art.

The antibody-drug conjugate may be one in which two molecules are directly bonded, or indirectly two molecules are bonded by any means such as a linker. The linker may be a non-cleavable linker or a cleavable linker. In general, it is known that the ADC is ideally designed to be indirectly bound by means such as a linker, and then the drug can be cleaved inside the targeted cells. The linker can be cleaved by a cleaving agent present in the intracellular environment, for example, lysosomes or endosomes, and may be a peptide linker cleavable by a cleaving agent for example, intracellular peptidase or protease enzymes (e.g., proteases of lysosome or endosome). In general, the peptide linker has a length of at least 2 or more amino acids. For example, the cleavable linker is pH sensitive and may be sensitive to hydrolysis at a specific pH value. In general, it is indicated that the pH sensitive linker can be hydrolyzed under acidic conditions. For example, acid labile linkers that can be hydrolyzed in lysosomes may be, for example, hydrazone, semicarbazone, thiosemicarbazone, cis-aconitic amide, orthoester, acetal, and ketal. As another example, the linker may be cleaved under reducing conditions, for example, a disulfide linker may correspond thereto. Various disulfide bonds can be formed using SATA (N-succinimidyl-S-acetyl-thioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(2-pyridyl-dithio) toluene).

The drug and/or drug-linker may be randomly conjugated through lysine of an antibody, or may be conjugated through a cysteine exposed when a disulfide bond chain is reduced. In some cases, a linker-drug may be bonded through a genetically engineered tag, for example, a cysteine present in a peptide or protein. The peptide or protein has a deletion at the carboxy end of the peptide or protein, or has an addition through a covalent bond of a spacer unit to the carboxy (C) end of the peptide or protein.

In the present invention, the term "drug" may increase the efficiency of the therapeutic antibody itself by binding to the antibody of the present invention, or increase the half-life in the blood of the antibody, or reach a position targeted by the antibody, and includes without limitation substances that can be used for the treatment of diseases by reaching the target position of the antibody and killing cancer in the target. The examples include cytotoxic drugs, toxins, cytokines, chemokines, antibiotics, enzymes such as nucleases, radionuclides, photosensitizers, photothermal nanomaterials, nanoparticles and micelles, but are not limited thereto.

In the present invention, the drug may be directly linked (bound) to an antibody, or indirectly linked by a known method. In addition, the drug bound to the antibody may be applied in a specific supported form of the drug (e.g., all forms supported on micelles, nanoparticles, liposomes, or dendrimers).

The cytotoxic drug refers to a drug that can be used for the treatment of a disease. For example, as a drug (anticancer agent) having anticancer activity, there are microtubulin structure formation inhibitors, meiosis inhibitors, topoisomerase inhibitors or DNA intercalators. The cytotoxic drugs include maytansinoid, auristatin, dolastatin, trichothecene, CC-1065 drug (NSC 298223), calicheamicin, enediynes, taxane, anthracycline, methotrexate, adriamycin, vindesine, vinca alkaloid, doxorubicin, melphalan, mitomycin C, chlorambucil, daunorubicin, daunomycin, etoposide, teniposide, carminomycin, aminopterin, dactinomycin, bleomycin, esperamicin, 5-fluorouracil, melphalan, nitrogen mustar(mechlorethamine HCL), cis-platinum and its analogs, cisplatin, CPT-11, docetaxel, Monomethyl auristatin E, Monomethyl auristatin F, or emtansine, DM, but are not limited thereto.

In the present invention, the term "toxin" refers to a drug having toxicity produced by an organism, and the type is not particularly limited, but includes phytotoxin, animal toxin, extrabacterial toxin or bacterial toxin.

As described above, the antibody of the present invention not only has very high binding specificity for claudin 3, but also has a remarkable cytotoxic effect by ADCC (Antibody dependent cell cytotoxicity) after the antibody itself binds to claudin 3.

This is well shown in one embodiment of the pecification of the present invention. Therefore, the present invention provides a composition for preventing and treating cancer comprising the antibody of the present invention as an active ingredient.

In addition, it provides a composition for the prevention and treatment of cancer consisting of the antibody of the present invention.

In addition, it provides a composition for the prevention and treatment of cancer consisting essentially of the antibody of the present invention.

Antibody-dependent cell-mediated cytotoxicity (ADCC) is known as one of the mechanisms of cancer cell death by natural killer cells.

NK cells express CD16, a receptor for the Fc of immunoglobulin G (IgG), and through this receptor, other forms of MHC non-limiting killing can be performed. That is, ADCC of NK cells depends on the presence of an antibody that recognizes the target cell. When the antibody binds to an antigen, the Fc region of the antibody is exposed, and when the exposed Fc region binds to the receptor of NK cells to form a bridge, cytotoxic substances are released from the NK cells by signal transduction caused by receptor binding, resulting in injury to the target cells.

As described above, since the antibody of the present invention itself has an anticancer effect, it exhibits a remarkable synergistic effect when the antibody is provided together with an anticancer active drug (especially in the form of ADC).

The present invention also provides a polynucleotide encoding the antibody or functional fragment thereof.

The polynucleotide encoding the antibody or functional fragment thereof is not particularly limited in base combination as long as it can encode the antibody or fragment thereof having the above-described CDR configuration.

When an amino acid sequence is identified, techniques for producing a polynucleotide encoding the amino acid sequence based on codon information known in the art are well known in the art.

The polynucleotide may be provided as a single-stranded or double-stranded nucleic acid molecule including all DNA, cDNA and RNA sequences.

In addition, the present invention provides a recombinant expression vector comprising a polynucleotide encoding the antibody or fragment thereof according to the present invention.

In the present invention, 'recombinant' can be used interchangeably with 'genetic manipulation', and refers to the manufacture of a gene in a form that does not exist in the natural state by using molecular cloning experimental techniques such as modifying, cutting, and linking genes.

In the present invention, 'expression' means that a protein or nucleic acid is produced in a cell.

In the present invention, the 'recombinant expression vector' is a vector capable of expressing a protein or nucleic acid (RNA) of interest in a suitable host cell, and refers to a genetic construct comprising essential regulatory elements operably linked so that a polynucleotide (gene) insert can be expressed. 'Operably linked' refers to a functional link between a nucleic acid expression control sequence and a nucleic acid sequence encoding a protein or RNA of interest to perform a general function, and means that the gene is linked to be expressed by an expression control sequence. The operative linkage with the recombinant vector can be prepared using gene recombination techniques well known in the art, and site-specific DNA cleavage and linkage use enzymes generally known in the art. The "expression control sequence" refers to a DNA sequence that controls the expression of a polynucleotide sequence operably linked in a specific host cell. Such regulatory sequences include promoters for carrying out transcription, any operator sequence for regulating transcription, sequences encoding suitable mRNA ribosome binding sites, sequences regulating the termination of transcription and translation, initiation codon, stop codon, polyadenylation signals and enhancers. The promoter of the vector may be constitutive or inducible. The operably linked gene sequence and the expression control sequence may be included in a single expression vector that includes a selection marker and/or a replication origin for selecting a host cell containing the vector. In addition, the expression vector includes a signal sequence or a leader sequence for membrane targeting or secretion as needed, and can be prepared in various ways according to the purpose.

Signal sequences may be used PhoA signal sequence and OmpA signal sequence when the host is *Escherichia* bacteria, α-amylase signal sequence and subtilisin signal sequence when the host is *Bacillus* bacteria, MFα signal sequence and SUC2 signal sequence when the host is yeast, an insulin signal sequence, an α-interferon signal sequence, an antibody molecule signal sequence when the host is an animal cell, but are not limited thereto.

The type of the recombinant expression vector of the present invention is not particularly limited as long as it is a vector commonly used in the field of cloning, and examples thereof include, but are not limited to, a plasmid vector, a cosmid vector, a bacteriophage vector, and a viral vector. The plasmids include *E. coli*-derived plasmids (pBR322, pBR325, pUC118 and pUC119, pET-22b(+)), *Bacillus subtilis*-derived plasmids (pUB110 and pTP5), and yeast-derived plasmids (YEp13, YEp24 and YCp50). As the virus, animal viruses such as retrovirus, adenovirus or vaccinia virus, and insect virus such as Baculovirus may be used, and pcDNA may be used.

In the present invention, the recombinant vector comprises a polynucleotide encoding a light chain of an antibody or a functional fragment thereof; A polynucleotide encoding a heavy chain or a functional fragment thereof may be provided in the form of simultaneously including (inserted) in one vector, or may be provided by including (inserting) each in two (including different types) of vectors.

In addition, the present invention provides a transformed cell with a recombinant expression vector comprising a polynucleotide encoding the antibody or functional fragment thereof according to the present invention.

In the present invention, the term host cell refers to a prokaryotic or eukaryotic cell comprising heterologous DNA introduced into the cell by any means (Examples: electric shock method, calcium phosphatase precipitation method, microinjection method, transformation method, virus infection, etc.).

The type of (host) cell of the present invention is not particularly limited as long as it can be used to express a polynucleotide encoding an antibody or fragment thereof contained in the recombinant expression vector of the present invention. Transformed cells (host cells) with the recombinant expression vector according to the present invention may be prokaryotes (e.g., *E. coli*), eukaryotes (e.g., yeast or other fungi), plant cells (e.g., tobacco or tomato plant cells), animal cells (e.g., human cells, monkey cells, hamster cells, rat cells, and mouse cells), insect cells, or hybridomas derived therefrom. Preferably, it may be a cell derived from mammals including humans.

As a more specific example, prokaryotes are Gram-negative or Gram-positive organisms, e.g., Enterobacteriaceae, e.g., *Escherichia*, e.g., *E. Coli, Enterobacter, Erwinia, Klebsiella, Proteus, Salmonella*, e.g., *Salmonella typhimurium, Serratia*, e.g., *Serratia marcescans*, and *Shigella*, and *B. subtilis* and *B. licheniformis, Pseudomonas*, e.g., *P. aeruginosa* and *Streptomyces* are included. The cells of the present invention may be not particularly limited as long as they are capable of expressing the vector of the present invention, preferably *E. Coli*, but are not limited thereto, such as *E. Coli* ER2537, *E. Coli* B, *E. Coli* X1776 (ATCC 31,537), *E. Coli* W3110 (ATCC 27,325) or LacZ-expressing *E. Coli*, and more preferably *E. Coli* ER2537. As the cell of the present invention, *Saccharomyces cerevisiae* is most commonly used in eukaryotes. However, many other genera, species and strains, but not limited thereto, for example, *Schizosaccharomyces pombe, Kluyveromyces* host, e.g., *K. lactis, K. fragilis* (ATCC 12,424), *K. bulgaricus* (ATCC 16,045), *K. ickeramii* (ATCC 24,178), *K. waltii* (ATCC 56,500), *K. drosophi larum* (ATCC 36,906), *K. thermotolerans* and *K. marxianus; Yarrowia* (EP 402,226): *Pichia pastoris* (EP 183,070); *Candida; Trichoderma reesia* (EP 244,234): *Neurospora crassa; Schwanniomyces*, e.g., *Schwanniomyces occidentalis*; and filamentous Fungi, e.g., *Neurospora crassa, Penicillium, Tolypocladium* and *Aspergillus* host, e.g., *A. nidulans* and *A. niger* are available.

Meanwhile, the cell of the present invention may be an animal cell, particularly a vertebrate cell. Proliferation of vertebrate cells in culture (tissue culture) has become a routine method and techniques are widely available. Examples of useful mammalian host cells, but not limited thereto, may be monkey kidney CV1 lines transformed by SV40 (COS-7, ATCC CRL 1651), human embryonic kidney lines (293 or 293 cells subcloned from suspension culture)

[Graham et al., 1977, J Gen Virol. 36: 59]), baby hamster kidney cells (BHK, ATCC CCL10), Chinese hamster ovary cells/−DHFR" (CHO, Urlaub et al., 1980, Proc. Natl. Acad. Sci. USA 77: 4216; for example, DG44), mouse Sertoli cells (TM4, Mather, 1980, Biol. eprod. 23:243-251), monkey kidney cells (CV1 ATCC CCL 70), African green monkey kidney cells (VERO-76, ATCC CRL-1587), human cervical cancer cells (HELA, ATCC CCL 2), dog kidney cells (MDCK, ATCC CCL 34), buffalo rat hepatocytes (BRL 3A, ATCC CRL 1442), human lung cells (W138, ATCC CCL 75), human hepatocytes (Hep G2, HB 8065), mouse breast tumor (MMT 060562, ATCC CCL51), TRI cells (Mather et al., 1982, Annals NY. Acad. Sci. 383: 44-68), MRC 5 cells, FS4 cells, human liver cancer cell lines (Hep G2)-HEK 293 cells (human embryonic kidney cells) and Expi293F™ cells, preferably CHO cells, HEK 293 cells (human embryonic kidney cells) or Expi293F™ cells. Since the expression level and modification of the protein differ depending on the host cell, a person skilled in the art can select and use the most suitable host cell for the purpose. In one embodiment of the present invention, a Chinese hamster ovary (CHO)-S cells have been used.

The transformation includes any method of introducing a nucleic acid (a polynucleotide encoding an antibody or a functional fragment thereof of the present invention) into an organism, cell, tissue or organ. As known in the art, it can be carried out by selecting a suitable standard technique according to the host cell. These methods include electroporation, protoplasm fusion, calcium phosphate (CaPO4) precipitation, calcium chloride (CaCl2) precipitation, silicon carbide whiskers, sonication, *Agrobacterium*-mediated transformation, precipitation by PEG (polyethylenglycol), dextran sulfate, lipofectamine, heat shock, particle gun bombardment are included, but are not limited thereto.

The cell includes a polynucleotide encoding a light chain of an antibody or a functional fragment thereof; and a recombinant vector provided in a form in which a polynucleotide encoding a heavy chain or a functional fragment thereof is simultaneously included (inserted) in one vector may be introduced, or a plurality of recombinant vectors provided in a form in which the polynucleotides are separately included (inserted) in each of the two vectors may be introduced into one cell or a plurality of cells. Transformed cells with the recombinant expression vector according to the present invention produce the heavy chain, light chain, or functional fragment thereof of the antibody according to the present invention.

The present invention also provides a method for preprarating an antibody or functional fragment thereof which specifically binds to claudin 3 protein, the method comprising:
 (a) preparing a polypeptide comprising a light chain and a heavy chain variable region by the transformed cells (under conditions in which the polynucleotide is expressed); and
 (b) recovering the polypeptide from the cell or a culture medium in which the cell is cultured.

Step (a) is to prepare a polypeptide of the heavy chain, light chain or functional fragment of the antibody according to the present invention from the recombinant expression vector introduced into the host cell by culturing the transformed host cell. The composition of the medium for culturing the host cells, culture conditions, and culture time may be appropriately selected according to methods commonly used in the art. For example, commercially available medium, such as Ham's F10 (Sigma-Aldrich Co., St. Louis, M0), minimal essential medium (MEM, Sigma-Aldrich Co.), RPMI-1640 (Sigma-Aldrich Co.), and Dulbecco's modified Eagle's medium (DMEM, Sigma-Aldrich Co.) may be suitable for culturing cells, but are not limited thereto. Hormones and/or other growth factors, salts, buffers, nucleotides, antibiotics, trace elements and glucose or an equivalent energy source may be added to the medium if necessary.

Antibody molecules produced in host cells can be accumulated in the cytoplasm of the cell, secreted outside the cell or culture medium by an appropriate signal sequence, or targeted by periplasm. It is understood with reference to the foregoing.

In addition, it is preferable that the antibody according to the present invention is refolded to a protein and has a functional structure (conformation) using a method known in the art so as to maintain the binding specificity for claudin 3 (especially ECL-2). In addition, when producing an IgG-type antibody, the heavy and light chains can be expressed in separate cells and the heavy and light chains can be contacted in a separate step to form a complete antibody, and it is also possible to have the heavy and light chains expressed in the same cell to form a complete antibody inside the cell.

Step (b) is obtaining an antibody or fragment thereof produced in a host cell.

In consideration of the characteristics of the antibody or functional fragment polypeptide produced in the host cell, the characteristics of the host cell, the expression method or whether the polypeptide is targeted, a person skilled in the art can appropriately select and adjust the obtaining method. For example, the antibody or fragment thereof secreted into the culture medium can be recovered by a method such as obtaining a culture medium in which host cells are cultured and centrifuging to remove impurities. If necessary, cells may be lysed in a range that does not affect the functional structure of the antibody or functional fragment thereof in order to release and recover the antibody present in a specific organelle or cytoplasm inside the cell. In addition, the obtained antibody may be further subjected to a process of further removing and concentrating impurities through a method such as chromatography, filtration, or dialysis.

The pharmaceutical composition according to the present invention may contain the antibody, a functional fragment thereof of the present invention, or an ADC containing the same, or may be formulated in a suitable form with one or more pharmaceutically acceptable carriers, and it may further contain excipients or a diluent. The term 'pharmaceutically acceptable' as used herein refers to a non-toxic composition that is physiologically acceptable and does not cause allergic reactions or similar reactions such as gastrointestinal disorders and dizziness when administered to humans.

The pharmaceutically acceptable carrier may further include, for example, a carrier for oral administration or a carrier for parenteral administration.

Pharmaceutically acceptable carriers may further include, for example, carriers for oral administration or carriers for parenteral administration. The carriers for oral administration may include lactose, starch, cellulose derivatives, magnesium stearate and stearic acid. In addition, it may include various drug delivery materials used for oral administration to a peptide agent. In addition, the carriers for parenteral administration may include water, suitable oils, saline, aqueous glucose and glycols, and further include stabilizers and preservatives. Suitable stabilizers include antioxidants such as sodium hydrogen sulfite, sodium sulfite or ascorbic acid. Suitable preservatives include benzalkonium chloride, methyl- or propyl-parabens and chlorobutanol.

The pharmaceutical composition of the present invention may further include a lubricant, a humectant, a sweetener, a flavoring agent, an emulsifier and a suspension agent in addition to the above components.

Other pharmaceutically acceptable carriers and preparations may refer to all types known in the art.

The composition of the present invention can be administered to mammals including humans by any method. For example, it can be administered orally or parenterally.

Specifically, the route of administration of the composition of the present invention may be a known antibody administration method, for example, the injection or infusion by an intravenous, intraperitoneal, intracranial, subcutaneous, intramuscular, intraocular, intraarterial, cerebrospinal, or intralesional route, or the injection or infusion by the sustained release system described below. For example, the antibody of the present invention may be administered systemically or locally.

The pharmaceutical composition of the present invention may be formulated into an agent for oral or parenteral administration according to the route of administration as described above.

In the pharmaceutical composition according to the present invention, the antibody, functional fragment thereof, or ADC containing the same can be administered in various oral and parenteral formulations at the time of clinical administration. It, when formulated, may be prepared using a diluent or an excipient, such as filler, an extender, a binder, a wetting agent, a disintegrant, or a surfactant, which is normally used. Solid formulations for oral administration include a tablet, a pill, a powder, granules, a capsule, a troche, and the like. These solid formulations may be prepared by mixing at least one excipient, for example, starch, calcium carbonate, sucrose or lactose, or gelatin. In addition, lubricants, such as magnesium stearate and talc, may be used besides to the simple excipients. Liquid formulations for oral administration include a suspension, a solution for internal use, an emulsion, and syrup. Besides simple diluents that are frequently used, such as water and liquid paraffin, several excipients, for example, a wetting agent, a sweetener, an aroma, and a preservative may be contained in the liquid formulations.

Agents for parenteral administration include sterile aqueous solutions, non-aqueous solvents, suspensions, emulsions, lyophilized agents and suppositories.

The therapeutic compositions of the invention may be prepared in the form of a lyophilized cake or aqueous solution for storage after mixing any physiologically acceptable carrier, excipient or stabilizer with the antibody having the desired purity. Acceptable carriers, excipients or stabilizers are nontoxic to recipients at the dosages and concentrations employed, and include complete solutions such as phosphoric acid, citric acid and other organic acids; Antioxidants including ascorbic acid; Low molecular weight (less than about 10 residues) polypeptides; Proteins such as serum albumin, gelatin or immunoglobulins; Hydrophilic polymers such as polyvinylpyridone; Amino acids such as glycine, glutamine, asparagine, arginine or lysine; Monosaccharides, disaccharides, and other carbohydrates including glucose, mannose, or dextrins; Chelating agents such as EDTA; Sugar alcohols such as manny or sorbitan; Salt-forming counterions such as sodium; And (or) nonionic surfactants, such as tween, pluronics or polyethylene glycol (PEG).

Agents for parenteral administration may be formulated by methods known in the art in the form of injections, creams, lotions, external prepartions, oils, moisturizers, gels, aerosols and nasal inhalants. These formulations are described in formulas generally known to all pharmaceutical chemistry.

In certain embodiments, the pharmaceutical composition may be delivered by intranasal spray, inhalation and/or other aerosol delivery vehicles. Methods for direct delivery of genes, polynucleotides and peptide compositions to the lungs via intranasal aerosol spray can be referred to, for example, those described in U.S. Pat. Nos. 5,756,353 and 5,804,212.

The total effective amount of an antibody or functional fragment thereof of the present invention may be administered in a single dose, or may be administered by a fractionated treatment protocol in which multiple doses are administered for a long time. They can also vary in dosage when given as ADC. The pharmaceutical composition of the present invention may vary the content of the active ingredient (an antibody or a functional fragment thereof of the present invention) according to the extent and/or purpose of the disease, but may be repeatedly administered several times at regular intervals at an effective dose of usually 0.01 mg/kg/day-1000 mg/kg/day, preferably 0.1 mg/kg/day to 100 mg/kg/day, and more preferably 1 mg/kg/day to 20 mg/kg/day. However, the dosage of the pharmaceutical composition is determined in consideration of various factors such as the formulation method, route of administration and frequency of treatment, as well as various factors such as the patient's age, weight, health status, sex, severity of the disease, diet and excretion rate. In view of this, those of ordinary skill in the art will be able to determine the appropriate effective dosage of the compositions of the present invention. The pharmaceutical composition according to the present invention is not particularly limited to its formulation, route of administration and method of administration as long as the effect of the present invention is shown.

As described above, the antibody or functional fragment thereof of the present invention is characterized by having a unique CDR configuration as described above, and thus has excellent specificity and affinity for the claudin 3 target.

Accordingly, the antibody or functional fragment thereof of the present invention can be used to confer a targeting ability for claudin-3 to cells, particularly immune cells.

Accordingly, the present invention provides a CAR (chimeric antigen receptor) comprising the antibody or a functional fragment thereof of the present invention.

Specifically, the present invention provides a chimeric antigen receptor (CAR) protein comprising:
  i) an extracellular domain comprising the antibody or functional fragment thereof of the present invention described above;
  ii) a transmembrane domain; and
  iii) an intracellular signaling domain.

In the present invention, the term "chimeric antigen receptor (CAR)" refers to a receptor that does not exist naturally, which can have specificity for a specific antigen to an immune effector cell.

Usually, the CAR refers to a receptor used to transplant the specificity of a monoclonal antibody into T cells. The CAR is usually composed of an extracellular domain (Ectodomain), a transmembrane domain, and an intracellular domain (Ectodomain).

The (i) extracellular domain includes the antibody or functional fragment thereof of the present invention described above, and they contain an antigen-binding region. The antibody used for the CAR is preferably in the form of an antibody fragment, more preferably in the form of Fab or scFv, but is not particularly limited thereto.

In addition, the (ii) transmembrane domain of the CAR is a form linked to an extracellular domain, and may be derived from natural or synthetic ones. When derived from naturally occurring, it may be derived from a membrane-bound or membrane-permeable protein, it may be a portion derived from the membrane permeable region of various proteins such as the alpha, beta or zeta chain of T cell receptors, CD28, CD3 epsilon, CD45, CD4, CD5, CDS, CD9, CD16, CD22, CD33, CD37, CD64, CD80, CD86, CD134, CD137, CD154 or CD8, but is not limited thereto. The sequence of such a transmembrane domain can be obtained from a document known in the art, which is known about the membrane-permeable region portion of a membrane-permeable protein.

In the CAR, (iii) the intracellular signaling domain is present inside the cell as a form linked to the transmembrane domain. The intracellular signaling domain of the present invention is a region that generates or/and transmits a signal that primarily causes cell activation when an antigen binds to the antigen binding site of the CAR (i.e., the antibody or functional fragment thereof of the present invention).

The kind of the 'cell' is not particularly limited, but may preferably be an immune cell (immune effector cell). The type of the immune cell is not particularly limited as long as it is a cell known to be involved in the body's immune function in the art. For example, it includes T cells, NK (Natural Killer) cells, NKT (Natural Killer T) cells, monocytes, macrophages or dendritic cells, and it means including progenitor cells thereof.

The term 'cell activation' means that the activity of the cell is increased, and the type of such activity is not particularly limited, but may be, for example, promoting an immune response of a cell. In particular, when the cell is an immune cell, the activation may be understood to include both an increase in the number of immune cells as well as an action of promoting an immune response of the cell itself.

The intracellular signaling domain is not particularly limited to its type as long as it can transmit a signal that can bring about cell activation (especially, immune cells) when an antigen is bound to an antigen-binding site located outside the cell (antibodies or functional fragments thereof of the present invention).

Various types of intracellular signaling domains can be used, such as immunoreceptor tyrosine-based activation motif or ITAM, and the ITAM may include CD3 zeta (ξ, zeta), TCR zeta, FcR gamma, FcR beta, CD3 gamma, CD3 delta, CD3 epsilon, CDS, CD22, CD79a, CD79b, CD278, CD66d, DAP10, DAP12, FcεRI (especially γ) and combinations thereof (one or two or more), but is not limited thereto.

In addition, the CAR of the present invention may preferably further include a costimulatory domain together with an intracellular signaling domain, depending on the cell type, but is not limited thereto.

The co-stimulatory domain is a part that is included in the CAR of the present invention and plays a role of transmitting a maximum activation signal to a corresponding cell in addition to the primary signal by the intracellular signaling domain. It refers to the intracellular portion of a CAR comprising the intracellular domain of a costimulatory molecule. That is, some immune cells such as T lymphocytes and NK cells require two signals for maximum activation, namely a primary activation signal and a costimulatory signal. The CAR may also optionally include a costimulatory domain such that binding of the antigen to the extracellular domain results in the transmission of both a primary activation signal and a costimulatory signal.

The co-stimulatory molecule is a cell surface molecule, which means a molecule necessary to bring about a sufficient response of an immune cell to an antigen, and its kind is not particularly limited as long as it is known in the art. For example, it may be selected from the group consisting of a ligand specifically binding to MHC class I molecules, TNF receptor proteins, Immunoglobulin-like proteins, and cytokine receptors, integrins, SLAM proteins (signaling lymphocytic activation molecules), NK cell activating receptors, BTLA, Toll ligand receptor, OX40, CD2, CD7, CD27, CD28, CD30, CD40, CDS, ICAM-1, LFA-1(CD11a/CD18, lymphocyte function-associated antigen-1), 4-1BB(CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83, PD-1, and combinations thereof. The co-stimulatory domain may be an intracellular portion of a molecule selected from the group consisting of such co-stimulatory molecules and combinations thereof (one or two or more).

The co-stimulatory domain may be linked to the N-terminus or C-terminus of the signaling domain, and may be included within a plurality of signaling domains.

Each domain constituting the CAR may be directly linked, and also, selectively, a short oligopeptide or polypeptide linker may link the intracellular domain and the membrane-permeable domain of the CAR. Even if the linker is included in the CAR of the present invention, if it is a linker capable of inducing T cell activation through an intracellular domain when the antigen is bound to an antibody located outside the cell, it is not particularly limited to its length. For example, (G4S)3 linker, GGGGSGGGGSGGGGS (SEQ ID NO: 17), can be used.

In addition, the present invention provides a polynucleotide encoding the chimeric antigen receptor (CAR) protein, and a recombinant vector comprising the polynucleotide. The polynucleotide is not particularly limited in base combination as long as it encodes a CAR protein including the antibody or functional fragment thereof of the present invention, and may be produced by a polynucleotide synthesis technique known in the art. In addition, the vector includes a polynucleotide encoding a CAR protein, and refers to a material that can be used to deliver the polynucleotide into a cell, and reference is made to the above description of the recombinant vector.

The present invention also provides a transformed cell with a vector containing a polynucleotide encoding the CAR protein. That is, it provides a cell (CAR-expressing cell) modified to express a CAR protein comprising the antibody of the present invention or a functional fragment thereof.

The cell type is not particularly limited, and a cell type advantageous for signaling may be used depending on the origin of the domain constituting the CAR.

In the present invention, the cell modified to express the CAR protein may preferably be an immune cell.

The type of the immune cells is not particularly limited as long as the cells are known to be involved in the body's immune function in the art, but it includes, for example, T cells, NK (Natural Killer) cells, NKT (Natural Killer T) cells, monocytes, macrophages, dendritic cells, and progenitor cells thereof. Most preferably, it may be a T cell.

In the present invention, the term "T cell" refers to a lymphocyte derived from the thymus gland and plays a major role in the immunity of the cell. The T cells include $CD4^+$ T cells (helper T cells, TH cells), $CD8^+$ T cells (cytotoxic T cells, CTL), memory T cells, regulatory T cells (Treg cells), and natural killer T cells. In the present invention, the T cell into which the CAR is introduced may preferably be a $CD8^+$ T cell, but is not limited thereto.

For example, antigen-specific $CD8^+$ T cells are evaluated as the most effective immune cells for cancer immunotherapy. However, a complicated process and a long period are required to isolate antigen-specific $CD8^+$ T cells for use in cancer immunotherapy. Accordingly, a chimeric antigen receptor (CAR)-modified T cell was designed as one of the methods for mass-producing antigen-specific $CD8^+$ T cells in a short time (Porter D L et al., N Engl J Med. 0.2011; 365:725-33.). Although not limited thereto, as a general example, CAR is a signal transduction domain that causes T cell activation with the scFv of an antibody that recognizes a specific antigen, and is preferably a protein in a form in which a co-stimulatory molecule and a signal transduction domain of CD3 are combined. When the antibody part constituting the CAR recognizes a specific antigen, it induces strong T cell proliferation signaling to selectively proliferate CD8+ T cells. These proliferated cells contribute to the immunotherapy of cancer.

As such an immune cell therapeutic agent, the immune cells modified to express the CAR of the present invention specifically recognize and bind to claudin 3 (especially ECL-2 region) exposed to cancer cells compared to normal cells. Accordingly, it can be seen that it can have a cancer cell treatment effect according to the activation of immune cells. Considering that the existing CAR-modified immune cell therapy technology mainly focused on hematological cancer has made up a large number of technologies and also considering that the existing CAR technologies are highly likely to be targeted to normal cells, the present invention can specifically target only solid cancer compared to normal cells, so that side effects (especially, side effects on normal cells) are small and excellent treatment effects for solid cancer can be obtained. Therefore, the present invention can provide a pharmaceutical composition for preventing or treating cancer comprising the CAR-expressing cells of the present invention as an active ingredient.

Furthermore, the present inventors provide the above-described drug delivery use of an antibody or functional fragment thereof that specifically binds to the extracellular second loop of claudin 3 like the above-described antibody, ADC, CAR and CAR-expressing cell (especially immune cells) technology. This is understood by borrowing from the foregoing.

The present invention provides the use of the antibody or functional fragment thereof to prepare an agent for detection of claudin 3, an agent for diagnosis of cancer, an agent for imaging cancer, and an agent for drug delivery specific to cancer cells.

The present invention provides a method for specific detection of claudin 3, a method for diagnosing cancer, a cancer imaging method, and a method for drug delivery specific to cancer cells, comprising administering an effective amount of a composition comprising the antibody or functional fragment thereof as an active ingredient to a subject in need thereof.

The present invention provides the use of the antibody or the antibody or functional fragment thereof for preparing an agent for preventing and treating cancer; and an antibody-drug polymer to which a drug is bound.

The present invention provides a method for preventing and treating cancer comprising administering an effective amount of a composition comprising the antibody as an active ingredient, or the antibody or functional fragment thereof; and an antibody-drug polymer to which a drug is bound as an active ingredient to a subject in need thereof.

The present invention provides a use of an antibody or a functional fragment thereof that specifically binds to the extracellular second loop (ECL-2) of claudin 3 for preparing an agent of intracellular drug delivery.

The present invention provides a method for intracellular drug delivery comprising administering an effective amount of a composition comprising an antibody or a functional fragment thereof that specifically binds to the extracellular second loop (ECL-2) of claudin 3 as an active ingredient to a subject in need thereof.

The present invention provides a use of an antibody or a functional fragment thereof that specifically binds to the extracellular second loop (ECL-2) of claudin 3 for preparing an agent for preventing and treating cancer; and an antibody-drug polymer to which a drug is bound.

The present invention provides a method for preventing and treating cancer comprising administering an effective amount of a composition comprising the antibody or functional fragment thereof that specifically binds to the extracellular second loop (ECL-2) of claudin 3; and an antibody-drug polymer to which a drug is bound as an active ingredient to a subject in need thereof.

The 'effective amount' of the present invention refers to an amount that shows an improvement, treatment, prevention, detection, diagnosis or inhibitory effect of cancer when administered to an individual, and The 'subject' may be an animal, preferably a mammal, particularly an animal including a human, or may be a cell, tissue, organ, or the like derived from the animal. The subject may be a patient in need of treatment.

The 'treatment' of the present invention generally refers to improving the symptoms of cancer or cancer, which may include curing, substantially preventing, or improving the condition of such a disease. It includes, but is not limited to, alleviating, curing, or preventing one or most symptoms resulting from cancer.

The term 'comprising' of the present invention is used in the same way as 'containing' or 'characterized', and in the composition or method, additional component elements or methods not mentioned are not excluded. The term "consisting of" means excluding additional elements, steps, or ingredients that are not separately described. The term "essentially consisting of" is meant to include, in the scope of a composition or method, component elements or steps that do not substantially affect their basic properties in addition to the described component elements or steps.

Advantageous Effect

Antibodies and functional fragments thereof that specifically bind to ECL-2 of claudin 3 are more effective in cancer cell detection, diagnosis, imaging, and application to cancer treatment (application to ADC and CAR-expressing cells (especially immune cells)) than other cancer antigens or conventional antibodies targeting ECL-1 of claudin 3. In particular, as a specific example of this, the antibody comprising the unique CDR sequence provided by the present invention not only possesses anticancer ability by itself, but also exhibits excellent cancer cell targeting ability without cross-reactivity with other claudin families, compared with the known claudin 3 antibody. It exhibits excellent binding strength (affinity), and possesses properties such as cell internalization, and thus exhibits remarkable effects in application to the above use.

BRIEF DESCRIPTION OF THE DRAWINGS

FIG. 4b shows the sequence homology of the extracellular first loop (EL1, Extracellular $1^{st}$ loop) and the extracellular second loop region (EL2, Extracellular $2^{nd}$ loop) of CLDN4, CLDN5, CLDN6, CLDN8, CLDN9, CLDN17 and CLDN1 and mouse CLDN3 located phylogenetic close to CLDN3 (SEQ ID NOs: 24-41, respectively, from top to bottom).

FIG. 9b is a result of flow cytometry for the binding of the present invention antibody (4G3 IgG) to CHO-CLDN3 cells (positive cell line, control).

FIGS. 12a to 12e show the results of comparatively confirming the expression level of claudin 3 in various cancer cells by treating the 4G3 antibody of the present invention and performing flow cytometry.

MODE FOR CARRYING OUT INVENTION

Figure 1:
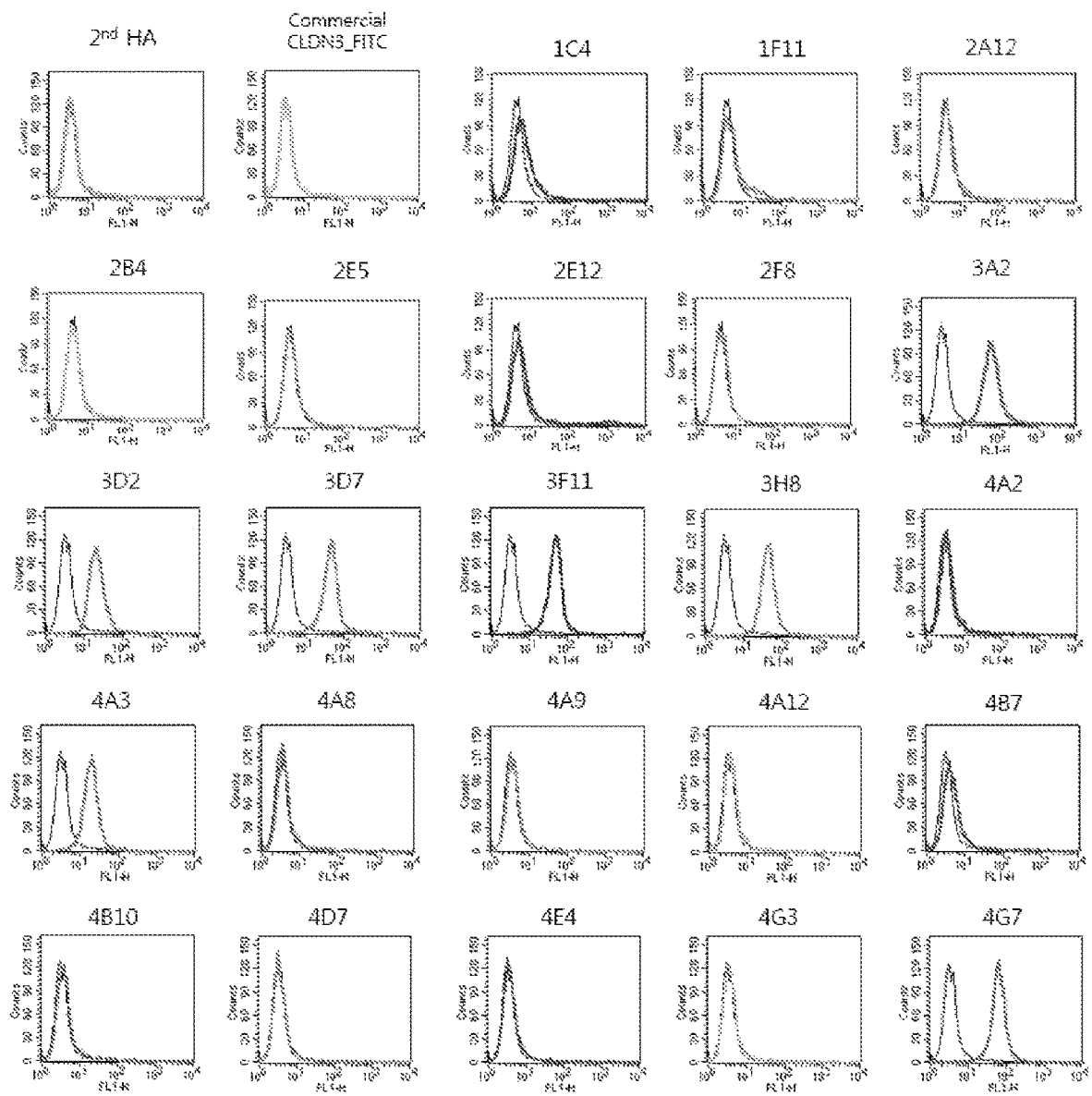
FIG. 1 is a result of a flow cytometry of binding to CHO-K1 cells (negative cell line, control) with respect to scFvs selected from CHO-CLDN3 cell line using biopanning and L-Cludin 3 cell line using ELISA.

Hereinafter, the present invention will be described in detail.

However, the following examples are merely illustrative of the present invention, and the contents of the present invention are not limited to the following examples.

Example 1: ScFv Screening Specifically Binding to Claudin 3 (CLDN3)

1-1. Antigen

As an antigen, claudin 3 was provided in the form of claudin 3 expressing cell lines and claudin 3 lipoparticles, respectively, during the screening process. CHO-K1 cell line was used to make a cell line expressing claudin 3 (NCBI reference number_O15551 (see SEQ ID NO: 1)). In order to construct a claudin 3 expression vector, the claudin 3 gene was inserted into pcDNA3.1 (invitrogen) using restriction enzymes HindIII and BamH1. The prepared claudin 3 expression vector was transfected and treated with 400 μg/ml of geneticin (g418) to select transformants. The lipoparticles exposing the claudin 3 on the surface (hereinafter, referred to as claudin 3 lipoparticles) were ordered and used by Integralmolecular (Cat. No. RR-0733A).

1-2. scFv Phage Screening

In order to screen for an antibody that specifically binds to claudin 3, a phage library display was used.

The library was a synthesized human scFv library, and for specific information on the library, see A Novel Human scFv Library with Non-Combinatorial Synthetic CDR Diversity (Bai X. et al., PLoS ONE., 10(10):e0141045 (2015)).

The scFv expressed in the scFv library was tagged with an HA tag so that it could be detected by an anti-HA FITC antibody (Genscript, A01621).

Biopanning was performed as follows using the scFv library.

First, biopanning was performed using the claudin 3 expressing CHO-K1 cell line (hereinafter referred to as CHO-CLDN3) prepared in Example 1-1. The scFv library stock was blocked with 3% FBS/PBS at room temperature. Each $1 \times 10^7$ CHO-CLDN3 cells and $1 \times 10^7$ CHO-K1 cells (negative cell line) are prepared using trypsin. CHO-K1 cells (negative cell line) are mixed with the blocking library stock, and depletion is performed at room temperature for 1 hour. After the depletion is over, the supernatant obtained by centrifugation is mixed with the antigen CHO-CLDN3 cells and reacted at room temperature for 1 hour. The cell pellet obtained by centrifugation was washed with 3% FBS/PBS, and then reacted with 100 mM TEA (triethylamine) for 5 minutes at room temperature so that only specifically bound scFv-phage could be eluted, and neutralized with pH 8.5 Tris. After the reaction, it was prepared in the form of a scFv-antigen conjugate. The prepared scFv-antigen conjugate (conugate) was added to *E. coli* TG1 cells for infection, and then incubated overnight at 37° C. in LB/ampicillin/glucose agar medium.

The *E. coli* TG1 cells were transferred to SB/Ampicillin medium and cultured until the OD600 value reached 0.5, and then $1 \times 10^{11} \sim 1 \times 10^{12}$ helper phage was added, and again at 37° C. for 1 hour. After culturing, kanamycin was added and cultured again overnight. After the overnight culture was centrifuged, the supernatant was reacted with the PEG solution at 4° C., and then centrifuged again to separate the pellet.

After dissolving the pellet in PBS, the supernatant obtained by centrifugation was obtained as a scFv library solution. This process was repeated 4 times to obtain a scFv candidate group that specifically binds to the antigen of claudin 3.

In the second method, biopanning was performed using lipoparticles. The scFv library stock was mixed with lipoparticle null (lipoparticle not containing Claudin 3), and blocking and depletion were simultaneously performed at room temperature for 1 hour with 4% skim milk. 1 ml of PBS containing claudin 3 lipoparticles was added to an immunotube and reacted at 4° C. for 16 hours to coat the inner surface of the tube. The antigen solution was decanted and washed once to remove uncoated antigen. The antigen coated on the immunotube (Cludin 3 lipoparticles) was blocked with 4% skim milk at room temperature for 1 hour. After blocking was completed, the skim milk was removed, mixed with the scFv library stock, and reacted at room temperature for 1 hour. After washing with PBS, it was reacted with 100 mM TEA for 5 minutes at room temperature so that only specifically bound scFv-phages could be eluted, and neutralized with pH 8.5 Tris to prepare a scFv-antigen conjugate form. The prepared scFv-antigen conjugate (conugate) was added to *E. coli* TG1 cells for infection, and then incubated overnight at 37° C. in LB/ampicillin/glucose agar medium. The *E. coli* TG1 cells were transferred to SB/Ampicillin medium and cultured until the OD600 value reached 0.5, and then $1 \times 10^{11} \sim 1 \times 10^{12}$ helper phage was added, and after incubation at 37° C. for another 1 hour, kanamycin was added and cultured again overnight. After the overnight culture was centrifuged, the supernatant was reacted with the PEG solution at 4° C., and then centrifuged again to separate the pellet. The pellet was dissolved in PBS and then centrifuged to obtain the supernatant as a scFv library solution. This process was repeated 4 times to obtain a scFv candidate group that specifically binds to the antigen of claudin 3.

1-3. Screening for scFv Antibodies that Specifically Bind to Claudin 3 (CLDN3)

In order to select the scFv having excellent binding ability from the scFv candidate group obtained in Example 1-2, ELISA analysis was performed on the claudin 3 expressing cell line.

The claudin 3 expressing cell line (hereinafter referred to as L-claudin 3 cells) was transfected with the claudin 3 expression vector prepared in Example 1-1 to L cells, and then 600 μg/ml of geneticin (g418) was used to select transformants. Each of the library stocks selcected at each step in Example 1-2 (screening results using a claudin 3 expressing cell line or claudin 3 lipoparticles were separately used) was cultured overnight in SB/Ampicillin/Glucose Agar medium, and then each single colony was inoculated into 200 μl of SB/Ampicillin medium. After incubation at 37° C. for 3 hours, it was mixed so that the IPTG concentration became 1 mM, and then cultured again at 30° C. overnight. When the culture was completed, the culture solution was centrifuged to separate only the cells, and then the cells were lysed using TES buffer to obtain scFv. The obtained scFv was treated on a plate in which L-Claudin 3 cells were dispensed $1 \times 10^5$ each, reacted at room temperature for 1 hour, and then a secondary antibody (anti-HA HRP, santacruz, Cat. No. sc-7392) was added and reacted for 40 minutes. When the secondary antibody reaction was completed, TMB was added to perform a color reaction and analyzed using an ELISA reader (450 nm). By comparing the ELISA analysis values, the top 23 excellent scFvs were primarily selected (1C4, 1F11, 2A12, 2B4, 2E5, 2E12, 2F8, 3A2, 3H8, 4A2, 4A3, 4B7, 4B10, 4D7, 3D2, 3D7, 3F11, 4A8, 4A9, 4A12, 4E4, 4G3, 4G7).

Figure 2:
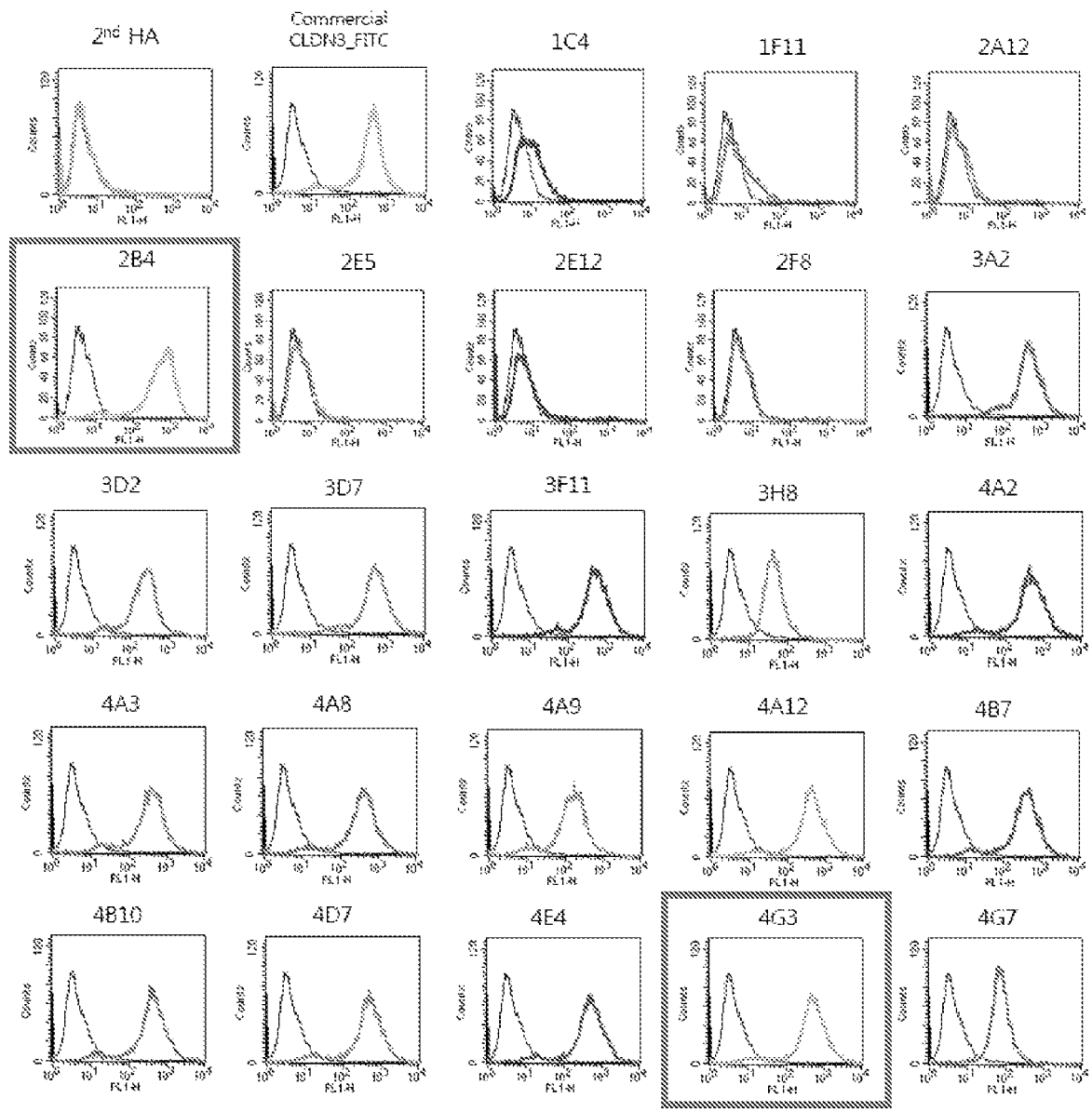
FIG. 2 is a result of flow cytometry of binding to CHO-CLDN3 cells with respect to scFvs selected from the CHO-CLDN3 cell line using biopanning and the L-Claudin 3 cell line using ELISA.

With respect to the scFv candidates selected through the ELISA, the binding to CHO-CLDN3 cells was confirmed using flow cytometry. As a control, native CHO-K1 cells were used. Cells being subcultured were separated into single cell units using trypsin and prepared in 3% in FBS/PBS. The selected scFv candidates were inoculated into 5 ml of SB/Ampicillin medium, incubated at 37° C. for 3 hours, mixed so that the IPTG concentration became 1 mM, and then cultured again at 30° C. overnight. When the culture was completed, the culture solution was centrifuged to separate only the cells, and then the cells were lysed using TES buffer to obtain scFv. CHO-K1 cells (negative cell line, control) and CHO-CLDN3 cells (experimental group) were prepared with concentration of $2 \times 10^5$ cells in 3% in FBS/PBS for each group, and then after the obtained scFv was treated, it was reacted at room temperature for 1 hour. Upon completion of the reaction, after washing with 3% in FBS/PBS, anti-HA taq FITC antibody was diluted 1:100 (diluted with 100 μl of 3% in FBS/PBS), treated with 100 ul, and reacted at room temperature for 1 hour. After completion of the reaction, it was washed and analyzed with BD FACS Calibur. At this time, commercially available anti-CLDN3 (FAB4620F, R&D systems) antibody was used as a control group. Compared to the control group (see FIG. 1), scFv candidate groups in which peak shift occurred only in the experimental group (see FIG. 2) were selected (2B4, 4A2, 4B7, 4B110, 4D7, 4A8, 4A9, 4A12, 4E4, 4G3, 4G7).

Next, the final biopanning results (data not shown) using claudin 3 lipoparticles were compared with the results of the scFv candidate group selected in the above experimental steps. Sequencing was performed on the selected scFv, and two 2B4 and 4G3 clones were obtained in an experiment on claudin 3 lipoparticles and claudin 3 expressing cell lines (CHO-CLDN3 cell line or/and L-claudin 3 cell line). The results of analyzing the amino acid sequence of 2B4 and 4G3 scFv are shown in Table 1 below.

TABLE 1

| Antibody | Heavy chain variable region | | |
|---|---|---|---|
| | CDRH1 | CDRH2 | CDRH3 |
| 2B4 | GYYWS (SEQ ID NO: 18) | TIHPGDSDTRYNPSLQG (SEQ ID NO: 19) | RQGYSLFDI (SEQ ID NO: 20) |
| 4G3 | SYAMS (SEQ ID NO: 3) | IINPSGASTSHAQRFQG (SEQ ID NO: 4) | RYGRYGSFDI (SEQ ID NO: 5) |

| Antibody | Light chain variable region | | |
|---|---|---|---|
| | CDRL1 | CDRL2 | CDRL3 |
| 2B4 | RASQSVASDLA (SEQ ID NO: 21) | AASRLQS (SEQ ID NO: 22) | QQYNSYPPT (SEQ ID NO: 23) |
| 4G3 | SGSTSNIGRNYVS (SEQ ID NO: 6) | DTSNKHF (SEQ ID NO: 7) | QSYDSSKVV (SEQ ID NO: 8) |

Example 2: Conversion and Expression of 4G3 scFv Antibody to IgG 2-1. Construction of Whole IgG Expression Vector The previously selected 4G3 scFv was converted to the form of IgG, which is a more commonly used antibody. An expression vector capable of expressing the entire IgG form was constructed based on the CDR regions of the scFv. First, a light chain variable region and a heavy chain variable region of scFv were obtained through PCR, respectively, and the primers shown in Table 2 below were used for 4G3. The light chain variable region sequence is cloned into pOptiVec (Invitrogen), an expression vector into which a light chain constant region sequence is inserted, and the heavy chain variable region sequence was cloned into pcDNA 3.3 (Invitrogen), an expression vector into which a heavy chain constant region was inserted, respectively. The light chain and heavy chain constant regions are expressed together with the light chain variable region and the heavy chain variable region of the scFv cloned from the vector, and as a result, a whole IgG antibody including the CDR regions of the scFv is produced.

TABLE 2

| variable region | Primer sequence | SEQ ID NO: |
|---|---|---|
| Light chain F | 5'-ATTCGATCGATATGGAGACAGACACACT CCTG CTATGGGTACTGCTGCTCTGGGTTCCAG GTTCCA CGTGGCAGAGCGTGCTGACCCAGCCT-3' | 9 |
| Light chain R | 5'-AGCCACCGTACGCAGCACGGTCAGCTT GGTACC-3' | 10 |
| Heavy chain F | 5'-ATTCGATCGATATGGAGACAGACACACT CCTG CTATGGGTACTGCTGCTCTGGGTTCCAG GTTCCACGTGGGAAGTGCAGCTGCTGG AAAGT-3' | 11 |
| Heavy chain R | 5'-CTTGGTGCTAGCGCTGCTCACGGTCACCA GAGT-3' | 12 |

2-2. Construction of CHO-S Cell Line (Pool) Expressing Whole IgG Antibody

CHO-S cells (Life Technologies Inc.) were used to prepare cell lines expressing 4G3 IgG antibody, respectively. Codon optimization was performed with *Cricetulus griseus* species for the gene sequences encoding the heavy and light chains obtained in the Example 2-1, and these sequences were cloned into Freedom® pCHO1.0Vector, and CHO-S cells were transduced with a transfection reagent (FreeStyle™ MAX Reagent; Life Technologies Inc.). To select the antibody-expressing cell line after transduction, it was selected through two steps using puromycin and MTX (methotrexate). Specifically, the first selection was performed with 10 ug/ml puromycin and 100 nM MTX, or 20 ug/ml puromycin and 200 nM MTX, and the second process was performed when the cell viability was within the standard. Secondary screening is performed with 30 ug/ml puromycin and 500 nM MTX, or 50 ug/ml puromycin and 1000 nM MTX. When the final cell viability standard is reached, the secondary screening is terminated and the group with high expression level is selected through SFB (Simple Fed Batch).

2-3. Total IgG Antibody Production and Purification Each antibody-producing cell line prepared in 2-2 was cultured in CD FortiCHO™ medium with 8% $CO_2$, 37° C., 100-120 rpm conditions for a total of 14 days, adding 4 g/L, 4 g/L, and 6 g/L of glucose respectively on the 3rd, 5th, and 7th days. After completion of the culture, the culture solution was centrifuged with an ultra-centrifuge at 6000 g, and the supernatant was filtered using a 0.2 um filter. Protein A resin (Mabselect SuRe, 11-0026-01 AD, GE Healthcare Life Sciences) was used for purification, and an equilibrium buffer (20 mM Sodium Phosphate, 150 mM NaCl, pH7.2), washing buffer (35 mM Sodium Phosphate, 500 mM NaCl, pH7.2), an elution buffer (0.1M Sodium Citrate, pH3.6) was used. Using AKTA™ avant, it was purified by using the equilibrium buffer at 2 times the column volume, the washing buffer at 5 times the column volume, and the elution buffer at 5 times the column volume. At the time of elution, a pH 8.0 Tris-HCl solution was added to ⅕ of the column volumne for neutralization. After converting the buffer into PBS twice using a filtration membrane (CelluSep, 1430-45), it was concentrated with a centrifugal filter (Amicon Ultra-15, UFC905024, Merck).

Figure 3:
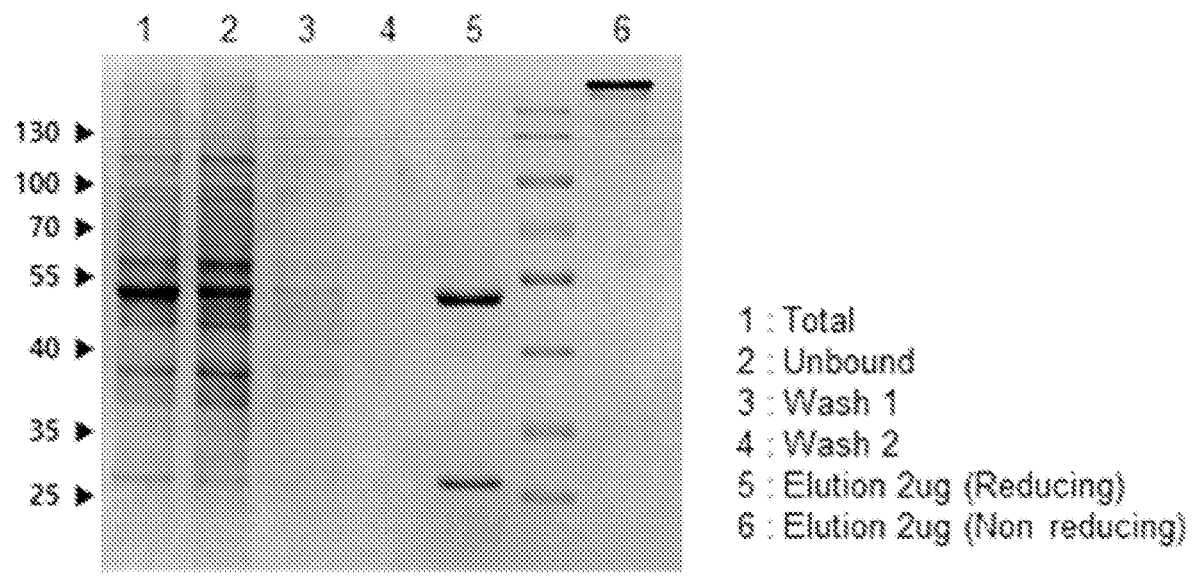
FIG. 3 confirmed that both the light chain and the heavy chain of each antibody were well expressed at the expected molecular weight as results of SDS-PAGE experiments for 4G3 IgG antibody proteins produced under reducing and non-reducing conditions, respectively.

IgG antibody proteins produced under reducing and nonreducing conditions, respectively, were confirmed by a conventional SDS-PAGE technique, and it was confirmed that the light and heavy chains of each antibody were well expressed at the expected molecular weight. FIG. 3 shows the results of SDS-PAGE confirmation for 4G3 IgG antibody.

Example 3: Evaluation of the Binding Specificity and Binding Ability of the Antibody of the Present Invention to Claudin 3

3-1. Construction of CLDN/HEK293 Cell Lines for Various Claudins

Figure 4A:
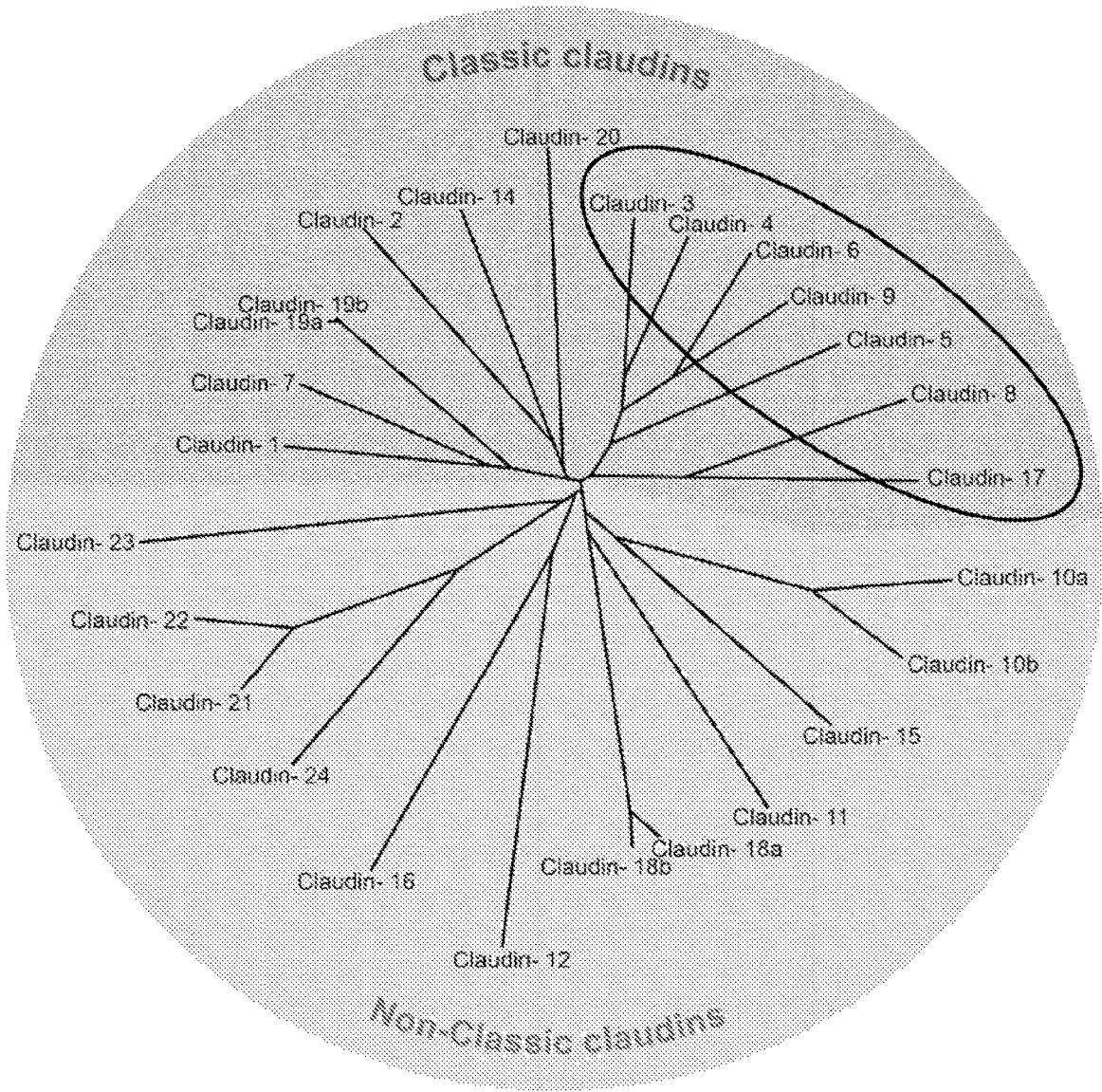
FIG. 4a shows the relationship of phylogenetic analysis within claudin families.

In order to confirm the antigen specificity of the antibody produced in Example 2-3, claudins located phylogenetic close to human CLDN3, in particular, the possibility of binding to human CLDN4 (NCBI accession number: O14493), CLDN5 (O00501), CLDN6 (P56747), CLDN8 (P56748), CLDN9 (O95484), and CLDN17 (P56750) was compared and evaluated (see FIGS. 4A and 4B). In addition, CLDN1 (O95832), a typical claudin, was used as a control group in this experiment although it is far more systematically analyzed than the above-described claudin types. In addition, it was examined whether the developed antibody also binds to mouse CLDN3 (Q9Z0G9) (see 4b). Each of the genes encoding the above-described claudins was cloned into pcDNA3.1(+) (Invitrogen). Each of the claudin expression vectors thus prepared was transduced into HEK293 (KCLB) using Fugene HD (E231A, Promega) transfection reagent, and then resistant cell lines were selected with G418.

For the cell lines (hCLDN/HEK293) that sustainably express human claudin thus prepared, whether each claudin was well expressed was confirmed using commercially available anti-CLDN1(FAB4618G, R&D systems), anti-CLDN3(FAB4620F, R&D systems), anti-CLDN4 (FAB4219F, R&D systems), anti-CLDN5(ab131259, Abcam), anti-CLDN6(ABIN1720916, Antibodies-online), anti-CLDN8(MAB5275, R&D systems), anti-CLDN9 (ab187116, Abcam), and anti-CLDN17 (MAB4619, R&D systems) antibodies.

3-2. Evaluation of Cross-Reactivity of the Antibodies of the Present Invention in CLDN/HEK293 Cell Lines In the hCLDNs/HEK293 cell lines and mCLDN3/HEK293s for various claudins prepared in Example 3-1, cross reactivity of the antibody prepared in Example 2-3 was confirmed. Original HEK293 cells were used as a negative control. First, the cells were separated into single cells using a cell dissociation buffer (Gibco, 13151-014), and then $2.5 \times 10^5$ cells were seeded, and 5 ug/ml of each antibody was added thereto and reacted on ice for 1 hour.

After the reaction, it was washed with 1% BSA/PBS, treated with a 1:100 dilution of goat anti-human IgG-FITC (109-095-098, Jackson Immunoresearch) as a secondary antibody, and reacted on ice for 1 hour. After the reaction, it was washed with 1% BSA/PBS, and analyzed using BD FACSCalibur as a flow cytometry.

Figure 5A:
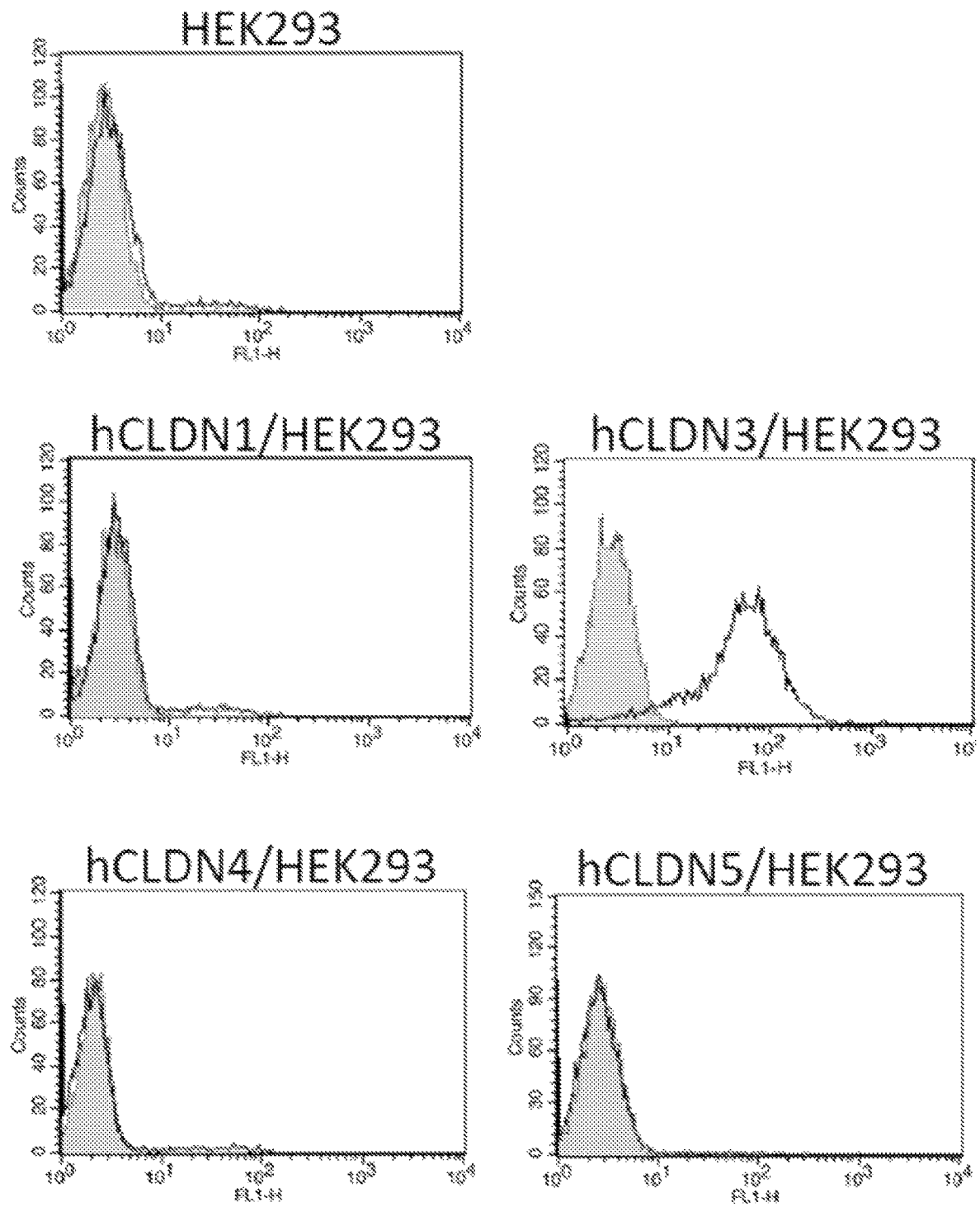
FIG. 5c shows the results of confirming the binding ability to CLDN3 expressing cells by treating the HEK293 cells transformed to express mouse CLDN3 with the 4G3 antibody of the present invention and performing flow cytometry.
Figure 5B:
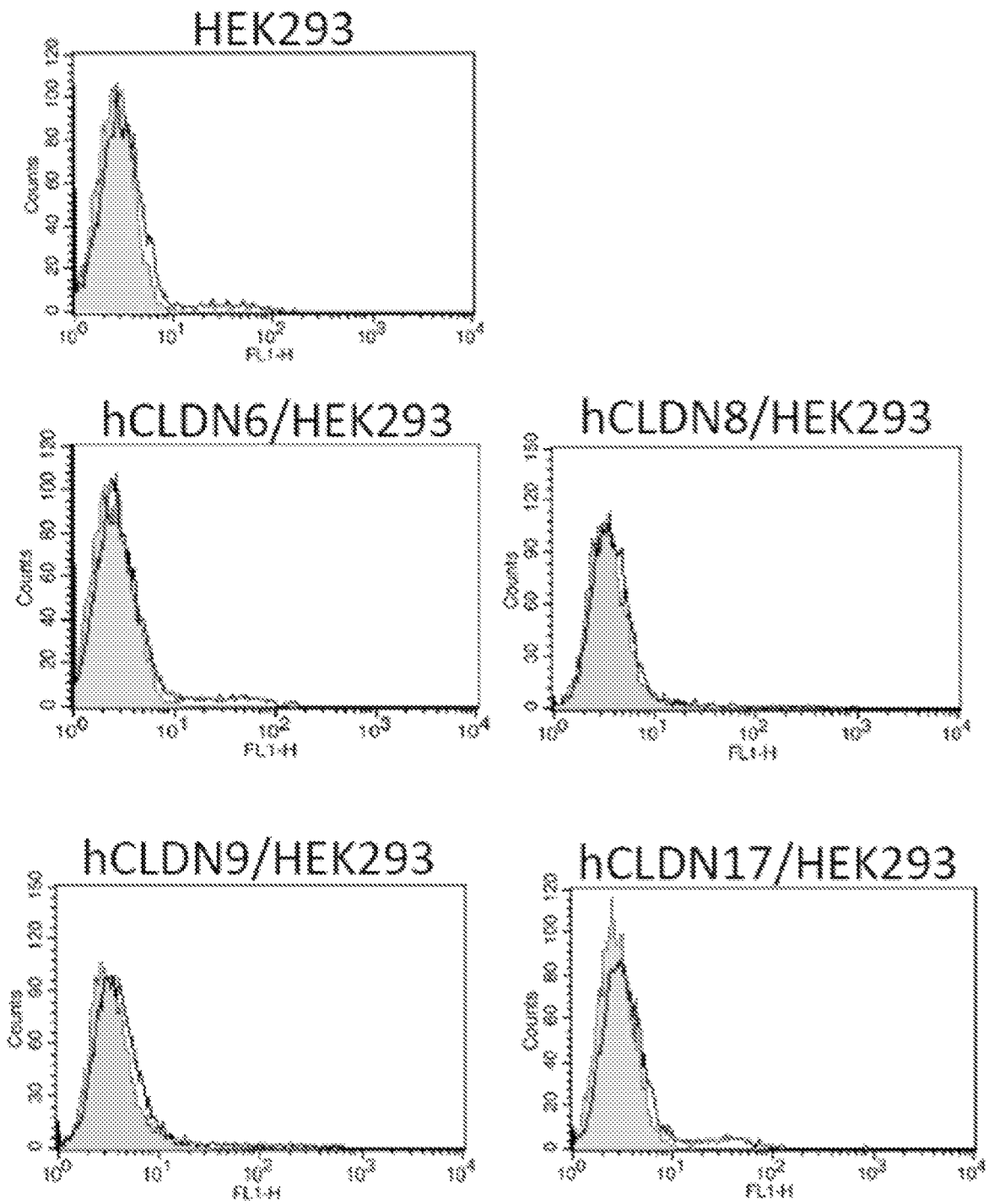
Figure 5C:
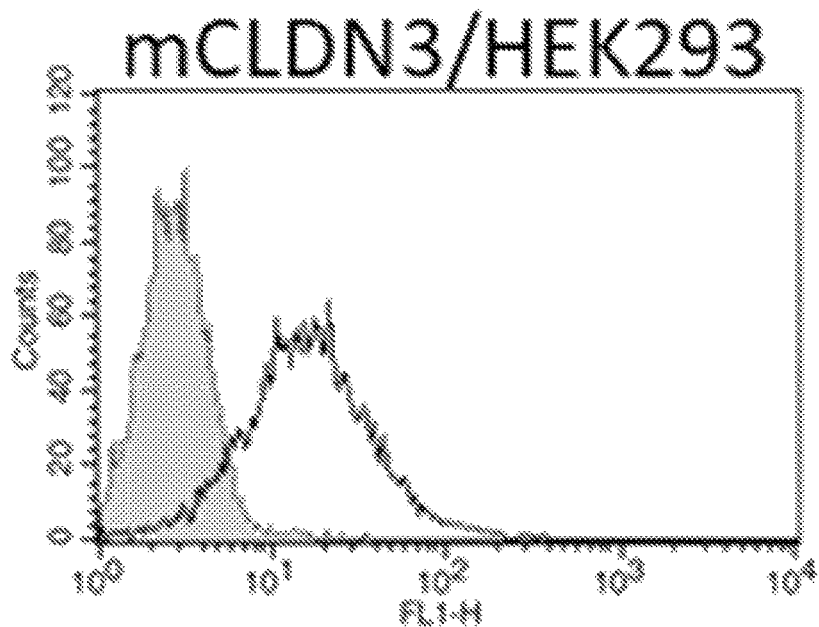

FIGS. 5a and 5b are the results of the flow cytometry, and comparatively show the binding specificity of the 4G3 antibody to claudin 3. No peak shift was observed in any experimental group using CLDN4, CLDN5, CLDN6, CLDN8, CLDN9 and CLDN17, which were phylogenetic close to CLDN3. The experimental results using mouse CLDN3 are shown in FIG. 5c, and it was confirmed that the antibody of the present invention also binds to mouse CLDN3 having high homology with human CLDN3.

Thus, it was confirmed that each antibody of the present invention did not bind to other claudin families other than human CLDN3 and mouse CLDN3. That is, each antibody of the present invention specifically binds only CLDN3 without cross-reaction with other claudin types having high homology.

3-3. Confirmation of In Vitro Cancer Cell Detection Ability_Flow Cytometry

The binding ability of the antibodies prepared in the Example 2-3 to cancer cells was confirmed. In case of ovarian cancer, OVCAR-3 (ATCC) and Caov-3 (ATCC) which are cell lines that overexpress claudin 3, TOV-112D (ATCC) which is a cell line with very low claudin 3 expression, and hCLDN3/TOV-112D cells transformed to overexpress CLDN3 were used. Preparation of hCLDN3/TOV-112D cells was performed in the same manner as described in the Example 3-1. Antibody treatment and flow cytometry for the cells were performed in the same manner as in the Example 3-2.

Figure 6:
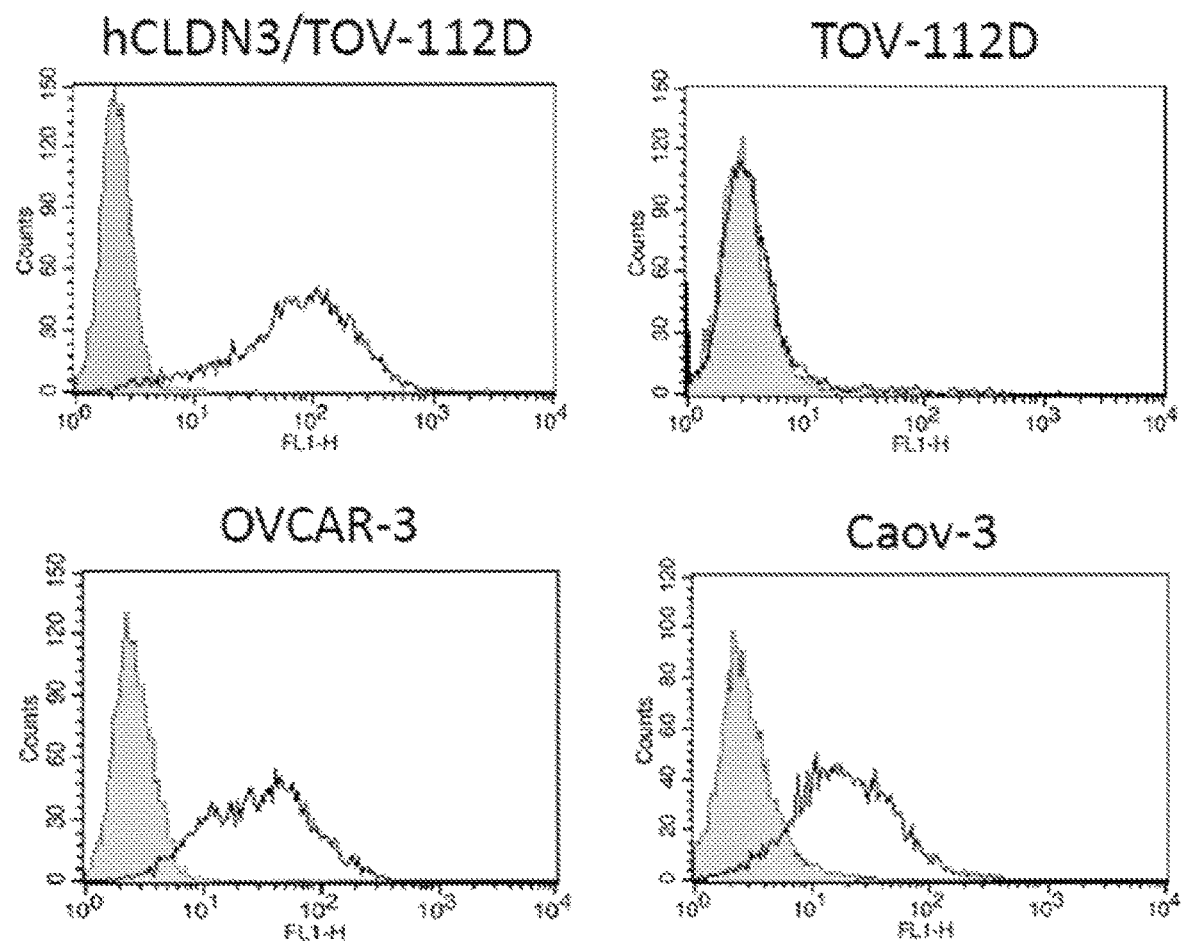
FIG. 6 show the results of comparatively confirming the binding specificity of the 4G3 antibody by treating OVCAR-3 and Caov-3 which are cell lines overexpressing claudin 3 as ovarian cancer, and TOV-112D which is a cell line having very low claudin 3 expression, and hCLDN3/TOV-112D cells transformed to overexpress CLDN3 with the 4G3 antibody of the present invention and performing flow cytometry.

As a result of the experiment, a peak shift was observed in the claudin 3-expressing cells OVCAR-3, Caov-3, and hCLDN3/TOV-112D, and no peak shift was observed in the negative cell line, TOV-112D. Representatively, FIG. 6 comparatively shows the binding specificity of 4G3 antibody to the cancer cells.

3-4. Reconfirmation of Specific Binding of Claudin 3_Immumnoprecipitation

It was reconfirmed that the antibody of the present invention binds to claudin 3 in the cancer cells through immunoprecipitation. As an antibody negative control (control IgG), a commercially available whole human antibody (009-000-003, Jackson Immunoresearch) was used.

Each cell of OVCAR-3 (ATCC), Caov-3 (ATCC), TOV-112D (ATCC), hCLDN3/TOV-112D was released with PBS added with protease inhibitor (11697498001, Roche), and then after turning on for 2 seconds and then off for 5 seconds and repeating 10 times with an ultrasonic grinder, centrifugation was performed at 15000 rpm, 4° C. for 15 minutes to obtain a supernatant. The protein concentration of each cell lysate (supernatant) was measured by the BCA quantification method, and then 1 mg of protein was taken, 1 ug of each antibody was added and reacted while rotating at 4° C. for 1 hour. Protein A bead (11719408001, Roche) was equilibrated with PBS, and the beads were blocked with 5% BSA/PBS while rotating at 4° C. for 1 hour. 50 ul of beads were added to the sample that the antibody reaction was completed, and the reaction was performed while rotating at 4° C. for 1 hour. When the reaction between the antibody and the beads was complete, after washing with PBS 3 times, 30 ul of 2×SDS loading buffer was added, boiled at 100° C. for 10 minutes, centrifuged at 12000 rpm for 3 minutes, and the supernatant was subjected to 15% SDS gel electrophoresis.

Western blotting was performed by a conventional method, and at this time, anti-CLDN3 (341700, Invitrogen) was used as the primary antibody.

Figure 7:
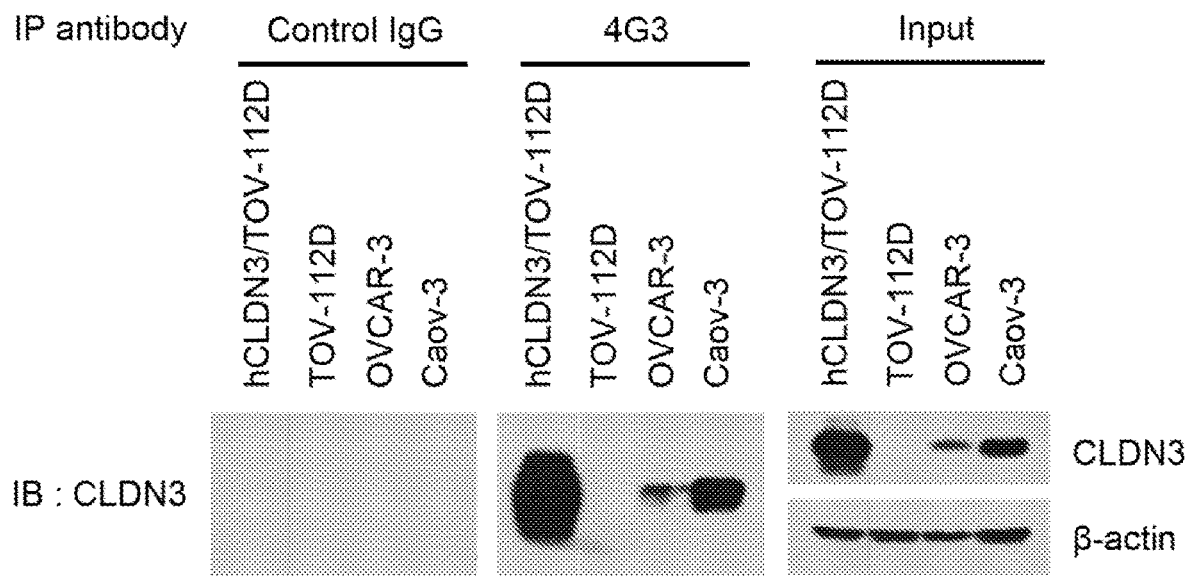
FIG. 7 shows the results of immunoprecipitation analysis for OVCAR-3, Caov-3, TOV-112D and hCLDN3/TOV-112D cells using the 4G3 antibody of the present invention (input: cells Lysate).

As a result of the analysis, a band was not observed in the control IgG-treated group, and the band was observed only in the experimental group using OVCAR-3, Caov-3, and hCLDN3/TOV-112D cells of the antibody of the present invention. FIG. 7 shows the degree of binding of the 4G3 antibody to claudin 3 expressed by the cells. This confirmed that each antibody of the present invention binds to the claudin 3 protein of cancer cells.

3-5. Reconfirmation of Specific Binding of Claudin 3_Immonofluorescence

Through immunofluorescence, it was reconfirmed that the antibody of the present invention specifically targets claudin 3 in the cancer cells. Each cell of OVCAR-3 (ATCC), Caov-3 (ATCC), TOV-112D (ATCC), and hCLDN3/TOV-112D was added to a 4 well cell culture slide by $2×10^5$ cells and cultured for 24 hours. A control antibody (ChromePure Human IgG, 009-000-003, Jackson ImmonoResearch) or the antibody of the present invention was added to the culture medium to a concentration of 5 ug/ul and reacted by stirring at 4° C. for 1 hour. After washing with PBS, 4% cells were fixed with formaldehyde for 15 minutes at room temperature. After washing with PBS, blocking was performed with 5% BSA/PBS at room temperature for 1 hour. After washing with PBS, goat anti-human IgG-FITC (109-095-098, Jackson Immunoresearch) as a secondary antibody was added to a ratio of 1:100 and reacted at room temperature for 1 hour. After washing with PBS, Hoechst 33342 (H3570, Invitrogen) was added to 1:5000 for nuclear staining and reacted at room temperature for 10 minutes, and then washed twice with PBS.

After mounting with Fluoromount™ Aqueous Mounting Medium (F4680, SIGMA), the cover slide was covered and fluorescence was observed with a confocal microscope (LSM700, Carl Zeiss, Inc.).

Figure 8A:
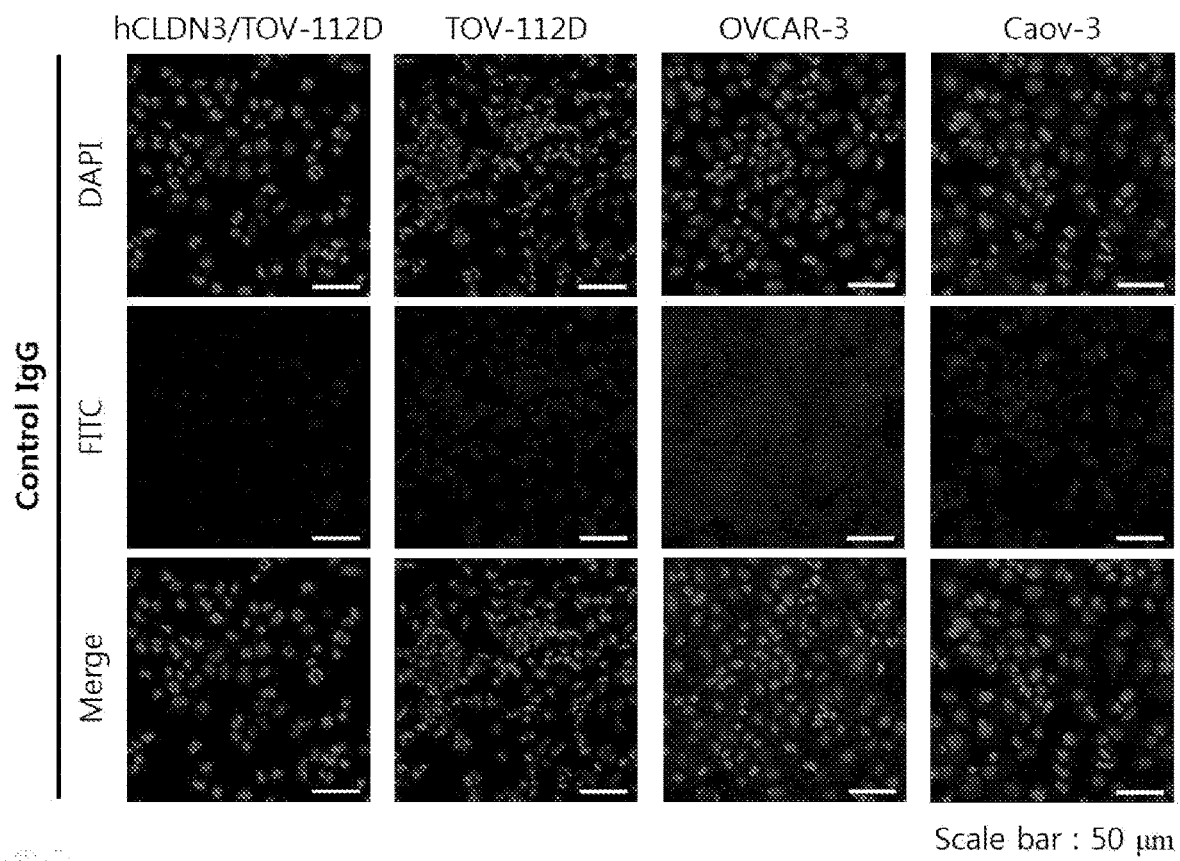
FIG. 8a shows the results of immunofluorescence staining for OVCAR-3, Caov-3, TOV-112D and hCLDN3/TOV-112D cells using a control antibody (control IgG).
Figure 8B:
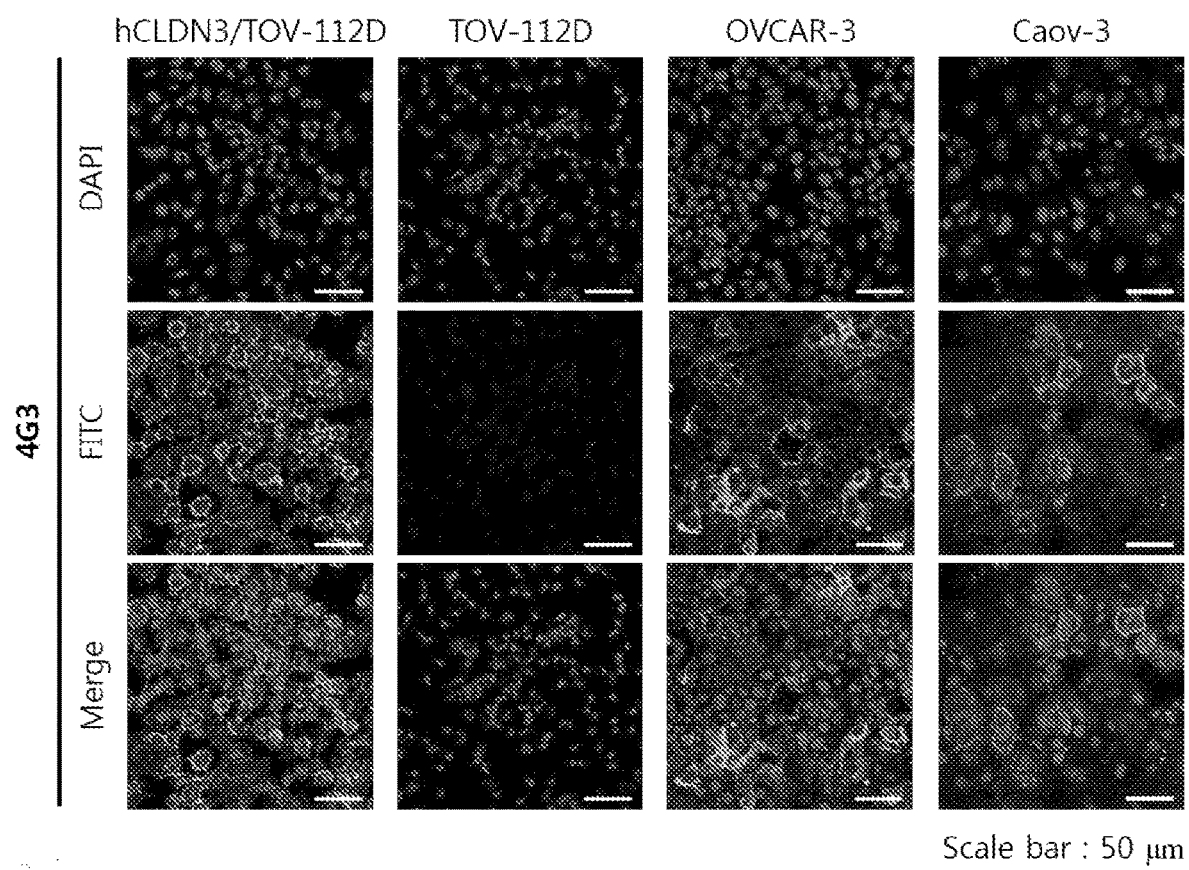
FIG. 8b shows the results of immunofluorescence staining for OVCAR-3, Caov-3, TOV-112D and hCLDN3/TOV-112D cells using 4G3 antibody.

As a result of the analysis, fluorescence was not observed in all cell lines of the control antibody (control IgG)-treated group (see FIG. 8A), whereas in the antibody-treated group of the present invention, all fluorescence was observed on the cell surfaces of cell lines hCLDN3/TOV-112D, OVCAR-3, and Caov-3 expressing the CLDN3, and no fluorescence was observed in the TOV-112D cell line not expressing CLDN3. FIG. 8b typically shows the experimental results for 4G3 antibody.

3-6. Comparison of Binding Force to Claudin 3 and Confirmation of Binding Kinetics With respect to the 4G3 IgG antibodies prepared in the Example 2-3, their binding ability to claudin 3 was confirmed. Flow cytometry was performed using CHO-CLDN3 cells, and specific experimental methods were performed in the same manner as in the Examples 1-3. Original CHO-K1 cells were used as a control, and commercially available anti-CLDN3 (FAB4620F, R&D systems) antibody was used as a control group.

In addition, the confirmation of the binding affinity of the antibody to claudin 3 was measured using LigandTracer Green (ridgeview). LignadTrcer Green (ridgeview) is a cell-based measurement device that can measure in real time whether an antibody conjugated with FITC binds to an antigen on antigen-expressing cells. FITC was conjugated to the developed antibody using the FITC Antibody Labeling Kit (53027, Pierce). As a blank one day ago, 500 ul of each 5% milk/PBS, a reference cell line with very low expression of claudin 3, and CLDN3 overexpressed cell line at a concentration of $3×10^5$ cells/ml were added in a coin size to a quadrant of a 100 mm culture dish. After incubation for 6 hours at 37° C. at 5% $CO_2$, the medium was removed, washed with PBS, and then 10 ml of the medium was added and cultured overnight. HEK293 (KCLB) and TOV-112D (ATCC) were used as reference cell lines, and hCLDN3/HEK293 and hCLDN3/TOV-112D were used as CLDN3 overexpressing cell lines. On the day of the experiment, after removing the entire medium and replacing it with 3 ml medium, the culture dish was mounted on the equipment, and after stabilization, the FITC-conjugated antibody was sequentially added to the final concentration of 3 nM and 9 nM. Each of them reacted until the fluorescence value reached equilibrium, and finally, the degree of dissociation was confirmed after replacing with 3 ml new medium. The fluorescence measurement time was 15 seconds, the measurement delay time was 4 seconds, and the measurement interval was 72 seconds. By repeating the experiment three times, the fluorescence values in hCLDN3/HEK293 cells compared to HEK293 cells and the fluorescence values in hCLDN3/TOV-112D cells compared to TOV-112D cells were analyzed with a one to one two state fitting model model. The resulting values are shown in FIG. 9C and Table 3.

TABLE 3

| CLDN3 cell lines | Fitting model | $k_a1$ ($M^{-1}s^{-1}$) | $k_d1$ ($s^{-1}$) | $k_a2$ ($s^{-1}$) | $k_d2$ ($s^{-1}$) | $K_D$ (nM) | Chi2 (%) |
|---|---|---|---|---|---|---|---|
| hCLDN3/HEK293 | 1:1, 2 state | $4.66 × 10^4$ | $6.71 × 10^{-4}$ | $1.56 × 10^{-4}$ | $4.35 × 10^{-5}$ | 4.03 | 34.27 |
| hCLDN3/TOV-112D | 1:1, 2 state | $4.74 × 10^4$ | $3.37 × 10^{-4}$ | $7.77 × 10^{-4}$ | $2.57 × 10^{-5}$ | 2.35 | 10.15 |

Figure 9A:
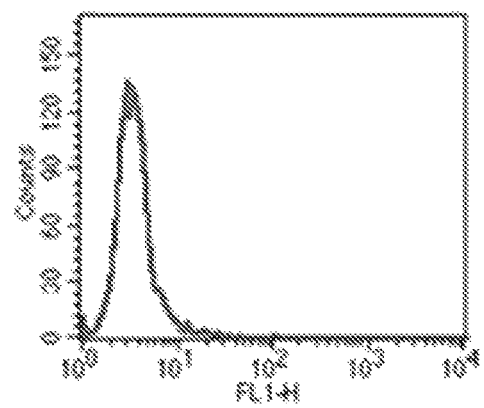
FIG. 9a is a result of flow cytometry for binding of the antibody of the present invention (4G3 IgG) to CHO-K1 cells (negative cell line, control).
Figure 9A:
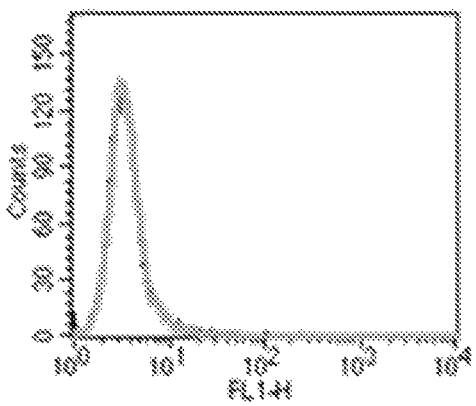
Figure 9A:
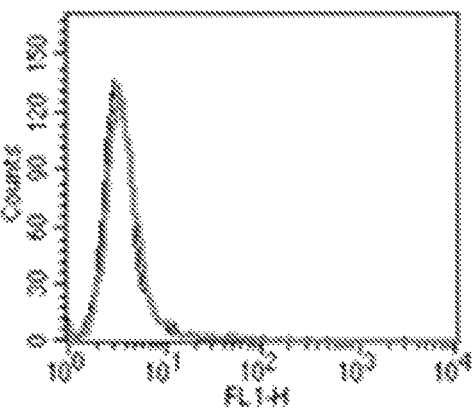
Figure 9C:
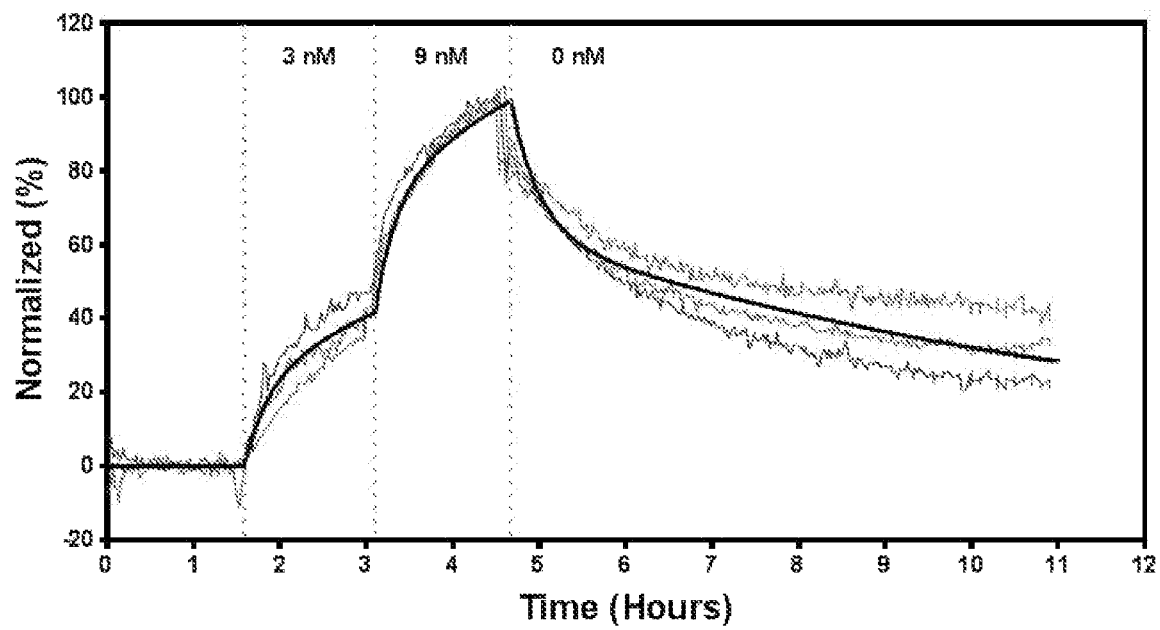
FIG. 9c is a result of measuring the binding affinity (dissociation constant ($K_D$)) of the antibody of the present invention (4G3 IgG) in CLDN3 expressing cells (hCLDN3/HEK293 and hCLDN3/TOV-112D) by LigandTracer Green (ridgeview).
Figure 9C:
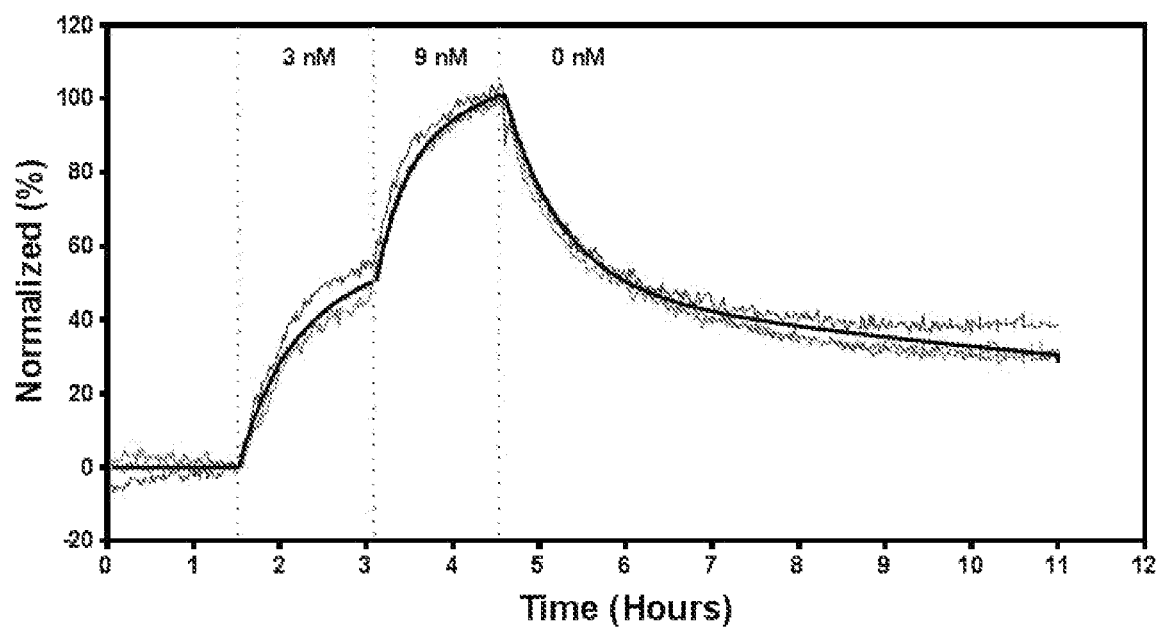

As shown in FIGS. 9a and 9b, it was confirmed that all of the 4G3 IgG antibodies showed peak shifts and bound to claudin 3. At this time, the difference in peak shift was larger in the 4G3 IgG antibody-treated group, and as a result, it was confirmed that the 4G3 IgG antibody has better specific binding ability to claudin 3 than the conventional commercially available antibody.

In addition, as a result of binding affinity analysis, as shown in FIG. 9c and Table 3, the kinetic value (KD) of 4G3 for claudin 3 expressing cells was 4.03 nM (hCLDN3/HEK293) and 2.35 nM (hCLDN3/TOV-112D) in two cell lines, respectively and confirmed the high affinity of 4G3 for claudin 3. These results show that the 4G3 IgG antibody of the present invention has significantly better affinity than the existing anti-claudin3 antibodies. For example, the affinity is more than 5 times better than the existing IgGH6 antibody of 'Chiara Romani etl al. Oncotarget. 2015'.

Example 4: Identification of Antigen Binding Site

Figure 10A:
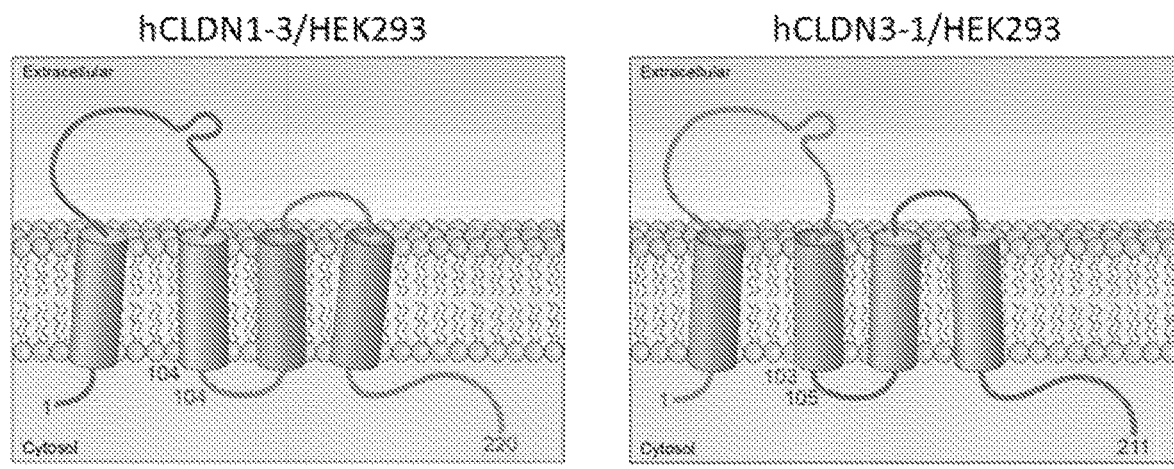
FIG. 10a is a schematic diagram of the expression (structure) pattern of each fusion protein in cells expressing a fusion protein comprising a region of amino acids 1 to 104 of CLDN1 as an extracellular first loop and a region of amino acids 104 to 220 of CLDN3 as an extracellular second loop (hCLDN1-3/HEK293), and in cells (hCLDN3-1/HEK293) expressing a fusion protein containing a region of amino acids 1 to 103 of CLDN3 as EL1 and a region of amino acids 105 to 211 of CLDN1 as EL2.

Within the regions in which CLDN3 naturally expressed in cells is exposed to the outside of the cell, specifically, it was attempted to confirm where the antigen-binding site to which the antibody of the present invention binds. Accordingly, to confirm it, a fusion protein was made in which regions corresponding to the extracellular 1st loop and the extracellula 2nd loop of CLDN3 were replaced with the corresponding regions in CLDN1. A gene expressing amino acids 1 to 104 of CLDN1 and 104 to 220 of CLDN3 amino acids (hCLDN1-3) or a gene expressing CLDN1 amino acids 105 to 211 and CLDN3 amino acids 1 to 103 (hCLDN3-1) were respectively cloned into pcDNA 3.1(+) (Invitrogen). After each gene was transduced into HEK293 (KCLB), a resistant cell line was selected with G418 to prepare a cell line continuously expressing the fusion protein of hCLDN1-3 or hCLDN3-1. These were designated as hCLDN1-3/HEK293 and hCLDN3-1/HEK293, respectively (see FIG. 10a). Whether the desired fusion protein was expressed in each cell line was confirmed by a conventional Western blotting method using anti-CLDN3 (341700, Invitrogen), anti-CLDN1 (sc-137121, Santa Cruz Biotechnology, Inc.) (See the bottom of FIG. 10b). Treatment of the 4G3 antibody and flow cytometry for hCLDN1-3/HEK293 or hCLDN3-1/HEK293 cells were performed in the same manner as in Example 3-2.

Figure 10B:
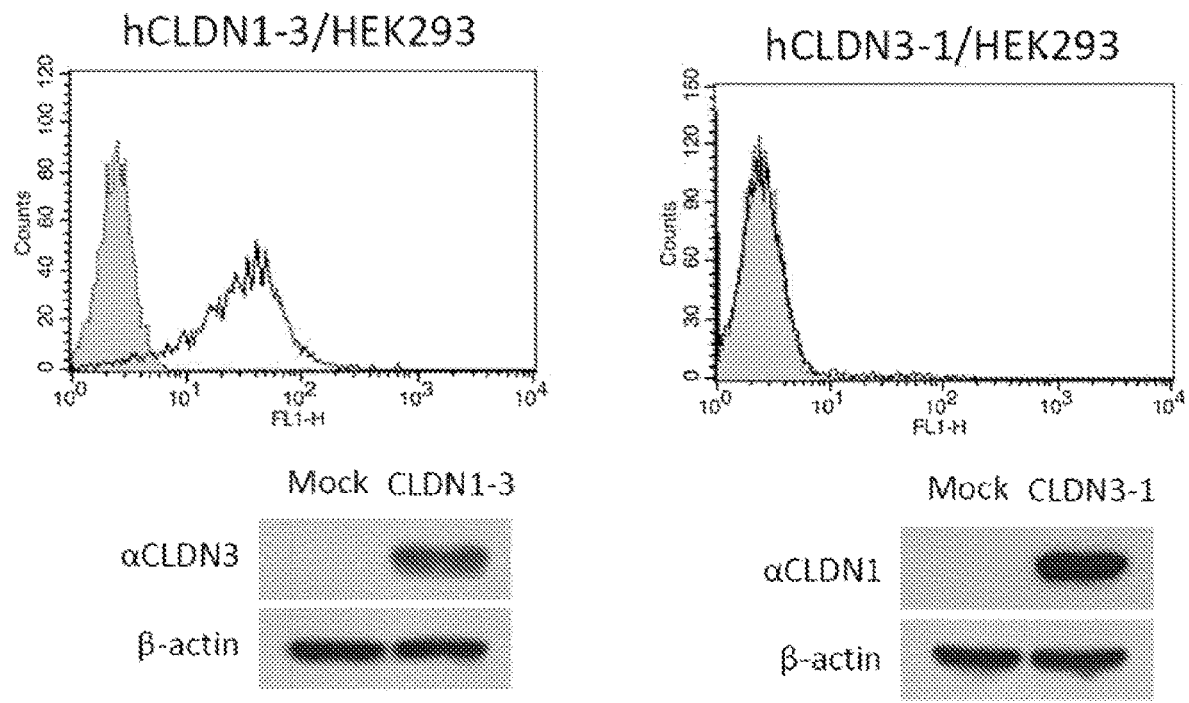
FIG. 10b shows a result of flow cytometric after processing the 4G3 antibody against hCLDN1-3/HEK293 or hCLDN3-1/HEK293 cells (top), and a result of western blow confirming whether the desired fusion protein was properly expressed in the cells (bottom).

As a result of the analysis, as shown in FIG. 10b, a peak shift was observed in the experiment for hCLDN1-3/HEK293, and no peak shift was observed in the experiment for hCLDN3-1/HEK293.

As a result, it was confirmed that the 4G3 antibody binds to the extracellula $2^{nd}$ loop region of hCLDN3.

Example 5: Confirmation of Endocytosis of IgG 4G3 Antibody

In order to confirm the internalization ability of the antibody of the present invention into the cells, OVCAR-3 (ATCC) and Caov-3 (ATCC), which are ovarian cancer cell lines overexpressing claudin 3, were added to 4 well cell culture slides by 2×105 pieces and incubated for 24 hours. 1 mM of LysoTracker Red DND-99 (L7528, Life Technologies Inc.) staining lysosomes on cells after culture, control IgG (ChromePure Human IgG, 009-000-003, Jackson ImmonoResearch) or KM3907 (An antibody having the VH of SEQ ID NO: 13 and the VL of SEQ ID NO: 14, prepared in the same manner as in Example 2-1 (see SEQ ID NOs: 15 and 16 for the full length of KM3907 antibody)/CLDN3&CLDN4 target, ECL-1 binding) as a control antibody, and 4G3 antibody of the present invention were treated to become 10 ug/ml, and incubated for 1 hour, 2 hours, 4 hours, and 6 hours at 37° C. After the cultivation was completed for each time, it was washed with PBS and fixed for 15 minutes at room temperature with 4% formaldehyde. After washing with PBS, 0.1% Triton-X100/PBS was treated three times for 5 minutes. After washing with PBS, blocking was performed for 1 hour at room temperature with 5% BSA/PBS. After washing with PBS, goat anti-human IgG-FITC (109-095-098, Jackson Immunoresearch) was added to 1:100 as a secondary antibody and reacted at room temperature for 1 hour. For nuclear staining after washing with PBS, Hoechst 33342 (H3570, Invitrogen) was added to a ratio of 1:5000 and reacted at room temperature for 10 minutes, and then washed twice with PBS. After mounting with Fluoromount™ Aqueous Mounting Medium (F4680, SIGMA), the cover slide was covered and fluorescence was observed with a confocal microscope (LSM700, Carl Zeiss, Inc.).

Figure 11A:
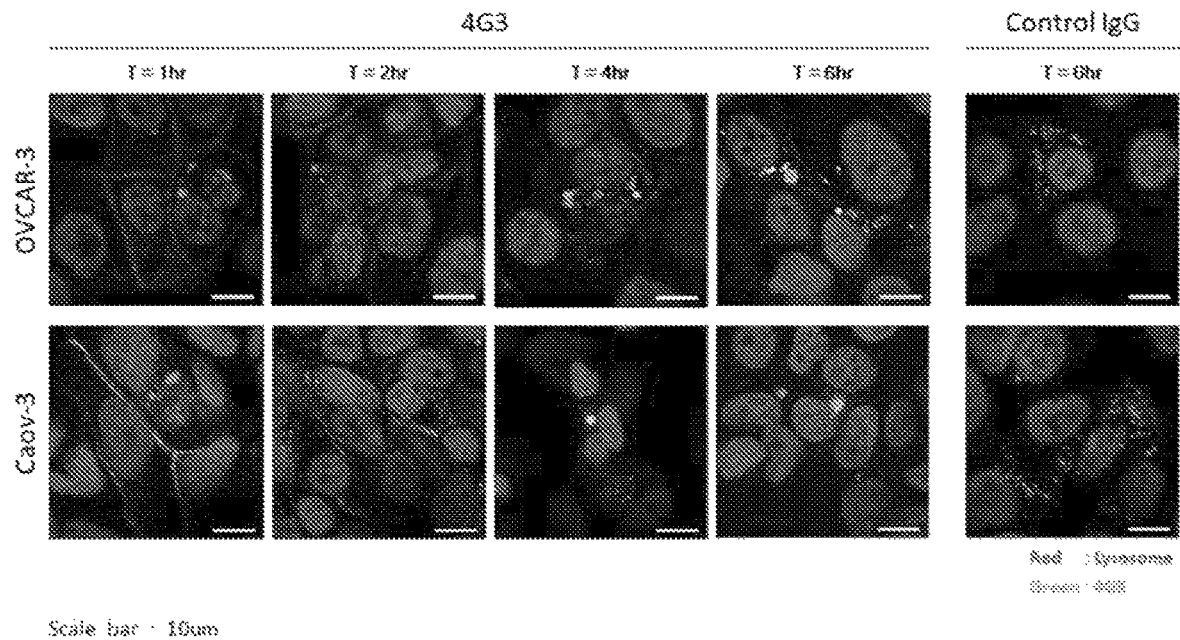
FIG. 11a shows the results of observing as time passes that the antibody of the present invention binds to claudin 3, and then enters into the ovarian cancer cell lines OVCAR-3 and Caov-3 cells by endocytosis using immunofluorescence staining.
Figure 11B:
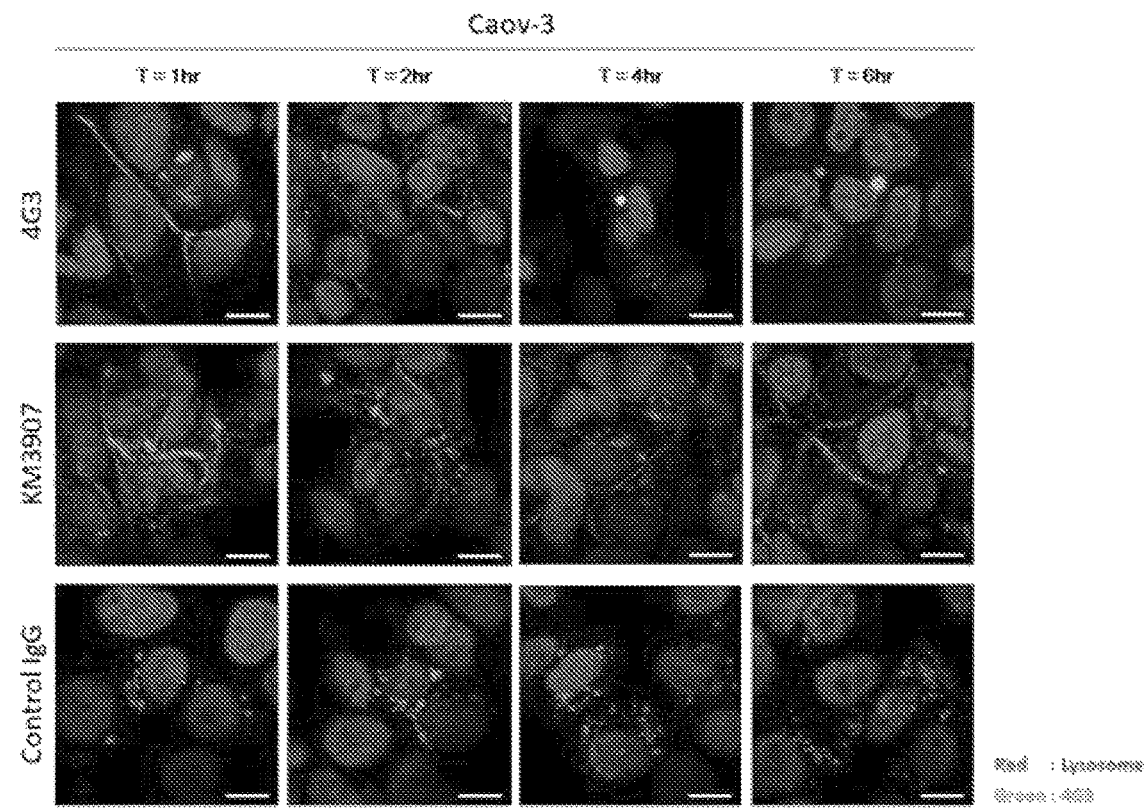
FIG. 11b shows the internalization effect of the antibody of the present invention, in contrast with other antibodies known to attach to claudin 3 (KM3907).
Figure 12A:
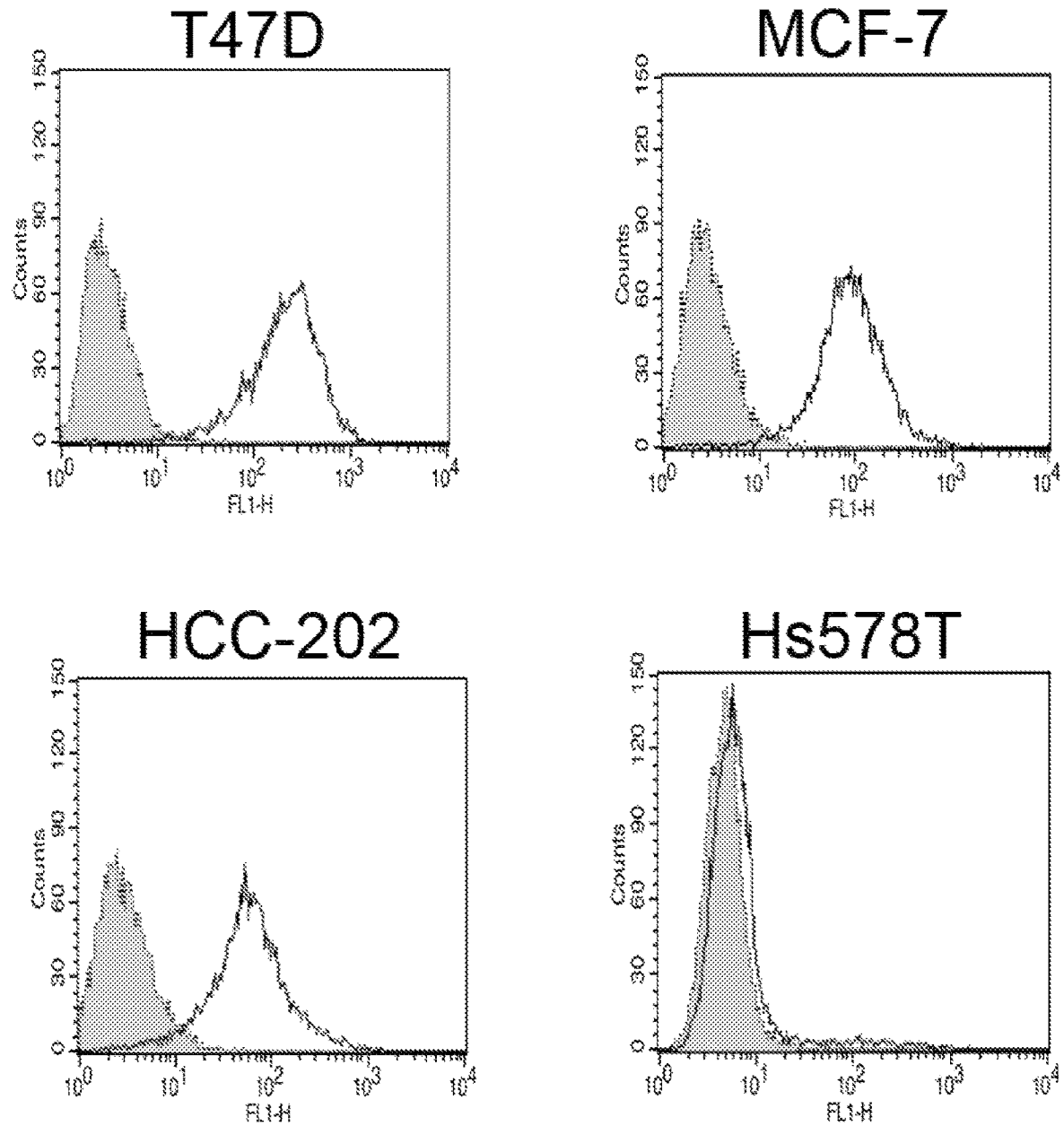
Figure 12B:
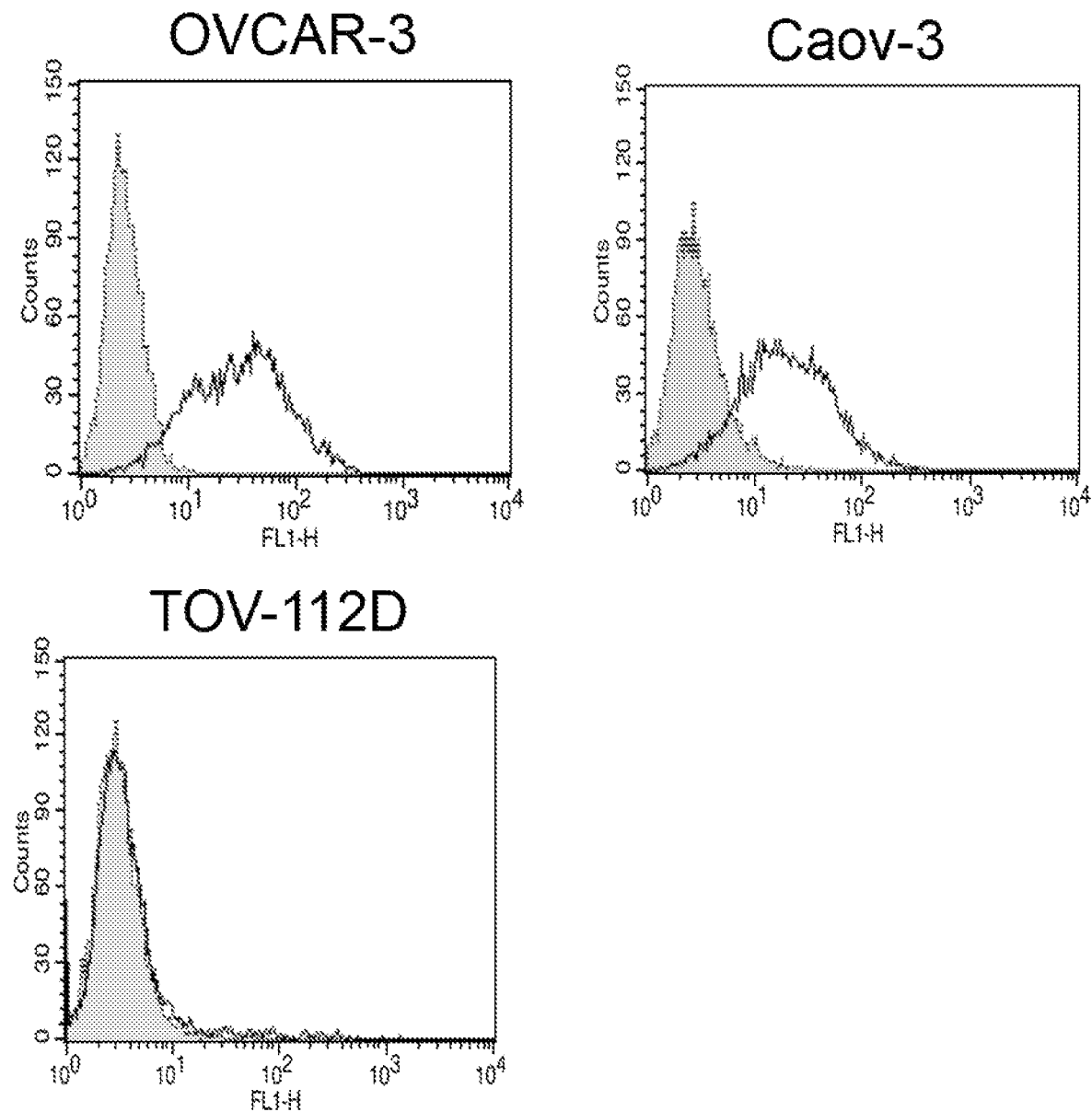
Figure 12D:
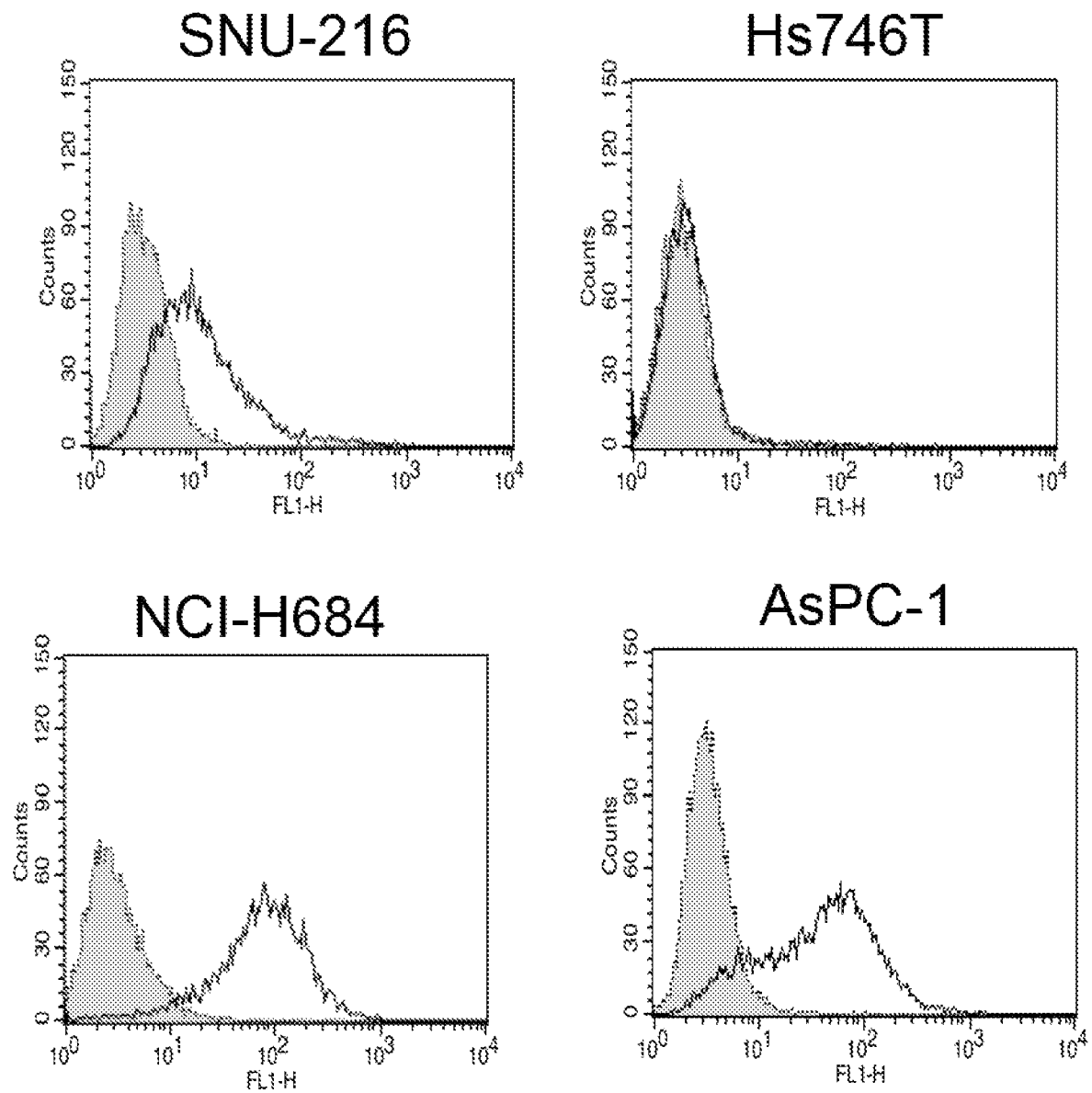
Figure 12E:
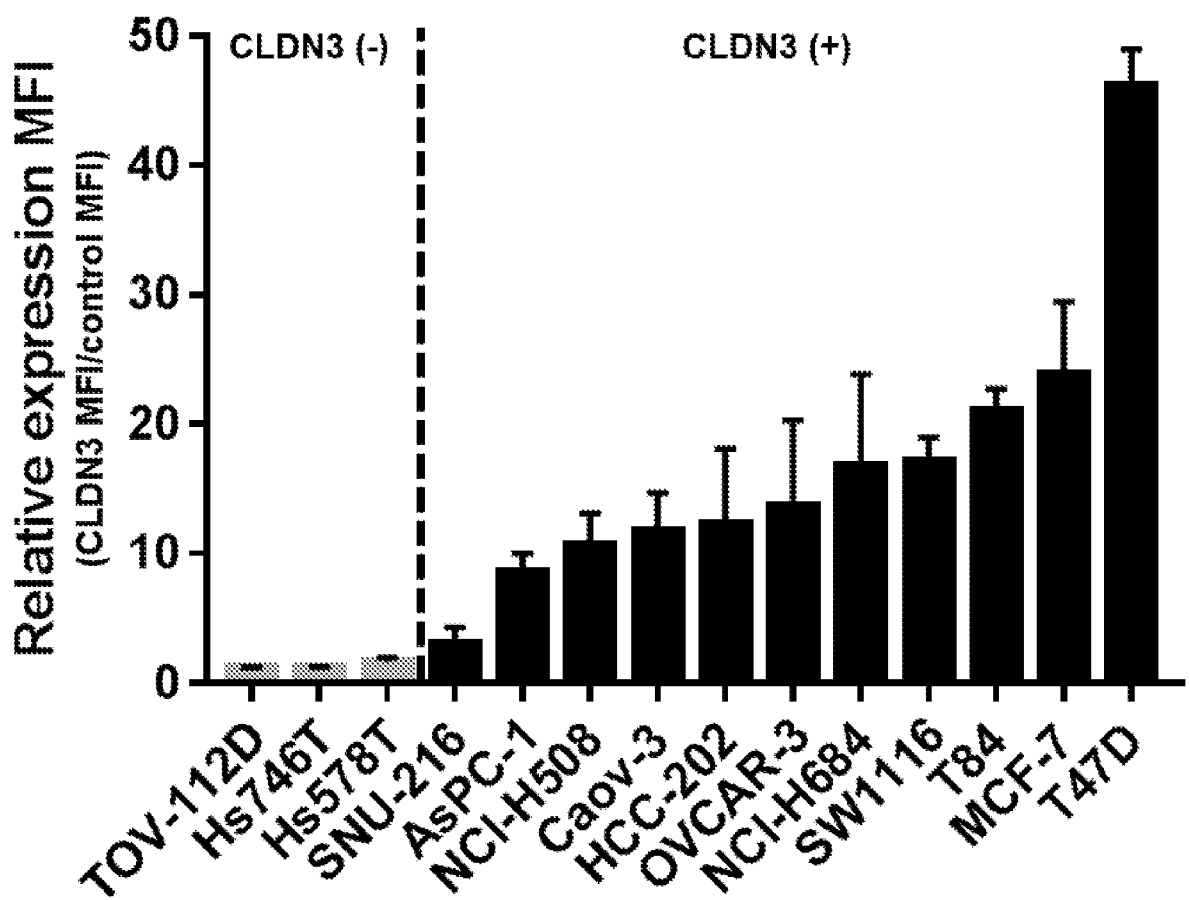
Figure 13A:
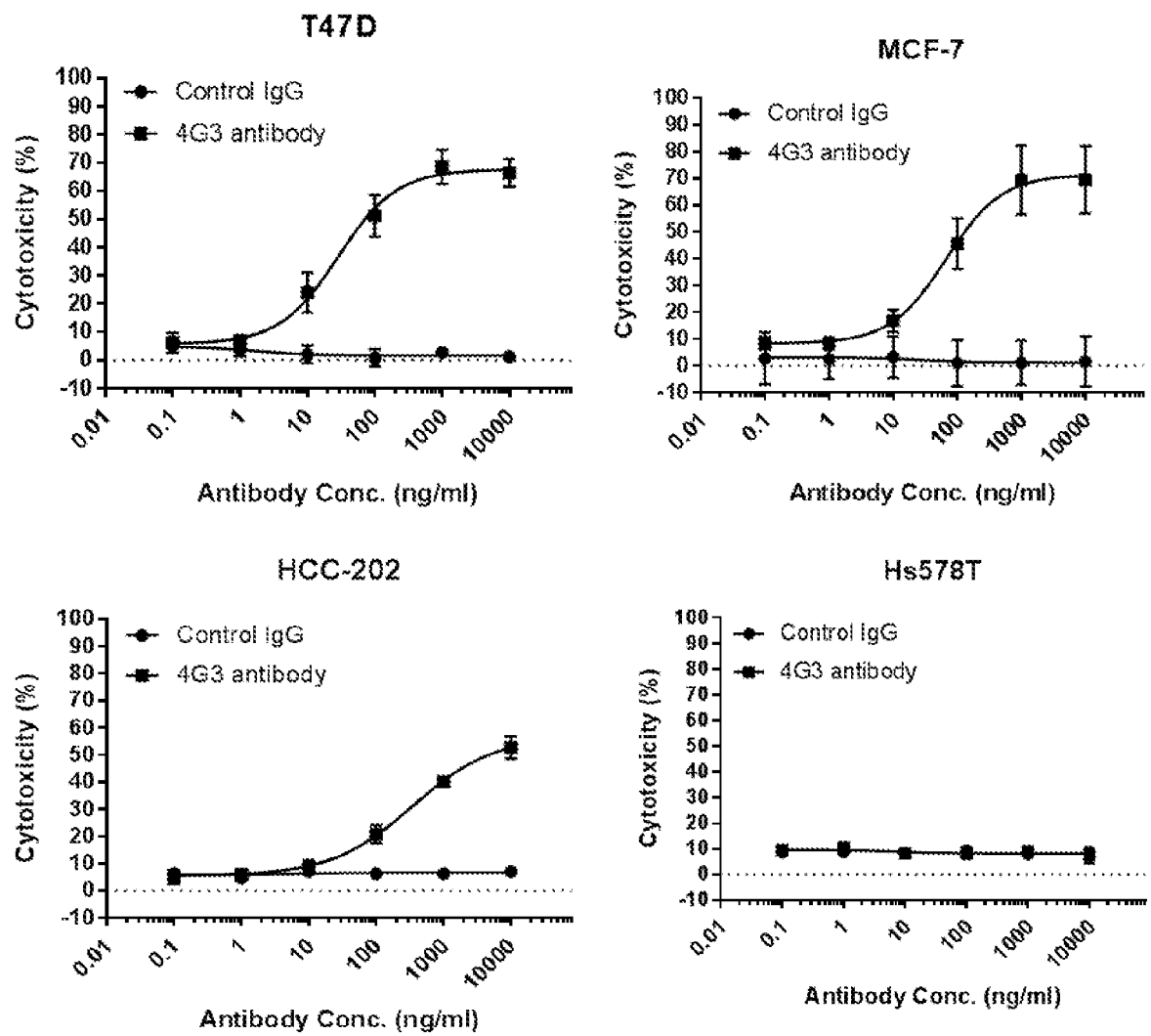
FIGS. 13a to 13e show the results of concentration-dependently confirming the antibody-dependent cell-mediated cytotoxicity (ADCC) effect by treating the 4G3 antibody in the cells.
Figure 13B:
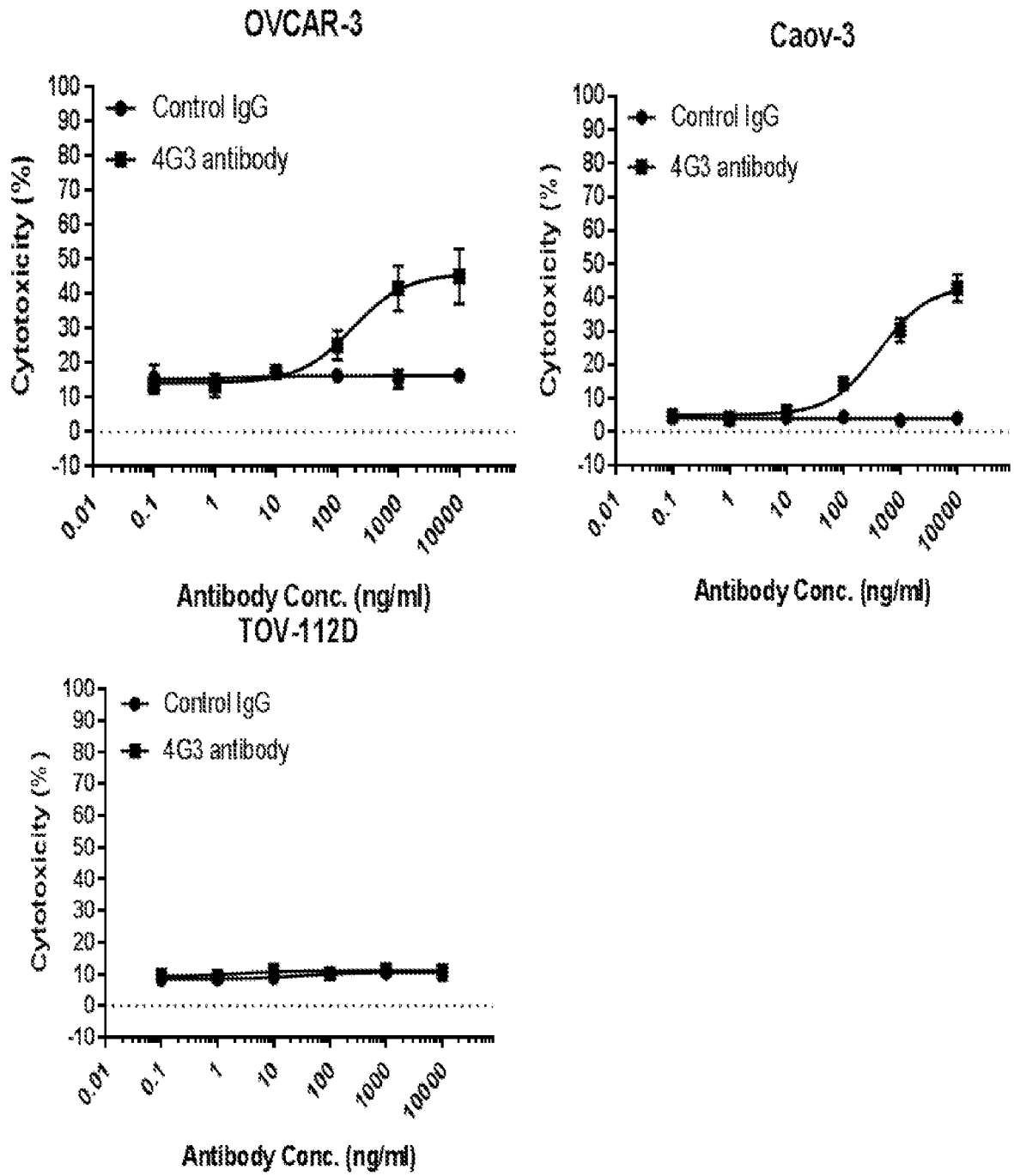
Figure 13C:
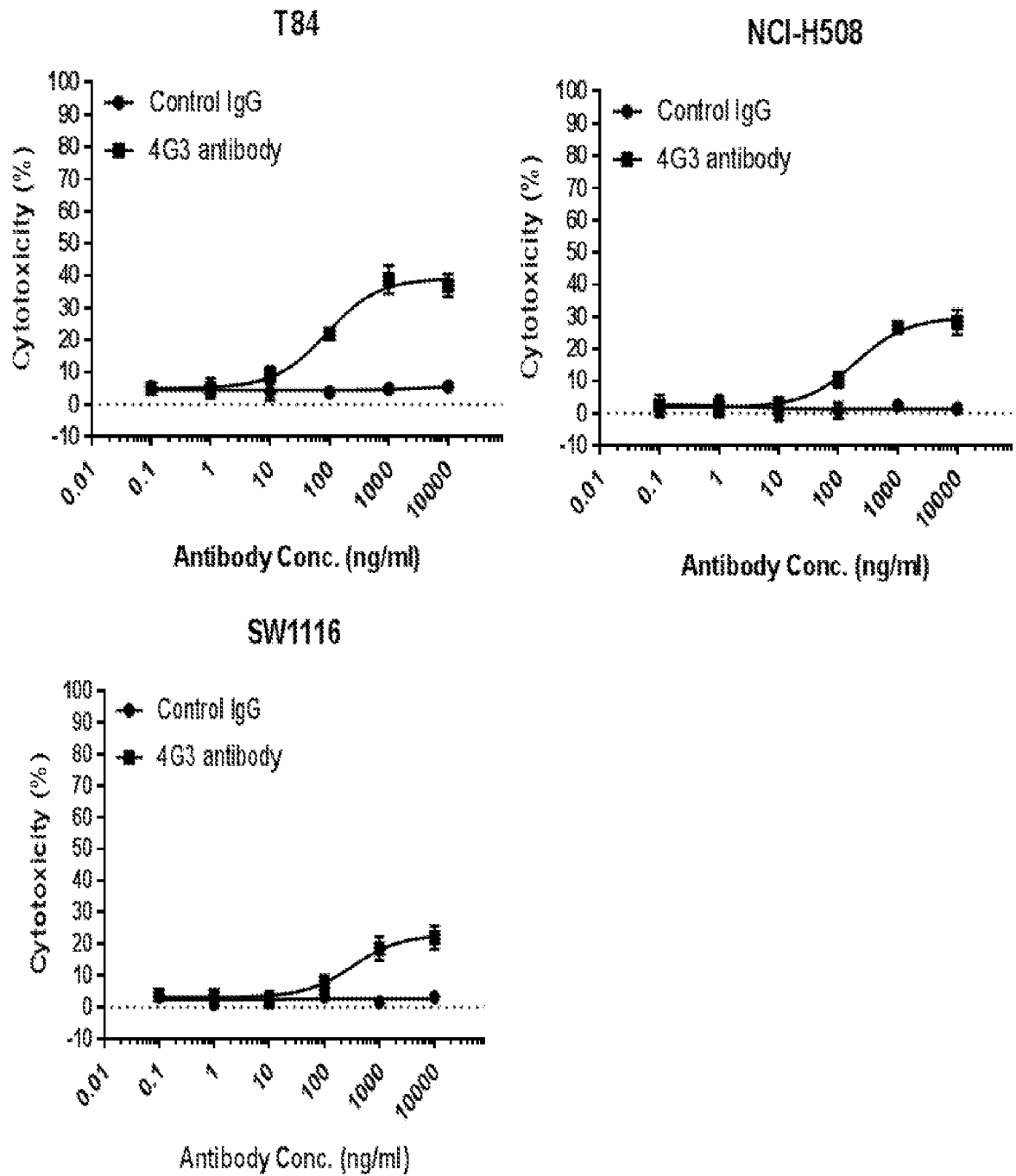
Figure 13D:
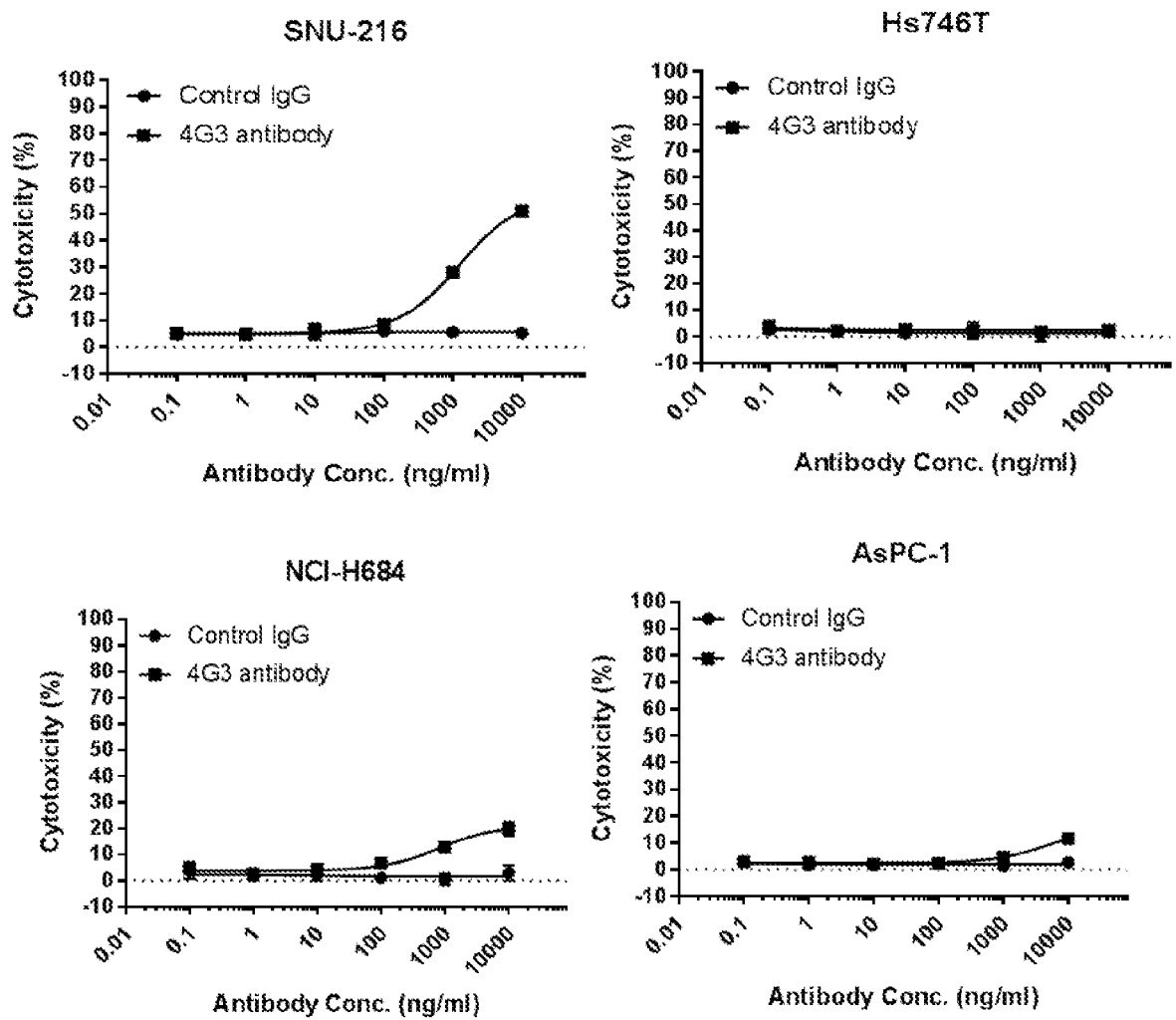
Figure 13E:
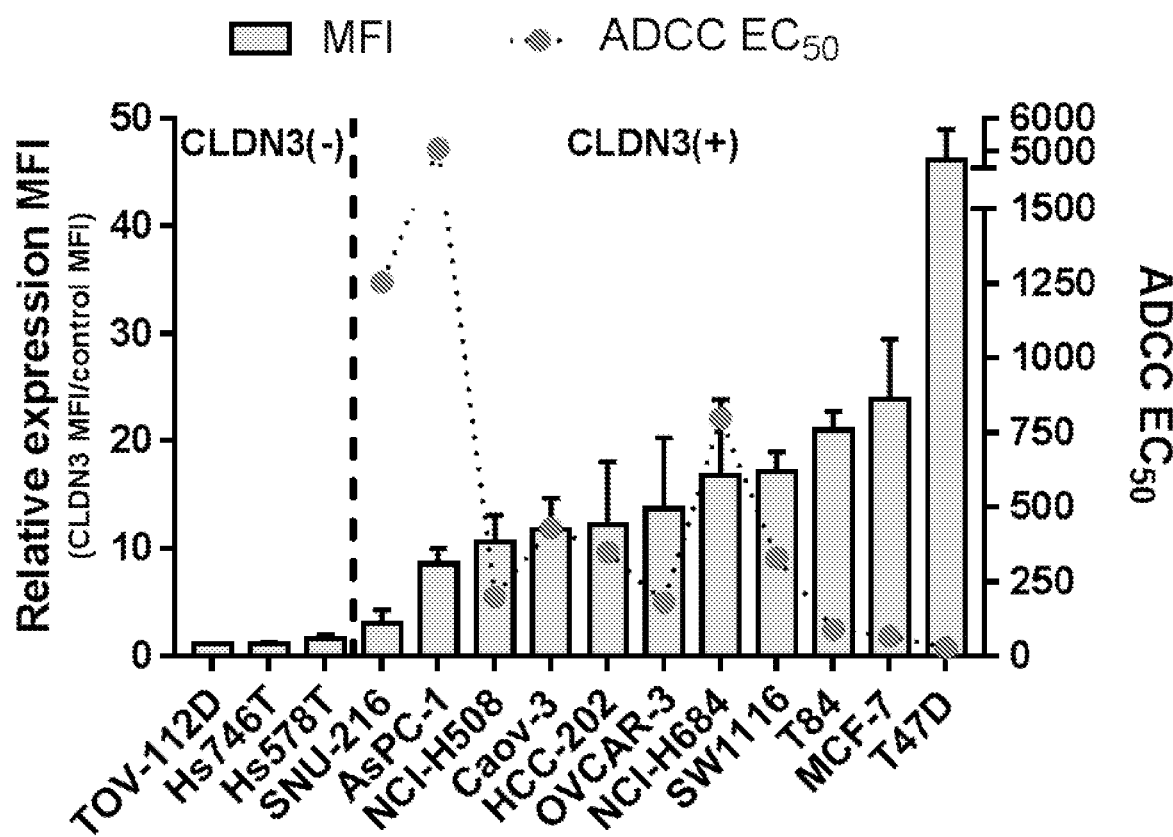

As a result of observation in FIG. 11a, it was confirmed that the 4G3 antibody entered the cell and was located on the lysosome. In addition, as shown in FIG. 11b, in the case of KM3907 which is a known anti-claudin 3 antibody, internalization into cells was not observed.

Example 6: Confirmation of Antibody-Dependent Cytotoxicity Against Cancer Cells

In order to confirm the antibody-dependent cell-mediated cytotoxicity (ADCC) of the antibody of the present invention, a cell line (hereinafter referred to as NK-92M1-CD16) that continuously expresses the Fc receptor CD16 gene in NK-92MI was used. In order to prepare the NK-92MI-CD16 cell line, the CD16 gene was inserted into pcDNA3.1(+) (Invitrogen) using Nhe1 and EcoR1 restriction enzymes, and the CD16 expression vector was transfected into NK-92MI cells by electroporation.

After selecting the resistant cell line with the G418 compound, the overexpressing cell line was isolated with the FACS Aria equipment. In order to confirm the effect of expression of claudin 3 in various cancer cells, the level of claudin 3 expression of each cell was first confirmed by flow cytometry with this antibody, and then MFI was compared (see FIGS. 12a to 12e). Antibody treatment and flow cytometry for the cells were performed in the same manner as in Example 3-2. In order to observe antibody-dependent cytotoxicity, each cell was added to a 96 well plate by 2×10⁴ cells and cultured for 24 hours. After treating a control antibody (ChromePure Human IgG, 009-000-003, Jackson ImmonoResearch) or 4G3 antibody with 0ng/ml, 0.1 ng/ml, 1 ng/ml, 10 ng/ml, 100 ng/ml, 1000 ng/ml and 10000 ng/ml, and NK-92M1-CD16 cells were added to each of 8×10⁴ cells and cultured at 37° C. for 4 hours. In order to measure LDH (Lactate dehydrogenase) from which the cells are dissolved, the supernatant was taken after centrifugation, and the absorbance was measured at 490 nm using CytoTox 96© Non-Radioactive Cytotoxicity Assay (G1780, Promega). The calculation formula for measuring antibody-dependent cytotoxicity is as follows.

$$\% \text{ cytotoxicity} = \frac{\text{Experimental} - \text{Effector Spontaneous} - \text{Target Spontaneous}}{\text{Target Maximum} - \text{Target Spontaneous}} \times 100$$

As a result of the analysis in FIGS. 13a to 13e, cytotoxicity was not observed in the control antibody (control IgG)-treated group, and in the 4G3 antibody-treated group, cytotoxicity was observed in cells expressing claudin 3. When comparing the ADCC effect according to the amount of claudin 3 expression, as the MFI value of claudin 3 expression increased, the cytotoxic EC50 tended to decrease.

In the above experiment, NK-92MI-CD16 cells continuously expressing CD16 (FcγRIIIa) exhibit a cytotoxic effect on claudin 3 antigen, suggesting that cancer cells can be killed by a mechanism similar to the principle of CAR-NK technology. In fact, the ADCC efficacy evaluation showed that the tendency of efficacy was consistent according to the expression of claudin 3, indicating that the developed antibody can be applied to the preparation of CAR-NK cells.

Example 7: Confirmation of In Vivo Tumor Targeting Ability

The tumor xenograft animal model was prepared by suspending 5×10⁶ human ovarian cancer cells OVCAR-3 (ATCC) and human breast cancer cells T47D (ATCC) in 100 ul PBS, and injecting them subcutaneously into the lower flank of a 6-week-old Athymic nude female mouse. In the case of T47D, 17β-estradiol pellet (SE-121, Innovative Research of America) was injected subcutaneously with them.

In order to confirm the in vivo tumor targeting ability of the antibody of the present invention, a control antibody (ChromePure Human IgG, 009-000-003, Jackson ImmonoResearch) and 4G3 antibody were conjugated with a CF750 fluorophore using VivoBrite™ Rapid Antibody Labeling Kit (92161, Biotium). The fluorescence/antibody molar ratio (degree of labeling, DOL) was measured to be 2.29 and 2.82, respectively, according to the recommended expected ratio according to the formula provided in the kit.

On the 60th day after tumor implantation in the animal model, a control antibody or 4G3 antibody labeled with CF750 fluorescence was intravenously injected at a dose of 100 ug/100 ul. A fluorescence signal emitted from the mouse was detected using a small animal biometric imaging system at 6 hours, 24 hours, 48 hours, 72 hours, and 96 hours and liver, kidney, lung, spleen, small intestine, and tumor were excised to confirm the fluorescence signal of antibody distribution by tissue at the last time point. Fluorescence signals were analyzed using Living Imaging Software supplied by the manufacturer.

Figure 14A:
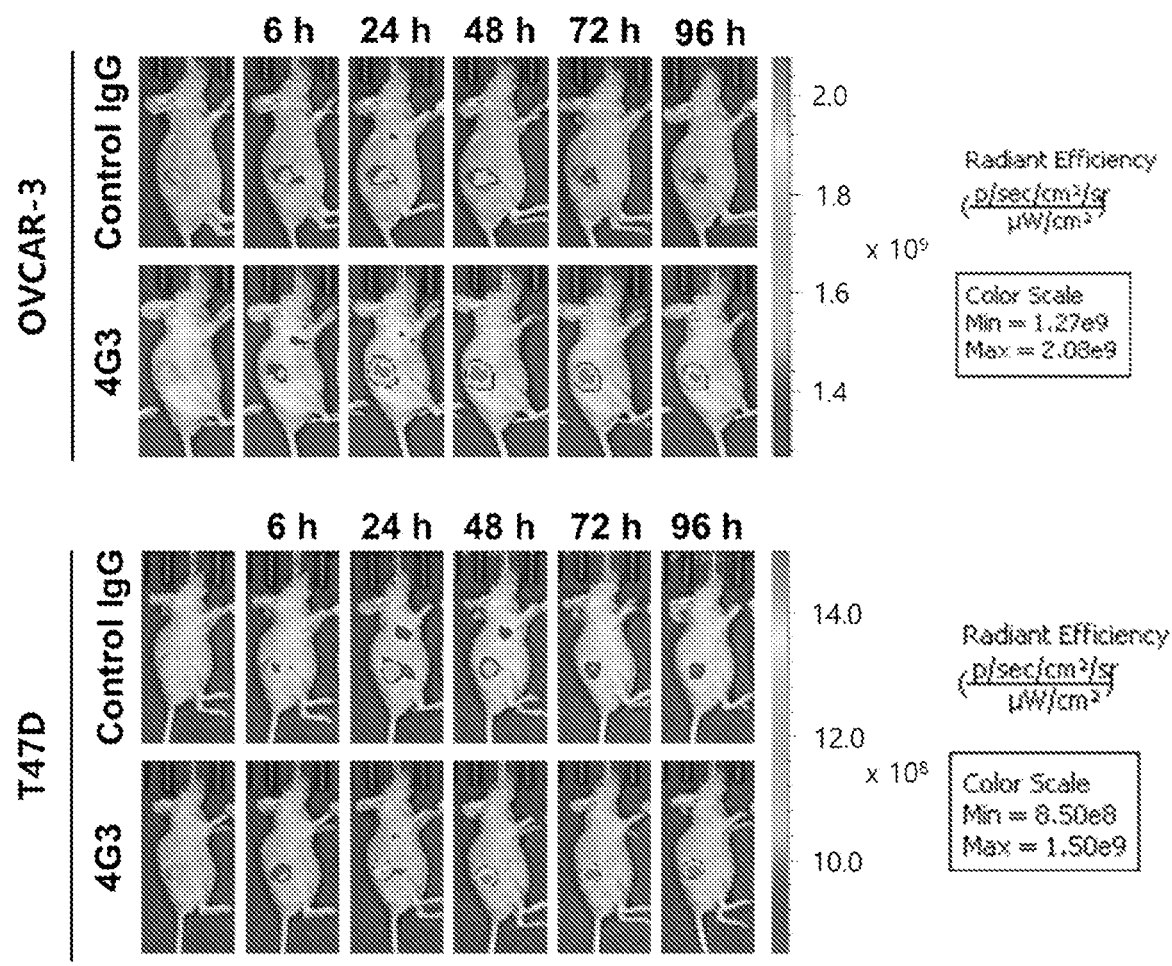
FIG. 14a shows the results of confirming the in vivo tumor targeting ability of the 4G3 antibody of the present invention in an animal model of tumor xenograft.
Figure 14B:
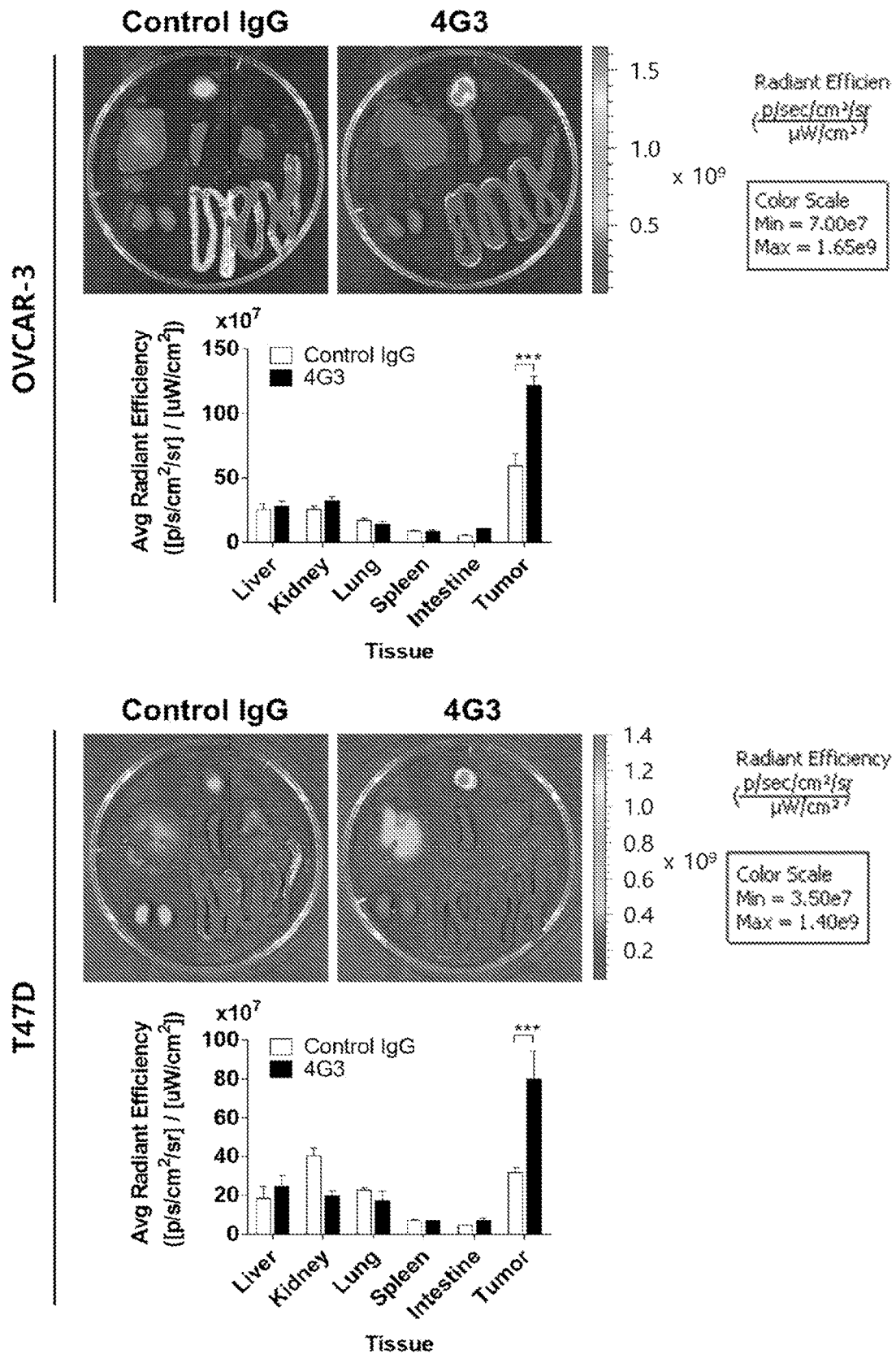
FIG. 14b shows the results of quantifying fluorescence intensity after organ extraction in the animal model.

As shown in FIGS. 14a and 14b, it was confirmed that the 4G3 antibody of the present invention specifically targeted the transplanted tumor as time passed compared to the control antibody and it was accumulated in the tumor compared to other tissues.

INDUSTRIAL APPLICABILITY

The invention of the present application relates to a use of an antibody biding specifically to ECL-2 of claudin 3 and functional fragments thereof in cancer cell detection, diagnosis, imaging, and application to cancer treatment (anti-cancer use of the antibody itself, and application to ADC and CAR-expression cells (particularly immune cells)), an antibody that includes a characteristic CDR sequence exerting a remarkable effect in such uses, and a functional fragment thereof.

Antibodies and functional fragments thereof that specifically bind to ECL-2 of claudin 3 are more effective in cancer cell detection, diagnosis, imaging, and application to cancer treatment (application to ADC and CAR-expressing cells (especially immune cells)) than other cancer antigens or conventional antibodies targeting ECL-1 of claudin 3. In particular, as a specific example of this, the antibody comprising the unique CDR sequence provided by the present invention not only possesses anticancer ability by itself, but also exhibits excellent cancer cell targeting ability without cross-reactivity with other claudin families. It is also advantageous for non-clinical experiments of toxicity and efficacy evaluation due to binding to mouse claudin 3, exhibits excellent binding strength (affinity), possesses properties such as cell internalization, and thus exhibits remarkable effects in application to the above use. Therefore, it has high industrial applicability in diagnostic and pharmaceutical industries.

What is claimed is:

1. An antibody or functional fragment thereof comprising:

a heavy chain variable region comprising a heavy chain complementarity determining region 1 (VH-CDR1) comprising an amino acid sequence defined by SEQ ID NO: 3, a heavy chain complementarity determining region 2 (VH-CDR2) comprising an amino acid sequence defined by SEQ ID NO: 4, and a heavy chain complementarity determining region 3 (VH-CDR3) comprising an amino acid sequence defined by SEQ ID NO: 5; and a light chain variable region comprising a light chain complementarity determining region 1 (VL-CDR1) comprising an amino acid sequence defined by SEQ ID NO: 6, a light chain complementarity determining region 2 (VL-CDR2) comprising an amino acid sequence defined by SEQ ID NO: 7, and a light chain complementarity determining region 3 (VL-CDR3) comprising an amino acid sequence defined by SEQ ID NO: 8.

2. The antibody or functional fragment thereof according to claim 1, wherein the antibody is selected from the group consisting of IgG, IgA, IgM, IgE and IgD, and the functional fragment is selected from the group consisting of diabody, Fab, F(ab'), F(ab')2, Fv, dsFv, and scFv.

3. The antibody or functional fragment thereof according to claim 1, wherein the antibody or functional fragment thereof is internalized into cells after binding to claudin 3.

4. The antibody or functional fragment thereof according to claim 3, wherein the antibody or functional fragment thereof specifically binds to an extracellular second loop of claudin 3.

5. A method for preparing an antibody or functional fragment thereof which specifically binds to claudin 3 protein, the method comprising:

preparing a polypeptide comprising a light chain and a heavy chain variable region by culturing a cell comprising a vector comprising a polynucleotide encoding the antibody or functional fragment thereof of claim 1; and recovering the polypeptide from the cell or a culture medium in which the cell is cultured.

6. A method for specifically detecting claudin 3, the method comprising:

contacting the antibody or functional fragment thereof of claim 1 with a sample; and detecting the antibody or functional fragment thereof.

7. The method of claim 6, wherein the antibody or functional fragment thereof is labeled with one or more selected from the group consisting of chromogenic enzymes, radioactive isotopes, chromophores, luminescent substances, fluorescers, superparamagnetic particles, and ultra-super paramagnetic particles.

8. CAR (chimeric antigen receptor) protein comprising the antibody or a functional fragment thereof of claim 1.

9. The CAR protein of claim 8, wherein the CAR protein comprises i) the antibody or a functional fragment thereof;

ii) a transmembrane domain; and iii) an intracellular signaling domain that causes cell activation when an antigen binds to the antibody or functional fragment thereof.

10. An immune cell comprising the CAR protein of claim 9.

11. The immune cell of claim 10, wherein the immune cell is selected from the group consisting of T cells, NK (Natural Killer) cells, NKT (Natural Killer T) cells, monocytes, macrophages and dendritic cells.

12. The CAR protein of claim 9, wherein the intracellular signaling domain is a signaling domain selected from the group consisting of CD3 zeta (ξ, zeta), TCR zeta, FcR gamma, FcR beta, CD3 gamma, CD3 delta, CD3 epsilon, CDS, CD22, CD79a, CD79b, CD278, CD66d, DAP10, DAP12, FcRI, and a combination thereof.

13. The CAR protein of claim 9, wherein the intracellular signaling domain further comprises a co-stimulatory domain.

14. The CAR protein of claim 13, wherein the co-stimulatory domain is derived from a co-stimulatory molecule selected from the group consisting of a ligand specifically binding to MHC class I molecules, TNF receptor proteins, Immunoglobulin-like proteins, and cytokine receptors, integrins, SLAM proteins (signaling lymphocytic activation molecules), NK cell activating receptors, BTLA, Toll ligand receptor, OX40, CD2, CD7, CD27, CD28, CD30, CD40, CDS, ICAM-1, LFA-1(CD11a/CD18, lymphocyte function-associated antigen-1), 4-1BB(CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD 83, PD-1, and combinations thereof.

15. A method for specific detection of claudin 3, comprising administering an effective amount of a composition comprising the antibody or functional fragment thereof of claim 1 as an active ingredient to a subject in need thereof.

16. A method for treating cancer, comprising administering an effective amount of a composition comprising the antibody or functional fragment thereof of claim 1 as an active ingredient to a subject in need thereof.

17. The method of claim 16, wherein the cancer is selected from the group consisting of ovarian cancer, colon cancer, bladder cancer, lung cancer, liver cancer, stomach cancer, esophageal cancer, breast cancer, prostate cancer, pancreatic cancer, uterine cancer, cervical cancer, melanoma, colorectal cancer, kidney cancer, and metastatic pleural tumor.

* * * * *

SEQUENCE LISTING

```
<160> NUMBER OF SEQ ID NOS: 41

<210> SEQ ID NO 1
<211> LENGTH: 220
<212> TYPE: PRT
<213> ORGANISM: Artificial Sequence
<220> FEATURE:
<223> OTHER INFORMATION: CLDN3(homo sapiens)

<400> SEQUENCE: 1

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
                20                  25                  30

Ala Phe Ile Gly Ser Asn Ile Ile Thr Ser Gln Asn Ile Trp Glu Gly
            35                  40                  45

Leu Trp Met Asn Cys Val Val Gln Ser Thr Gly Gln Met Gln Cys Lys
        50                  55                  60

Val Tyr Asp Ser Leu Leu Ala Leu Pro Gln Asp Leu Gln Ala Ala Arg
65                  70                  75                  80

Ala Leu Ile Val Val Ala Ile Leu Leu Ala Ala Phe Gly Leu Leu Val
                85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
        115                 120                 125

Leu Leu Thr Leu Val Pro Val Ser Trp Ser Ala Asn Thr Ile Ile Arg
    130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Leu Gln Leu Leu Gly
                165                 170                 175

Gly Ala Leu Leu Cys Cys Ser Cys Pro Pro Arg Glu Lys Lys Tyr Thr
            180                 185                 190
```

-continued

```
Ala Thr Lys Val Val Tyr Ser Ala Pro Arg Ser Thr Gly Pro Gly Ala
            195                 200                 205

Ser Leu Gly Thr Gly Tyr Asp Arg Lys Asp Tyr Val
    210                 215                 220

<210> SEQ ID NO 2
<211> LENGTH: 16
<212> TYPE: PRT
<213> ORGANISM: Artificial Sequence
<220> FEATURE:
<223> OTHER INFORMATION: extracellular 2nd loop sequence of CLDN3

<400> SEQUENCE: 2

Arg Asp Phe Tyr Asn Pro Val Val Pro Glu Ala Gln Lys Arg Glu Met
1               5                   10                  15

<210> SEQ ID NO 3
<211> LENGTH: 5
<212> TYPE: PRT
<213> ORGANISM: Artificial Sequence
<220> FEATURE:
<223> OTHER INFORMATION: VH-CDR1 of 4G3

<400> SEQUENCE: 3

Ser Tyr Ala Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: VH-CDR2 of 4G3

<400> SEQUENCE: 4

Ile Ile Asn Pro Ser Gly Ala Ser Thr Ser His Ala Gln Arg Phe Gln
1               5                   10                  15
Gly

<210> SEQ ID NO 5
<211> LENGTH: 10
<212> TYPE: PRT
<213> ORGANISM: Artificial Sequence
<220> FEATURE:
<223> OTHER INFORMATION: VH-CDR3 of 4G3

<400> SEQUENCE: 5

Arg Tyr Gly Arg Tyr Gly Ser Phe Asp Ile
1               5                   10

<210> SEQ ID NO 6
<211> LENGTH: 13
<212> TYPE: PRT
<213> ORGANISM: Artificial Sequence
<220> FEATURE:
<223> OTHER INFORMATION: VL-CDR1 of 4G3

<400> SEQUENCE: 6

Ser Gly Ser Thr Ser Asn Ile Gly Arg Asn Tyr Val Ser
1               5                   10

<210> SEQ ID NO 7
<211> LENGTH: 7
<212> TYPE: PRT
<213> ORGANISM: Artificial Sequence
<220> FEATURE:
```

<223> OTHER INFORMATION: VL-CDR2 of 4G3

<400> SEQUENCE: 7

Asp Thr Ser Asn Lys His Phe
1               5

<210> SEQ ID NO 8
<211> LENGTH: 9
<212> TYPE: PRT
<213> ORGANISM: Artificial Sequence
<220> FEATURE:
<223> OTHER INFORMATION: VL-CDR3 of 4G3

<400> SEQUENCE: 8

Gln Ser Tyr Asp Ser Ser Lys Val Val
1               5

<210> SEQ ID NO 9
<211> LENGTH: 92
<212> TYPE: DNA
<213> ORGANISM: Artificial Sequence
<220> FEATURE:
<223> OTHER INFORMATION: forward primer for light chain of 4G3

<400> SEQUENCE: 9
attcgatcga tatggagaca gacacactcc tgctatgggt actgctgctc tgggttccag        60
gttccacgtg gcagagcgtg ctgacccagc ct                                      92

<210> SEQ ID NO 10
<211> LENGTH: 33
<212> TYPE: DNA
<213> ORGANISM: Artificial Sequence
<220> FEATURE:
<223> OTHER INFORMATION: reverse primer for light chain of 4G3

<400> SEQUENCE: 10
agccaccgta cgcagcacgg tcagcttggt acc                                     33

<210> SEQ ID NO 11
<211> LENGTH: 92
<212> TYPE: DNA
<213> ORGANISM: Artificial Sequence
<220> FEATURE:
<223> OTHER INFORMATION: forward primer for heavy chain of 4G3

<400> SEQUENCE: 11
attcgatcga tatggagaca gacacactcc tgctatgggt actgctgctc tgggttccag        60
gttccacgtg ggaagtgcag ctgctggaaa gt                                      92

<210> SEQ ID NO 12
<211> LENGTH: 33
<212> TYPE: DNA
<213> ORGANISM: Artificial Sequence
<220> FEATURE:
<223> OTHER INFORMATION: reverse primer for heavy chain of 4G3

<400> SEQUENCE: 12
cttggtgcta gcgctgctca cggtcaccag agt                                     33

<210> SEQ ID NO 13
<211> LENGTH: 119
<212> TYPE: PRT
<213> ORGANISM: Artificial Sequence
<220> FEATURE:
<223> OTHER INFORMATION: VH of KM3907(ref. patent EP2138576A1)

-continued

<400> SEQUENCE: 13

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Ile Ser Thr Ser
            20                  25                  30

Trp Met Asn Trp Val Lys Gln Arg Pro Gly Lys Gly Leu Glu Trp Ile
        35                  40                  45

Gly Arg Ile Asn Pro Gly Asp Gly Asn Thr Asn Tyr Asn Gly Lys Phe
    50                  55                  60

Met Ala Lys Ala Thr Leu Thr Ala Asp Lys Pro Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Gly Asp Arg Trp Ser Gly Ala Met Asp Tyr Trp Gly Gln Gly
            100                 105                 110

Thr Ser Val Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: VL of KM3907(ref. patent EP2138576A1)

<400> SEQUENCE: 14

Gly Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Phe Pro
                85                  90                  95

Leu Thr Phe Gly Ala Gly Thr Lys Leu Glu Leu Lys
            100                 105

<210> SEQ ID NO 15
<211> LENGTH: 468
<212> TYPE: PRT
<213> ORGANISM: Artificial Sequence
<220> FEATURE:
<223> OTHER INFORMATION: Heavy chain of KM3907

<400> SEQUENCE: 15

Met Glu Trp Pro Cys Ile Phe Leu Phe Leu Leu Ser Val Thr Glu Gly
1               5                   10                  15

Val His Ser Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ala Ile
        35                  40                  45

Ser Thr Ser Trp Met Asn Trp Val Lys Gln Arg Pro Gly Lys Gly Leu
    50                  55                  60

```
Glu Trp Ile Gly Arg Ile Asn Pro Gly Asp Gly Asn Thr Asn Tyr Asn
 65                  70                  75                  80

Gly Lys Phe Met Ala Lys Ala Thr Leu Thr Ala Asp Lys Pro Ser Ser
                 85                  90                  95

Thr Ala Tyr Met Gln Leu Ser Ser Leu Thr Ser Glu Asp Ser Ala Val
                100                 105                 110

Tyr Phe Cys Thr Arg Gly Asp Arg Trp Ser Gly Ala Met Asp Tyr Trp
            115                 120                 125

Gly Gln Gly Thr Ser Val Thr Val Ser Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465
```

```
<210> SEQ ID NO 16
<211> LENGTH: 237
<212> TYPE: PRT
<213> ORGANISM: Artificial Sequence
<220> FEATURE:
<223> OTHER INFORMATION: lignt chain of KM3907

<400> SEQUENCE: 16

Met Asp Phe Leu Val Gln Ile Phe Ser Phe Leu Leu Ile Ser Ala Ser
1               5                   10                  15

Val Ala Met Ser Arg Gly Gly Asn Val Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Ser Ser Ser Tyr Leu His Trp Tyr Gln Gln Lys Ser Gly
    50                  55                  60

Ala Ser Pro Lys Leu Trp Ile Tyr Ser Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr Ser Gly Phe Pro Leu Thr Phe Gly Ala Gly Thr Lys Leu Glu
        115                 120                 125

Leu Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 17
<211> LENGTH: 15
<212> TYPE: DNA
<213> ORGANISM: Artificial Sequence
<220> FEATURE:
<223> OTHER INFORMATION: Linker

<400> SEQUENCE: 17
ggggsggggs ggggs                                                15

<210> SEQ ID NO 18
<211> LENGTH: 5
<212> TYPE: PRT
<213> ORGANISM: Artificial Sequence
<220> FEATURE:
<223> OTHER INFORMATION: VH-CDR1 of 2B4

<400> SEQUENCE: 18

Gly Tyr Tyr Trp Ser
1               5
```

```
<210> SEQ ID NO 19
<211> LENGTH: 17
<212> TYPE: PRT
<213> ORGANISM: Artificial Sequence
<220> FEATURE:
<223> OTHER INFORMATION: VH-CDR2 of 2B4

<400> SEQUENCE: 19

Thr Ile His Pro Gly Asp Ser Asp Thr Arg Tyr Asn Pro Ser Leu Gln
1               5                   10                  15

Gly

<210> SEQ ID NO 20
<211> LENGTH: 9
<212> TYPE: PRT
<213> ORGANISM: Artificial Sequence
<220> FEATURE:
<223> OTHER INFORMATION: VH-CDR3 of 2B4

<400> SEQUENCE: 20

Arg Gln Gly Tyr Ser Leu Phe Asp Ile
1               5

<210> SEQ ID NO 21
<211> LENGTH: 11
<212> TYPE: PRT
<213> ORGANISM: Artificial Sequence
<220> FEATURE:
<223> OTHER INFORMATION: VL-CDR1 of 2B4

<400> SEQUENCE: 21

Arg Ala Ser Gln Ser Val Ala Ser Asp Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: VL-CDR2 of 2B4

<400> SEQUENCE: 22

Ala Ala Ser Arg Leu Gln Ser
1               5

<210> SEQ ID NO 23
<211> LENGTH: 9
<212> TYPE: PRT
<213> ORGANISM: Artificial Sequence
<220> FEATURE:
<223> OTHER INFORMATION: VL-CDR3 of 2B4

<400> SEQUENCE: 23

Gln Gln Tyr Asn Ser Tyr Pro Pro Thr
1               5

<210> SEQ ID NO 24
<211> LENGTH: 54
<212> TYPE: PRT
<213> ORGANISM: Homo sapiens
<220> FEATURE:
<223> OTHER INFORMATION: Description of sequence: AA27-80 of Human
      Claudin 3

<400> SEQUENCE: 24
```

```
Pro Met Trp Arg Val Ser Ala Phe Ile Gly Ser Asn Ile Ile Thr Ser
1               5                   10                  15

Gln Asn Ile Trp Glu Gly Leu Trp Met Asn Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala Arg
    50

<210> SEQ ID NO 25
<211> LENGTH: 54
<212> TYPE: PRT
<213> ORGANISM: Homo sapiens
<220> FEATURE:
<223> OTHER INFORMATION: Description of sequence: AA28-81 of Human
      Claudin 4

<400> SEQUENCE: 25

Pro Met Trp Arg Val Thr Ala Phe Ile Gly Ser Asn Ile Val Thr Ser
1               5                   10                  15

Gln Thr Ile Trp Glu Gly Leu Trp Met Asn Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala Arg
    50

<210> SEQ ID NO 26
<211> LENGTH: 54
<212> TYPE: PRT
<213> ORGANISM: Homo sapiens
<220> FEATURE:
<223> OTHER INFORMATION: Description of sequence: AA28-81 of Human
      Claudin 5

<400> SEQUENCE: 26

Pro Met Trp Gln Val Thr Ala Phe Leu Asp His Asn Ile Val Thr Ala
1               5                   10                  15

Gln Thr Thr Trp Lys Gly Leu Trp Met Ser Cys Val Val Gln Ser Thr
            20                  25                  30

Gly His Met Gln Cys Lys Val Tyr Asp Ser Val Leu Ala Leu Ser Thr
        35                  40                  45

Glu Val Gln Ala Ala Arg
    50

<210> SEQ ID NO 27
<211> LENGTH: 54
<212> TYPE: PRT
<213> ORGANISM: Homo sapiens
<220> FEATURE:
<223> OTHER INFORMATION: Description of sequence: AA28-81 of Human
      Claudin 6

<400> SEQUENCE: 27

Pro Met Trp Lys Val Thr Ala Phe Ile Gly Asn Ser Ile Val Val Ala
1               5                   10                  15

Gln Val Val Trp Glu Gly Leu Trp Met Ser Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala Arg
```

<210> SEQ ID NO 28
<211> LENGTH: 54
<212> TYPE: PRT
<213> ORGANISM: Homo sapiens
<220> FEATURE:
<223> OTHER INFORMATION: Description of sequence: AA28-81 of Human
      Claudin 8

<400> SEQUENCE: 28

Pro Met Trp Arg Val Ser Ala Phe Ile Gly Ser Asn Ile Ile Thr Ser
1               5                   10                  15

Gln Asn Ile Trp Glu Gly Leu Trp Met Asn Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala Arg
    50

<210> SEQ ID NO 29
<211> LENGTH: 54
<212> TYPE: PRT
<213> ORGANISM: Homo sapiens
<220> FEATURE:
<223> OTHER INFORMATION: Description of sequence: AA28-81 of Human
      Claudin 9

<400> SEQUENCE: 29

Pro Leu Trp Lys Val Thr Ala Phe Ile Gly Asn Ser Ile Val Val Ala
1               5                   10                  15

Gln Val Val Trp Glu Gly Leu Trp Met Ser Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala Arg
    50

<210> SEQ ID NO 30
<211> LENGTH: 54
<212> TYPE: PRT
<213> ORGANISM: Homo sapiens
<220> FEATURE:
<223> OTHER INFORMATION: Description of sequence: AA28-81 of Human
      Claudin 17

<400> SEQUENCE: 30

Pro Gln Trp Arg Val Ser Ala Phe Val Gly Ser Asn Ile Ile Val Phe
1               5                   10                  15

Glu Arg Leu Trp Glu Gly Leu Trp Met Asn Cys Ile Arg Gln Ala Arg
            20                  25                  30

Val Arg Leu Gln Cys Lys Phe Tyr Asp Ser Leu Leu Ala Leu Pro Pro
        35                  40                  45

Ala Leu Glu Thr Ala Arg
    50

<210> SEQ ID NO 31
<211> LENGTH: 54
<212> TYPE: PRT
<213> ORGANISM: Homo sapiens
<220> FEATURE:
<223> OTHER INFORMATION: Description of sequence: AA28-81 of Human
      Claudin 1

```
<400> SEQUENCE: 31

Pro Gln Trp Arg Ile Tyr Ser Tyr Ala Gly Asp Asn Ile Val Thr Ala
1               5                   10                  15

Gln Ala Met Tyr Glu Gly Leu Trp Met Ser Cys Val Ser Gln Ser Thr
            20                  25                  30

Gly Gln Ile Gln Cys Lys Val Phe Asp Ser Leu Leu Asn Leu Ser Ser
        35                  40                  45

Thr Leu Gln Ala Thr Arg
    50

<210> SEQ ID NO 32
<211> LENGTH: 54
<212> TYPE: PRT
<213> ORGANISM: Mus musculus
<220> FEATURE:
<223> OTHER INFORMATION: Description of sequence: AA27-80 of Mouse
      MClaudin3

<400> SEQUENCE: 32

Pro Met Trp Arg Val Ser Ala Phe Ile Gly Ser Ser Ile Ile Thr Ala
1               5                   10                  15

Gln Ile Thr Trp Glu Gly Leu Trp Met Asn Cys Val Val Gln Ser Thr
            20                  25                  30

Gly Gln Met Gln Cys Lys Met Tyr Asp Ser Leu Leu Ala Leu Pro Gln
        35                  40                  45

Asp Leu Gln Ala Ala Arg
    50

<210> SEQ ID NO 33
<211> LENGTH: 16
<212> TYPE: PRT
<213> ORGANISM: Homo sapiens
<220> FEATURE:
<223> OTHER INFORMATION: Description of sequence: AA144-159 of Human
      Claudin 3

<400> SEQUENCE: 33

Arg Asp Phe Tyr Asn Pro Val Val Pro Glu Ala Gln Lys Arg Glu Met
1               5                   10                  15

<210> SEQ ID NO 34
<211> LENGTH: 16
<212> TYPE: PRT
<213> ORGANISM: Homo sapiens
<220> FEATURE:
<223> OTHER INFORMATION: Description of sequence: AA145-160 of Human
      Claudin 4

<400> SEQUENCE: 34

Gln Asp Phe Tyr Asn Pro Leu Val Ala Ser Gly Gln Lys Arg Glu Met
1               5                   10                  15

<210> SEQ ID NO 35
<211> LENGTH: 16
<212> TYPE: PRT
<213> ORGANISM: Homo sapiens
<220> FEATURE:
<223> OTHER INFORMATION: Description of sequence: AA145-160 of Human
      Claudin 5

<400> SEQUENCE: 35

Arg Glu Phe Tyr Asp Pro Ser Val Pro Val Ser Gln Lys Tyr Glu Leu
1               5                   10                  15
```

```
<210> SEQ ID NO 36
<211> LENGTH: 16
<212> TYPE: PRT
<213> ORGANISM: Homo sapiens
<220> FEATURE:
<223> OTHER INFORMATION: Description of sequence: AA145-160 of Human
      Claudin 6

<400> SEQUENCE: 36

Arg Asp Phe Tyr Asn Pro Leu Val Ala Glu Ala Gln Lys Arg Glu Leu
1               5                   10                  15

<210> SEQ ID NO 37
<211> LENGTH: 16
<212> TYPE: PRT
<213> ORGANISM: Homo sapiens
<220> FEATURE:
<223> OTHER INFORMATION: Description of sequence: AA145-160 of Human
      Claudin 8

<400> SEQUENCE: 37

Arg Asp Phe Tyr Asn Ser Ile Val Asn Val Ala Gln Lys Arg Glu Leu
1               5                   10                  15

<210> SEQ ID NO 38
<211> LENGTH: 16
<212> TYPE: PRT
<213> ORGANISM: Homo sapiens
<220> FEATURE:
<223> OTHER INFORMATION: Description of sequence: AA145-160 of Human
      Claudin 9

<400> SEQUENCE: 38

Gln Asp Phe Tyr Asn Pro Leu Val Ala Glu Ala Leu Lys Arg Glu Leu
1               5                   10                  15

<210> SEQ ID NO 39
<211> LENGTH: 16
<212> TYPE: PRT
<213> ORGANISM: Homo sapiens
<220> FEATURE:
<223> OTHER INFORMATION: Description of sequence: AA145-160 of Human
      Claudin 17

<400> SEQUENCE: 39

Arg Asp Phe Tyr Asn Pro Ala Ile His Ile Gly Gln Lys Arg Glu Leu
1               5                   10                  15

<210> SEQ ID NO 40
<211> LENGTH: 16
<212> TYPE: PRT
<213> ORGANISM: Homo sapiens
<220> FEATURE:
<223> OTHER INFORMATION: Description of sequence: AA145-160 of Human
      Claudin 1

<400> SEQUENCE: 40

Gln Glu Phe Tyr Asp Pro Met Thr Pro Val Asn Ala Arg Tyr Glu Phe
1               5                   10                  15

<210> SEQ ID NO 41
<211> LENGTH: 16
<212> TYPE: PRT
<213> ORGANISM: Mus musculus
<220> FEATURE:
<223> OTHER INFORMATION: Description of sequence: AA144-159 of Mouse
      Claudin 3
```

```
<400> SEQUENCE: 41

Arg Asp Phe Tyr Asn Pro Leu Val Pro Glu Ala Gln Lys Arg Glu Met
1               5                   10                  15
```